United States Patent
Shemshedini et al.

(10) Patent No.: US 9,546,196 B2
(45) Date of Patent: Jan. 17, 2017

(54) COMPOSITIONS AND METHODS OF TREATMENT OF CANCERS

(71) Applicant: The University of Toledo, Toledo, OH (US)

(72) Inventors: Lirim Shemshedini, Ypsilanti, MI (US); Shao-Yong Chen, Brookline, MA (US); Changmeng Cai, Newton, MA (US); Chen-Lin Hsieh, Brighton, MA (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 15/040,228

(22) Filed: Feb. 10, 2016

(65) Prior Publication Data
US 2016/0152665 A1 Jun. 2, 2016

Related U.S. Application Data

(60) Division of application No. 14/069,790, filed on Nov. 1, 2013, now Pat. No. 9,301,991, which is a continuation-in-part of application No. 13/375,307, filed as application No. PCT/US2010/036563 on May 28, 2010, now Pat. No. 8,575,087.

(60) Provisional application No. 61/182,712, filed on May 30, 2009.

(51) Int. Cl.

| | |
|---|---|
| *A61K 38/04* | (2006.01) |
| *C07K 7/08* | (2006.01) |
| *A61K 38/10* | (2006.01) |
| *C07K 7/06* | (2006.01) |
| *C07K 5/103* | (2006.01) |
| *C07K 5/083* | (2006.01) |
| *A61K 38/08* | (2006.01) |
| *A61K 38/06* | (2006.01) |
| *A61K 38/07* | (2006.01) |
| *A61K 31/7048* | (2006.01) |
| *C07K 5/11* | (2006.01) |
| *C07K 5/107* | (2006.01) |
| *C12N 9/88* | (2006.01) |
| *A61K 45/06* | (2006.01) |
| *A61K 38/00* | (2006.01) |

(52) U.S. Cl.
CPC .............. *C07K 7/08* (2013.01); *A61K 31/7048* (2013.01); *A61K 38/06* (2013.01); *A61K 38/07* (2013.01); *A61K 38/08* (2013.01); *A61K 38/10* (2013.01); *A61K 45/06* (2013.01); *C07K 5/081* (2013.01); *C07K 5/1013* (2013.01); *C07K 5/1016* (2013.01); *C07K 5/1019* (2013.01); *C07K 7/06* (2013.01); *C12N 9/88* (2013.01); *C12Y 406/01002* (2013.01); *A61K 38/00* (2013.01)

(58) Field of Classification Search
CPC .................................. C07K 7/08; A61K 38/10
See application file for complete search history.

(56) References Cited

U.S. PATENT DOCUMENTS

| | | |
|---|---|---|
| 8,575,087 B2 | 11/2013 | Shemshedini et al. |
| 2003/0157082 A1 | 8/2003 | Hunter et al. |
| 2012/0172310 A1 | 7/2012 | Shemshedini et al. |
| 2013/0274204 A1 | 10/2013 | Shailubhai et al. |
| 2014/0057852 A1 | 2/2014 | Shemshedini et al. |
| 2014/0057853 A1 | 2/2014 | Shemshedini et al. |
| 2014/0088023 A1 | 3/2014 | Shemshedini et al. |

FOREIGN PATENT DOCUMENTS

WO 2010/141349 A1 12/2010

OTHER PUBLICATIONS

PCT International Preliminary Report on Patentability, Application No. PCT/US2010/036563 filed May 28, 2010, dated Dec. 6, 2011, [53-50574/D2009-27].
PCT International Search Report and the Written Opinion, Application No. PCT/US2010/036563 filed May 28, 2010, dated Oct. 6, 2010, [53-50574/D2009-27].
PCT International Search Report and the Written Opinion, Application No. PCT/US2014/063089 filed Oct. 30, 2014, dated Apr. 28, 2015, [53-55242/D2013-86].
Cai et al., "Androgen regulation of soluble guanylyl cyclaseα1 mediates prostate cancer cell proliferation", Oncogene, 2007, vol. 26, pp. 1606-1615.
Fraser et al., "Regulation of p53 and suppression of apoptosis by the soluble guanylyl cyclase/cGMP pathway in human ovarian caner cells", Oncogene, 2006, vol. 25, pp. 2203-2212.
Gao et al., "A Peptide against Soluble Guanylyl Cyclase α1: A New Approach to Treating Prostate Cancer", PLOS One, 2013, vol. 8, No. 5, pp. 1-11.

*Primary Examiner* — Prema Mertz
(74) *Attorney, Agent, or Firm* — MacMillan, Sobanski & Todd, LLC

(57) ABSTRACT

Described herein are compositions and methods useful to treat cancers. In addition, the present invention provides screening assays, diagnostic assays, methods to prognose, methods to treat, and kits.

3 Claims, 34 Drawing Sheets
(22 of 34 Drawing Sheet(s) Filed in Color)

FIG. 1B  FIG. 1C

| Gene ID | Symbol | Fold change of Expression | Description |
|---|---|---|---|
| NM_022112 | P53AIP1 | I (29.41) | P53-regulated apoptosis-inducing protein 1 |
| NM_020418 | PCBP4 | I (31.50) | Poly(rC) binding protein 4 |
| NM_001168 | BIRC5 | D (4.42) | Baculoviral IAP repeart-containing 5 (surviving) |

Peptide A-8R
Ac-TFCKAFPFHIIRRRRRRRR-OH

Peptide B-8R
Ac-LRLKGQMIYLRRRRRRRR-OH

Peptide C-8R
Ac-PLHDATRDLVRRRRRRRR-OH

Peptide D-8R
Ac-RALEDEKKKTDTLLYSVL
PPRRRRRRRR-OH

Capan-2 Cells

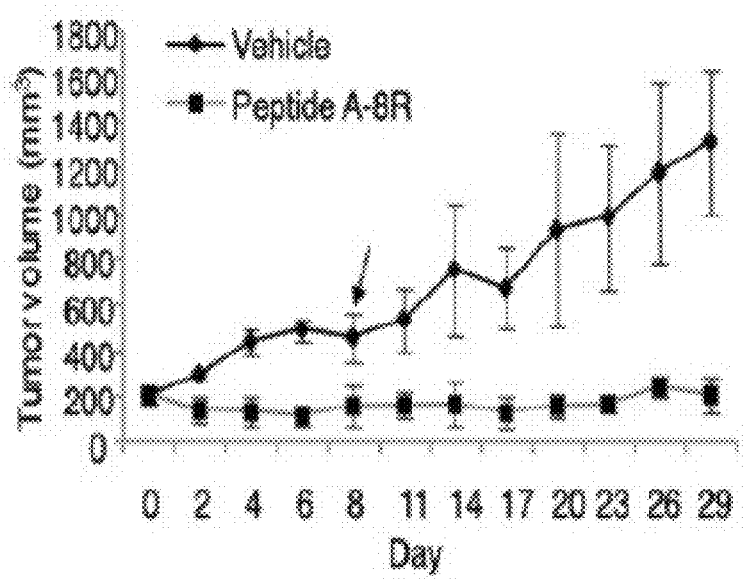
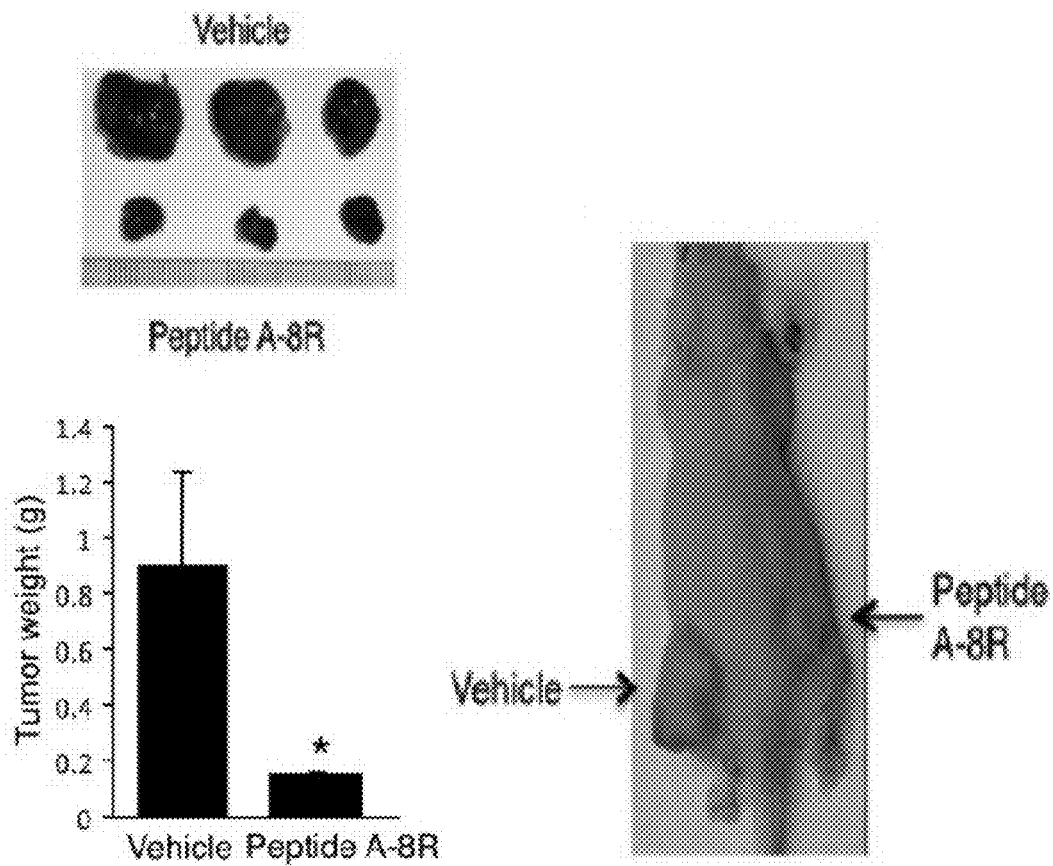
FIG. 28A
FIG. 28B
FIG. 28C

```
                         SEQUENCE LISTING

<160> NUMBER OF SEQ ID NOS: 36

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Phe Cys Lys Ala Phe Pro Phe His Ile Ile Arg Arg Arg Arg
1               5                   10                  15

Arg Arg Arg

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Arg Leu Lys Gly Gln Met Ile Tyr Leu Arg Arg Arg Arg Arg
1               5                   10                  15

Arg Arg

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Leu His Asp Ala Thr Arg Asp Leu Val Arg Arg Arg Arg Arg
1               5                   10                  15

Arg Arg

<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Leu Glu Asp Glu Lys Lys Lys Thr Asp Thr Leu Leu Tyr Ser
1               5                   10                  15

Val Leu Pro Pro Arg Arg Arg Arg Arg Arg Arg
            20                  25

<210> SEQ ID NO 5
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 5

Thr Phe Cys Lys Ala Phe Pro Phe His Ile Ile
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Arg Arg Arg Arg Arg Arg Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Phe Cys Lys Ala Phe Pro
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Pro Phe His Ile Ile
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Phe Cys Lys Ala Phe
1               5

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Phe Cys Lys Ala Phe Arg Arg Arg Arg Arg Arg Arg Arg
1               5                   10
```

```
<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Pro Phe His Ile Ile Arg Arg Arg Arg Arg Arg Arg Arg
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Phe Cys Lys Ala Phe Pro Arg Arg Arg Arg Arg Arg Arg Arg
1               5                   10                  15

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Phe Cys Lys Ala Phe
1               5

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Phe Cys Lys Ala Phe Arg Arg Arg Arg Arg Arg Arg Arg
1               5                   10

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Cys Lys Ala Phe Pro
1               5

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16
```

```
Phe Cys Lys Ala Phe Pro Arg Arg Arg Arg Arg Arg Arg
1               5                  10
```

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Phe Met Lys Ala Phe
1               5
```

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Phe Met Lys Ala Phe Arg Arg Arg Arg Arg Arg Arg
1               5                  10
```

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Phe Ala Lys Ala Phe
1               5
```

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Phe Ala Lys Ala Phe Arg Arg Arg Arg Arg Arg Arg
1               5                  10
```

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Ala Cys Lys Ala Phe
1               5
```

<210> SEQ ID NO 22
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 22

Ala Cys Lys Ala Phe Arg Arg Arg Arg Arg Arg Arg
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Phe Cys Lys Ala Ala
1               5

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Phe Cys Lys Ala Ala Arg Arg Arg Arg Arg Arg Arg
1               5                   10

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Phe Cys Ala Ala Phe
1               5

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Phe Cys Ala Ala Phe Arg Arg Arg Arg Arg Arg Arg
1               5                   10

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Phe Cys Lys Ala
1
```

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Phe Cys Lys Ala Arg Arg Arg Arg Arg Arg Arg Arg
1               5                   10

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Cys Lys Ala Phe
1

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Lys Ala Phe Arg Arg Arg Arg Arg Arg Arg Arg
1               5                   10

<210> SEQ ID NO 31
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Thr Phe Cys
1

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Phe Cys Arg Arg Arg Arg Arg Arg Arg Arg
1               5                   10

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 33

Lys Ala Phe Pro
1

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Ala Phe Pro Arg Arg Arg Arg Arg Arg Arg Arg
1               5                   10

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Ala Phe Pro Phe His
1               5

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Ala Phe Pro Phe His Arg Arg Arg Arg Arg Arg Arg Arg
1               5                   10
```

COMPOSITIONS AND METHODS OF TREATMENT OF CANCERS

CROSS-REFERENCE TO RELATED APPLICATIONS

The present application is a divisional application of U.S. Ser. No. 14/069,790 filed Nov. 1, 2013, now allowed, which is a continuation-in-part application of U.S. Ser. No. 13/375,307, filed under 35 U.S.C. §371 on Dec. 22, 2011, now U.S. Pat. No. 8,575,087 issued Nov. 5, 2013; which is the national stage entry of PCT/US2010/036563, filed under the authority of the Patent Cooperation Treaty on May 28, 2010; which claims priority to U.S. Provisional Application Ser. No. 61/182,712, filed under 35 U.S.C. §111(b) on May 30, 2009. The disclosure of each priority document is hereby incorporated by reference in its entirety.

STATEMENT REGARDING SPONSORED RESEARCH

This invention was made with government support under Grant No. DK067059 and Grant No. CA127873 awarded by National Institutes of Health. The government has certain rights in this invention.

SEQUENCE LISTING

The instant application contains a Sequence Listing which has been submitted via EFS-web and is hereby incorporated by reference in its entirety. The ASCII copy, created on Oct. 29, 2013, is named 1-55242-D2013-86_SL.txt, and is 8,959 bytes in size.

A brief description of the sequence listing is presented in the following table.

| SEQ ID NO: | Description | Sequence (N terminus to C terminus) |
|---|---|---|
| 1 | A-8R | TFCKAFPFHIIRRRRRRRR |
| 2 | B-8R | LRLKGQMIYLRRRRRRRR |
| 3 | C-8R | PLHDATRDLVRRRRRRRR |
| 4 | D-8R | RALEDEKKKTDTLLYSVLPPRRRRRRRR |
| 5 | Modified A-8R [SEQ ID NO: 1] (no C-terminal arginines) | TFCKAFPFHII |
| 6 | 8R | RRRRRRRR |
| 7 | TP7 (first half amino acids) | TFCKAFP |
| 8 | PI5 (second half amino acids) | PFHII |
| 9 | FF5 | FCKAF |
| 10 | FF5-8R | FCKAFRRRRRRRR |
| 11 | PI5-8R | PFHIIRRRRRRRR |
| 12 | TP7-8R | TFCKAFPRRRRRRRR |
| 13 | TF6 | TFCKAF |
| 14 | TF6-8R | TFCKAFRRRRRRRR |
| 15 | FP6 | FCKAFP |
| 16 | FP6-8R | FCKAFPRRRRRRRR |
| 17 | FF5-C2M | FMKAF |
| 18 | FF5-C2M-8R | FMKAFRRRRRRRR |
| 19 | FF5-C2A | FAKAF |
| 20 | FF5-C2A-8R | FAKAFRRRRRRRR |
| 21 | FF5-F1A | ACKAF |
| 22 | FF5-F1A-8R | ACKAFRRRRRRRR |
| 23 | FF5-F5 A | FCKAA |
| 24 | FF5-F5 A-8R | FCKAARRRRRRRR |
| 25 | FF5-K3 A | FCAAF |
| 26 | FF5-K3 A-8R | FCAAFRRRRRRRR |
| 27 | FA4 | FCKA |
| 28 | FA4-8R | FCKARRRRRRRR |
| 29 | CF4 | CKAF |
| 30 | CF4-8R | CKAFRRRRRRRR |
| 31 | TC3 | TFC |
| 32 | TC3-8R | TFCRRRRRRRR |
| 33 | KP4 | KAFP |
| 34 | KP4-8R | KAFPRRRRRRRR |
| 35 | KH6 | KAFPFH |
| 36 | KH6-8R | KAFPFHRRRRRRRR |

BACKGROUND

Certain cancers, such as prostate cancer, which is the second leading cause of cancer deaths among men, largely depend on androgens for their development and progression. Androgen effects in prostate and other tissues are mediated by the androgen receptor (AR). This protein binds to and is activated by androgens. The importance of the androgen receptor in the development of prostate cancer is demonstrated by the success of anti-androgen therapy at the early stages of prostate cancer. Hormone ablation therapies continue to dominate the market, as they have proven to be the most effective at treating the early stage prostate cancer, which is hormone-dependent.

However, this therapy and others currently used are ineffective against late-stage prostate cancer, which is hormone-refractory and usually lethal.

SUMMARY OF THE INVENTION

In a first broad aspect, there are provided herein representative methods to treat conditions such as cancer and cancer-related conditions. A representative method includes administering to a subject in need of treatment an effective amount of at least one effector agent.

In another broad aspect, the present invention is based, at least in part, on the discovery of a protein product which is able to down-regulate p53 activity in prostate cancer cells. Since disrupting mutations of p53 mainly occur in late-stage, hormone-refractory prostate tumors and are found in less than 50% of these tumors, this mechanism of p53 down-regulation is now believed to be important in those 50% of tumors that express wild-type p53 protein. It is also now believed that disrupting this mechanism of p53 down-regulation provides a new therapy against such tumors.

Compositions are Provided Herein.

Described herein are compositions of matter comprising a sGCα1 inhibitor. Specifically provided are those compositions wherein the inhibitor is capable of reducing sGCα1-associated p53 inhibition. Also specifically provided are those compositions wherein the inhibitor is capable of increasing apoptosis of cancer cells capable of expressing sGCα1 and p53. Also specifically provided are those compositions wherein the inhibitor is capable of increasing apoptosis of sGCα1-expressing cancer cells selected from the group consisting of: hormone refractory prostate cancer cells, metastatic prostate cancer cells, late stage prostate cancer cells, pancreatic cancer cells, and gastrointestinal cancer cells. Also specifically provided are those compositions wherein the inhibitor is selected from the group consisting of: a small molecule, a peptide, an sCGβ1 mimic, an sCGβ1/sGCα1 dimerization inhibitor, a silencing RNA, and an antibody. Also specifically provided are those compositions wherein the inhibitor comprises a peptide. More specifically provided are those compositions wherein the peptide is selected from the group consisting of: A-8R [SEQ ID NO: 1], a functional variant of A-8R [SEQ ID NO: 1], a conserved variant of A-8R [SEQ ID NO: 1], B-8R [SEQ ID NO: 2], and a functional variant of B-8R [SEQ ID NO: 2]. More specifically provided wherein the peptide comprises A-8R [SEQ ID NO: 1]. More specifically provided which comprises the peptide TFCKAFPFHII [SEQ ID NO:5], or a conserved variants thereof, and means for translocating the peptide across a plasma membrane. Further provided are truncated A-8R [SEQ ID NO: 1] sequences and derivatives thereof.

More specifically provided are compositions which are pharmaceutical formulations, and/or which further comprises a composition selected from the group consisting of: an adjuvant, a pharmaceutically-acceptable salt, a prodrug, a buffer, and a biomarker and/or which further comprises a chemotherapeutic agent, especially wherein the chemotherapeutic agent is etoposide.

Methods for Identifying Useful Compositions are Provided Herein.

Included are methods to identify compositions capable of increasing apoptosis of cancer cells, comprising introducing at least one test composition to a plurality of sGCα1-expressing cancer cells, and identifying whether the test composition increases apoptosis of the cells.

Also provided are methods to identify compositions capable of inhibiting cancer tumor growth, comprising introducing at least one test composition to a plurality of sGCα1-expressing cancer tumor cells, and identifying whether the test composition inhibits cancer tumor cell growth.

Also provided are methods to identify compositions capable of increasing cancer tumor regression, comprising introducing at least one test composition to a plurality of sGCα1-expressing cancer tumor cells, and identifying whether the test composition increases tumor cell regression.

Also provided are methods to identify compositions capable of inhibiting cancer cell proliferation, comprising introducing at least one test composition to a plurality of sGCα1-expressing cancer cells, and identifying whether the test composition inhibits cell proliferation.

Also provided are methods to identify compositions capable of treating cancer, comprising introducing a test composition to a plurality of sGCα1-expressing cancer cells, and identifying whether the test composition increases apoptosis of the cells. Specifically provided are those methods wherein the cancer is selected from the group comprising: neuroblastoma; lung cancer; bile duct cancer; non small cell lung carcinoma; hepatocellular carcinoma; lymphoma; nasopharyngeal carcinoma; ovarian cancer; head and neck squamous cell carcinoma; squamous cell cervical carcinoma; gastric cancer; colon cancer; uterine cervical carcinoma; gall bladder cancer; prostate cancer; breast cancer; testicular germ cell tumors; large cell lymphoma; follicular lymphoma; colorectal cancer; malignant pleural mesothelioma; glioma; thyroid cancer; basal cell carcinoma; T cell lymphoma; t(8;17)-prolyphocytic leukemia; myelodysplastic syndrome; pancreatic cancer; t(5;14)(q35.1;q32.2) leukemia; malignant fibrous histiocytoma; gastrointestinal stromal tumor; and hepatoblastoma; colorectal; endometrial; ovarian; gastric; and urothelial.

Also provided are methods to identify compositions capable of treating hormone-refractory prostate cancer, comprising introducing a test composition to a plurality of hormone-refractory prostate cancer cells, and identifying whether the test composition increases apoptosis of the cells.

Also provided are methods to identify compositions capable of treating metastatic prostate cancer, comprising introducing a test composition to a plurality of metastatic prostate cancer cells, and identifying whether the test composition increases apoptosis of the cells.

Also provided are methods to identify compositions capable of treating late stage prostate cancer, comprising introducing a test composition to a plurality of late stage prostate cancer cells, and identifying whether the test composition increases apoptosis of the cells.

Also provided are methods to identify compositions capable of treating pancreatic cancer, comprising introducing a test composition to a plurality of sGCα1-expressing cancer cells, and identifying whether the test composition increases apoptosis of the cells.

Also provided are methods to identify compositions capable of treating gastrointestinal cancer, comprising introducing a test composition to a plurality of sGCα1-expressing gastrointestinal cancer cells, and identifying whether the test composition increases apoptosis of the cells.

Also provided are methods to identify compositions capable of treating breast cancer, comprising introducing a test composition to a plurality of sGCα1-expressing breast cancer cells, and identifying whether the test composition increases apoptosis of the cells.

Methods to Influence Cells are Provided Herein.

Included are methods to affect apoptosis of sGCα1-expressing cancer cells, comprising introducing an apoptosis-affecting amount of a composition capable of affecting sGCα1 activity to sGCα1-expressing cancer cells.

Also provided are methods to increase apoptosis of sGCα1-expressing cancer cells, comprising introducing an apoptosis-increasing amount of a sGCα1 inhibitor to sGCα1-expressing cancer cells.

Also provided are methods to inhibit tumor growth of sGCα1-expressing cancer cells, comprising introducing an tumor growth-inhibiting amount of a sGCα1 inhibitor to sGCα1-expressing cancer cells.

Also provided are methods to increase regression of sGCα1-expressing cancer cells, comprising introducing an regression-increasing amount of a sGCα1 inhibitor to sGCα1-expressing cancer cells.

Also provided are methods to inhibit proliferation of sGCα1-expressing cancer cells, comprising introducing an proliferation-inhibiting amount of a sGCα1 inhibitor to sGCα1-expressing cancer cells.

Also provided are methods to affect p53 activity in sGCα1-expressing cancer cells, comprising introducing a p53 activity-affecting amount of a composition capable of affecting sGCα1 to sGCα1-expressing cancer cells.

Also provided are methods to increase p53 activity in sGCα1-expressing cells, comprising introducing a p53 activity-increasing amount of a sGCα1 inhibitor to sGCα1-expressing cancer cells.

Also provided are methods for up-regulating expression of the tumor suppressor p53 gene in a subject in need thereof, comprising administering an effective amount of a composition comprising a peptide having at least 5-10 consecutive residues of sGCβ1 and which binds to sGCα1 such that expression of the tumor suppressor p53 gene is up-regulated.

Methods as Above Have Many Embodiments, as Provided Herein.

Included in the present invention are methods wherein the cells are in vitro.

Also provided are those methods wherein the cells are selected from the group consisting of: LNCaP cells, C81 cells, Capan-2, and CWR22-Rv1 cells.

Also provided are those methods wherein the cells are mouse cells.

Also provided are those methods, wherein the cells are in a mammal selected from the group consisting of: mouse, rat, guinea pig, dog, cat, monkey and human.

Also provided are those methods wherein the cells are human cells.

Methods to Diagnose, Prognose and Treat Patients are Provided Herein.

Included are methods to identify whether a cancer patient is a candidate for treatment with an sGCα1 -inhibiting composition, comprising identifying a patient having cancer cells that express sGCα1 as a candidate for treatment with a sGCα1-inhibiting composition.

Also provided are methods to diagnose whether a cancer patient has sGCα1-dependent cancer, comprising identifying a patient having cancer cells that express sGCα1 as a patient with sGCα1-dependent cancer.

Also provided are methods to predict the prognosis of a patient with cancer, comprising identifying a patient having cancer cells that express sGCα1 as having a poor prognosis.

Also provided are methods to inhibit tumor growth in a patient with an sGCα1-expressing cancer in need of such treatment, comprising administering at least one composition herein.

Also provided are methods to increase tumor regression in a patient with an sGCα1-expressing cancer in need of such treatment, comprising administering at least one composition herein.

Also provided are methods to inhibit tumor cell proliferation in a patient with an sGCα1-expressing cancer in need of such treatment, comprising administering at least one composition herein.

Also provided are methods to inhibit tumor cell metastasis in a patient with an sGCα1-expressing cancer in need of such treatment, comprising administering at least one composition herein.

Also provided are methods to treat a patient with an sGCα1-expressing cancer in need of such treatment, comprising administering at least one composition herein.

Also provided are methods to treat a patient with hormone-refractory prostate cancer in need of such treatment, comprising administering at least one composition herein.

Also provided are methods to treat a patient with metastatic prostate cancer in need of such treatment, comprising administering at least one composition herein.

Also provided are methods to treat a patient with late stage prostate cancer in need of such treatment, comprising administering at least one composition herein.

Also provided are methods to treat a patient with an sGCα1-expressing pancreatic cancer in need of such treatment, comprising administering at least one composition herein.

Also provided are methods to treat a patient with an sGCα1-expressing gastrointestinal cancer in need of such treatment, comprising administering at least one composition herein.

Also provided are methods to treat a patient with an sGCα1-expressing cancer in need of such treatment, comprising administering at least one composition herein, wherein the cancer is selected from the group comprising: neuroblastoma; lung cancer; bile duct cancer; non small cell lung carcinoma; hepatocellular carcinoma; lymphoma; nasopharyngeal carcinoma; ovarian cancer; head and neck squamous cell carcinoma; squamous cell cervical carcinoma; gastric cancer; colon cancer; uterine cervical carcinoma; gall bladder cancer; prostate cancer; breast cancer; testicular germ cell tumors; large cell lymphoma; follicular lymphoma; colorectal cancer; malignant pleural mesothelioma; glioma; thyroid cancer; basal cell carcinoma; T cell lymphoma; t(8;17)-prolyphocytic leukemia; myelodysplastic syndrome; pancreatic cancer; t(5;14)(q35.1;q32.2) leukemia; malignant fibrous histiocytoma; gastrointestinal stromal tumor; and hepatoblastoma; colorectal; endometrial; ovarian; gastric; and urothelial.

Also provided are methods of prophylactically treating cancer comprising administering to a subject in need of treatment an effective amount of at least one composition herein.

Kits for Research and Diagnostics are Provided Herein.

Included in the present invention are kits comprising: a volume a p53 regulator that disrupts sGCα1-p53 interaction; and instructions for the use of the volume of p53 regulator in the treatment of a sGCα1-expressing cancer in a subject. Specifically provided are those kits wherein the cancer is prostate cancer.

Also provided are kits for conducting an assay to predict recurrence of prostate cancer in a biological sample comprising: materials for detecting sGCα1. Specifically provided are kits comprising a peptide or nucleic acid herein as a biomarker.

Additional Methods and Compositions are Provided Herein.

Included are methods of identifying an anti-cancer agent, comprising: culturing a plurality of cancer cells capable of expressing sGCα1 and p53 in the presence of a test compound, and measuring p53 expression levels, wherein an increase in the p53 expression levels relative to a control is indicative of the test compound being an anti-cancer agent.

Also provided are methods of identifying an anti-prostate cancer agent, comprising: providing a test agent to a cell, and measuring the level of at least one p53 regulator associated with an altered expression levels in prostate cancer cells, wherein an altered level of a p53 regulator in the cell, relative to a control cell, is indicative of the test agent being an anti-prostate cancer agent.

Also provided are compositions comprising at least one peptide which mimics sGCβ1 heterodimerization domains which bind to and disrupts the pro-survival functions of sGCα1, thereby leading to cell death.

Also provided are compositions comprising Peptide A-8R—Ac-TFCKAFPFHII RRRRRRRR—OH [SEQ ID NO:1], or an isolated variant or biologically-active fragment thereof.

Also provided are peptides comprising A-8R [SEQ ID NO: 1] which are useful to kill hormone-refractory prostate cancer cells, or an isolated variant or biologically-active fragment thereof.

Also provided are methods for enhancing cell viability in a subject in need thereof, comprising inhibiting expression of sGCα1 in the cells.

Also provided are methods for sensitizing cells to apoptosis-inducing drugs in a subject in need thereof, comprising administering an effective amount of a composition which affect expression of sGCα1 in the cells.

Also provided are methods of determining the prognosis of a subject with prostate cancer, comprising: measuring the sGCα1 expression level in a test sample from the subject, wherein the sGCα1 expression level relative to control is associated with an adverse prognosis in prostate cancer.

Also provided are methods of predicting recurrence of prostate cancer comprising the steps of: obtaining a sample from a patient; and measuring sGCα1 expression levels in the sample; wherein sGCα1 expression levels above or below pre-determined cut-off levels are indicative of predict recurrence of prostate cancer.

Also provided are methods of determining patient treatment protocol comprising the steps of: obtaining a sample from a patient; and measuring the sGCα1 expression levels; wherein sGCα1 expression levels above or below pre-determined cut-off levels are sufficiently indicative of risk of recurrence to enable a physician to determine the degree and type of therapy.

Also provided are methods of treating a patient comprising the steps of: obtaining a sample from a patient; measuring sGCα1 expression levels in the sample to determine risk; and treating the patient with adjuvant therapy if they are a high risk patient. Specifically provided are those methods wherein a composition herein is used as a biomarker to determine sGCα1 expression levels.

Also provided are methods for treating cancer in a subject, comprising administering to the subject a polynucleotide encoding a functional A-8R gene product [SEQ ID NO:1]. Specifically provided are those methods wherein the cancer is prostate cancer.

Nucleic Acids, Constructs, Vectors, Cells and Transgenic Animals are Provided.

Included in the present invention are isolated nucleic acids comprising a nucleic acid encoding an amino acid having the sequence TFCKAFPFHII [SEQ ID NO: 5].

Also provided are isolated nucleic acids comprising a nucleic acid encoding an amino acid having the sequence of A-8R [SEQ ID NO: 1].

Also provided are isolated nucleic acids comprising a nucleic acid encoding an amino acid having the sequence of B-8R [SEQ ID NO: 2]. Specifically provided are those nucleic acids herein, which further comprises a promoter operatively linked to the nucleic acid. Specifically provided are vectors comprising a nucleic acid herein. Specifically provided are cells comprising a vector herein. Specifically provided are transgenic mammals comprising a cell herein.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE FIGURES

The patent or application file may contain one or more drawings executed in color and/or one or more photographs. Copies of this patent or patent application publication with color drawing(s) and/or photograph(s) will be provided by the Patent Office upon request and payment of the necessary fee.

FIGS. 1A-1F: Over-expression of sGCα1 inhibits p53 transcriptional activity. p53 activity was quantified by measuring luciferase activity. Bar graphs represent the average of three independent experiments plus standard deviation. All cells received the same amount of transfected expression plasmid and that pCH110 was used to control transfection efficiency. Student T test showed significant differences ($P<0.04$), as indicated:

FIG. 1A: LNCaP cells were transfected with 0.1 μg p53-Luc reporter plasmid, with or without 0.5 μg p53, 0.5 μg pCH110, and 0.1 or 0.5 μg sGCα1.

FIG. 1B: LNCaP were transfected with 50 nM sGCα1 siRNA, and 24 hrs later with 0.1 μg p53-Luc reporter plasmid and 0.5 μg pCH110.

FIG. 1C: LNCaP cells were transfected with 50 nM control or sGCα1 siRNA and Western blotting was used to detect expression of sGCα1 and p53. β-actin expression was used to standardize Western blot.

FIG. 1D: LNCaP cells were transfected with 0.5 μg empty vector or sGCα1 and Western blotting was used to detect sGCα1 and p53 expression. β-actin expression was used to standardize Western blot.

FIG. 1E: VCaP cells were transfected with 0.1 μg p53-Luc reporter plasmid, with or without 0.5 μg p53, 0.5 μg pCH110, and 0.1 or 0.5 μg sGCα1.

FIG. 1F: PC-3 Cells were transfected with 0.1 μg p53-Luc, 0.5 μg pCH110, 0.5 μg p53, and 0.1 or 0.5 μg sGCα1. p53 transcriptional activity was measured by luciferase assay. Asterisks indicate statistical significance ($P<0.05$).

FIG. 2A: Cells were transfected with 0.5 μg pCH110, 0.1 μg p53-Luc reporter plasmid, and subjected to 5 or 50 mM ODQ.

FIG. 2B: Cells were transfected with 0.5 μg p53 and 0.5 μg sGCα1 and/or sGCβ1.

FIG. 2C: Cells were treated with different concentrations of C-PTIO.

FIG. 2D: Cells were treated with different concentrations of SNP.

FIG. 2E: Cells were treated with different concentrations of 8-Br-cGMP.

FIG. 2F: Cells were transfected with 0.5 or 1 µg sGCα1 or sGCα1(D531A). Bar graphs represent averages of three independent experiments plus standard deviations. All activities are relative to the first condition, and this activity was set to 1. All cells received the same amount of transfected expression plasmid and that pCH110 was used to control transfection efficiency. Student T test showed significant differences (P<0.04), as indicated.

FIG. 3A-3B: Cytoplasmic extracts were prepared from LNCaP cells and subjected to immunoprecipitation using an anti-p53 (FIG. 3A) or anti-sGCα1 antibody (FIG. 3B). Western blotting was used to detect p53 and sGCα1. The negative control IP was performed using an IgG antibody. "Input" represents extracts that were used in the IP experiments, while whole-cell extracts were positive controls for the Western blotting.

FIG. 3C: LNCaP cytoplasmic extract was fractionated through a Sephacryl S-300 gel filtration column using HPLC. 2-ml fractions were collected and analyzed by Western blotting using either an anti-sGCα1 (Cayman Chemical) or anti-p53 (Santa Cruz Biotechnology) antibody.

FIG. 3D: LNCaP cells were subjected to immunocytochemistry using anti-sGCα1 or anti-p53 antibody to measure subcellular localization of endogenous proteins. Images were viewed by confocal microscopy.

FIG. 3E: Nuclear (N) and cytosolic (C) extracts were prepared from LNCaP cells and Western blotting was used to measure protein levels of p53, sGCα1, the exclusively nuclear hRARα, and the cytosolic protein MLK3. β-actin was used as loading control.

FIG. 4A: LNCaP cells were infected with a control empty adenovirus or sGCα1-expressing virus (20 MOI of each) and nuclear and cytosolic extracts were prepared. These extracts were subjected to Western blotting to detect sGCα1. Whole Cell Input represents total amount of cellular p53 before cell fractionation. β-actin was used as loading control.

FIG. 4B: Nuclear (N) and cytosolic (C) extracts were prepared from LNCaP cells and Western blotting was used to measure protein levels of MDM2, p53, JAB1, and sGCα1. β-actin was used as loading control.

FIG. 4C: LNCaP cells were untransfected (upper panel) or transfected with sGCα1 siRNA (lower panel) and measured for subcellular localization of endogenous sGCα1 or p53 using antibodies against these two protein anti-p53 antibody. Images were viewed by confocal microscopy.

FIG. 6F –sGCα1 affects the expression of p53-regulated genes involved in apoptosis. LNCaP cells were infected with empty adenovirus or adenovirus expressing sGCα1 and subjected to a p53 Signaling PCR array from Superarray. Shown are fold-changes in expression in p53-regulated genes p53AIP1, PCBP4, and BIRC5 in sGCα1-over-expressing cells as compared to cells infected with empty virus.

FIG. 9A: RT-PCR was used to measure the expression of p53, sGCα1, and GAPDH mRNAs. Note that GAPDH was used as an internal control.

FIG. 9B: Three PCR products, ranging in size from 423 to 708 bp, were synthesized to cover the entire coding region of p53.

FIG. 9C: Two PCR products, 360 and 460 bp, were synthesized to cover the central part of the p53 coding region.

FIG. 12A: The amino acid sequences of four synthetic peptides, Peptide A-D, fused to an 8-Arginine tag [SEQ ID NOS 1-4, respectively, in order of appearance] for membrane translocation, are shown. Note that these four peptide sequences mimic four known sGCβ1 dimerization domains with sGCα1.

FIG. 12B: LNCaP cells were grown without androgen for 2 or 4 days in the presence of increasing concentration of Peptide A-8R [SEQ ID NO: 1] (upper left), Peptide B-8R [SEQ ID NO: 2] (upper right), Peptide C-8R [SEQ ID NO: 3] (lower left), or Peptide D-8R [SEQ ID NO: 4] (lower right). The MTT reagent was used to measure cell density.

FIG. 13A: LNCaP cells were grown with (Right) or without (Left) 1 nM androgen (R1181) for 3 or 6 days in the presence of increasing concentration of Peptide A-8R [SEQ ID NO: 1] or vehicle (70% DMSO). The MTT reagent was used to measure cell density.

FIG. 13B: LNCaP cells were grown with (Right) or without (Left) 1 nM androgen (R1881) for 3 or 6 days in the presence of increasing concentration of Peptide C-8R [SEQ ID NO: 3] or vehicle and then cell density was measured.

FIG. 14A: LNCaP cells were grown with (Right) or without (Left) 1 nM R1881 for 3 or 6 days in the presence of increasing concentration of Peptide A or vehicle and then cell density was measured.

FIG. 14B: LNCaP cells were grown with (Right) or without (Left) 1 nM R1881 for 3 or 6 days in the presence of increasing concentration of Peptide A-8R [SEQ ID NO: 1] or vehicle and then cell density was measured.

FIG. 15A: LNCaP cells were grown for 1-8 hrs in the presence of 10 μM Peptide A-8R [SEQ ID NO: 1] or vehicle and then cell density was measured.

FIG. 15B: C81 (androgen-refractory LNCaP) cells were grown for 1-8 hrs in the presence of 10 μM Peptide A-8R [SEQ ID NO: 1] or vehicle and then cell density was measured.

FIG. 15C: CWR22-Rv1 (androgen-refractory) cells were grown for 1-8 hrs in the presence of 10 μM Peptide A-8R [SEQ ID NO: 1] or vehicle and then cell density was measured.

FIG. 16A: LNCaP, C81, and CWR22-Rv1 cells were grown in the absence or presence of 1 nM R1881 for two days and then measured for sGCα1 protein expression by Western blotting.

FIG. 16B: LNCaP, PC-3, Cos, and ACHN cells were grown for two days and then measured for sGCα1 protein expression by Western blotting.

FIG. 17A: PC-3 prostate cancer cells were grown for 3 or 6 days in the presence of increasing concentration of Peptide A-8R [SEQ ID NO: 1] or vehicle and then cell density was measured.

FIG. 17B: Cos monkey kidney cancer cells were grown for 2 or 4 days in the presence of increasing concentration of Peptide A-8R [SEQ ID NO: 1] or vehicle and then cell density was measured.

FIG. 17C: ACHN human kidney cancer cells were grown for 2 or 4 days in the presence of increasing concentration of Peptide A-8R [SEQ ID NO: 1] or vehicle and then cell density was measured.

FIG. 18A: LNCaP cells were grown for 1-24 hrs in the presence of vehicle, 10 mM Peptide A-8R [SEQ ID NO: 1], or 20 mM Etoposide and then measured for Caspase 3/7 activity.

FIG. 18B: LNCaP cells were grown for 4 hrs in the presence of increasing concentration of Peptide A-8R [SEQ ID NO: 1] with or without 40 mM Z-VAD-FMK and then cell density was measured.

FIG. 19A: LNCaP prostate cancer cells were grown in the presence of 25 mM Peptide A-8R-Biotin [SEQ ID NO: 1] and subjected to immunocytochemistry using an anti-sGCα1 antibody (green) or anti-Biotin antibody (red). DAPI was used to stain nuclei.

FIG. 19B: LNCaP whole cell extract was incubated with 100 mg Peptide A-8R-Biotin [SEQ ID NO: 1] for 4 hrs and then subjected to purification using streptavidin-agarose beads. As a negative control, the purification was repeated with extract alone (no Peptide A-8R-Biotin [SEQ ID NO: 1]).

FIG. 19C: LNCaP cells were grown with for 12 or 48 hrs in the presence of increasing concentration of Peptide A-8R [SEQ ID NO: 1] (Left) or PeptideA-8R-Biotin [SEQ ID NO: 1] (Right) and then cell density was measured.

FIG. 21A: RT-PCR was used to measure the expression of sGCα1, sGCβ1, p53, and GAPDH mRNAs. Note that GAPDH was used as an internal control.

FIG. 21B: Capan-2 pancreatic cancer cells were grown for 3 or 5 days in the presence of increasing concentration of Peptide A-8R [SEQ ID NO: 1] or vehicle and then cell density was measured.

FIGS. 28A-C: Peptide A-8R [SEQ ID NO: 1] inhibits the growth of C81 prostate xenograft tumors. (A) C81 (hormone-independent LNCaP) xenograft tumors were grown in nude mice to a size of about 200 cubic mm and then treated every other day with five intratumoral injections of either Peptide A-8R [SEQ ID NO: 1] (40 mm/kg of animal) or vehicle (DMSO) for seven days, after which the tumors were left untreated and allowed to grow for an additional 3 weeks before the tumors were excised. Each point represents the average tumor size of three animals plus or minus the standard deviations. The arrow represents the last treatment of Peptide A-8R [SEQ ID NO: 1] or vehicle. There is a statistical significance ($P<0.0004$) of Peptide A activity, relative to vehicle, for each treatment day. (B) Upper panel shows images of the excised tumors from the Peptide A-8R [SEQ ID NO: 1]-treated or vehicle-treated animals, and lower panel shows the average weight of these tumors. Bar graphs represent averages of each set of three tumors plus standard deviations. Asterisks indicate statistical significance ($P<0.02$). (C) Image showing the strong anti-tumor effect of Peptide A-8R [SEQ ID NO: 1], as compared to vehicle control, in one animal.

DETAILED DESCRIPTION

Definitions

Figure 1A:
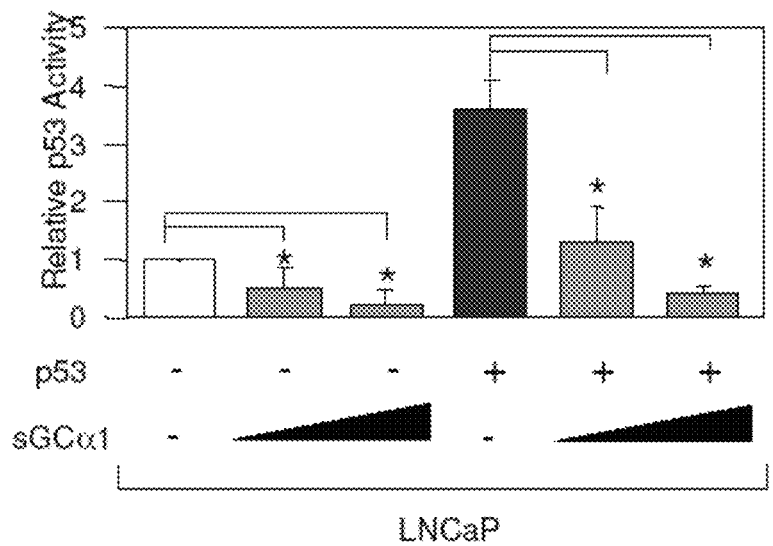

For convenience, certain terms employed in the specification, examples, and appended claims are collected here, before further description of the invention. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used to refer to one or to more than one (i.e., to at least one) of the grammatical object of the article. By way of example, "an element" means one element or more than one element.

The term "plurality" means more than one.

The terms "comprise" and "comprising" are used in the inclusive, open sense, meaning that additional elements may be included.

The term "including" is used to mean "including but not limited to". "Including" and "including but not limited to" are used interchangeably.

The term "8R" as used herein refers to the sequence of 8 arginines, or RRRRRRRR [SEQ ID NO. 6].

General Description

Androgen signaling is mediated by the androgen receptor (AR), whose transcriptional activity correlates with a higher risk and a higher grade of prostate cancer. This androgen dependency of early-stage prostate cancer is used to combat this disease with anti-androgen therapy. During the initial 1-2 years of the disease, the cancer is androgen-sensitive and thus responds to androgen-ablation therapy. However, upon its recurrence, the cancer is androgen-insensitive such that androgen-ablation therapy fails to work. Importantly, functional AR is found in most prostate cancer cells, including late-stage cells that become androgen-independent.

Androgen-regulated genes involved in prostate cancer cellular proliferation that may make potentially good therapeutic targets are described herein. Utilizing a gene micrarray approach with two prostate cancer cell lines that respond oppositely to the growth-promoting effects of androgens, the gene encoding soluble guanylyl cyclase alpha 1 (sGCα1) has been identified. sGCα1 is one subunit of sGC, a heterodimeric enzyme that catalyzes cGMP synthesis in response to nitric oxide. This signaling pathway is very important in mammalian physiology, particularly in the cardiovascular system. sGCα1 expression is androgen-regulated, is required for prostate cancer proliferation, and increases with increasing grade of prostate cancer.

sGCα1 can interact with cytoplasmic p53 and negatively regulate its transcriptional activity. The p53 protein acts as a tumor suppressor, and is able to disrupt the growth process of cells by slowing the cell cycle or inducing apoptosis. The p53 gene is the most commonly mutated locus in human cancers. While mutations at the p53 locus represent a common mechanism of p53 inactivation, there are at least half of human cancers that do not harbor such mutations. Indeed, in prostate cancer, p53 mutations are observed in late-stage disease and the mutation rate varies from 3% to 42%. Additional mechanisms are required to overcome or bypass the wild-type p53 protein in the more than half of tumors that express this protein.

The sGCα1 inhibition of p53 represents a mechanism for down-regulation in those 50% or so of prostate tumors that express wild-type p53 protein.

In many aspects of the present invention, nucleic acids and amino acid sequences are disclosed. Those in the art are aware of the redundancy of the genetic code, and therefore, any nucleic acid which encodes for the amino acids herein are described as within the scope of the present invention. Moreover, conserved amino acid residue changes in the present amino acid compounds are also within the scope of the present invention, as are the corresponding nucleic acid changes and resulting nucleic acid sequences. These concepts are available in Alberts et al., Molecular Biology of the Cell, Fourth Edition (2002, Garland Science)

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference herein.

Example I

First, as shown in FIG. 1A, transient transfection of sGCα1 in LNCaP cells led to a dose-dependent inhibition of p53 transactivation. Diminution of endogenous sGCα1 expression resulted in a small, but reproducible increase in p53 activity (FIG. 1B). Together, these results show that both endogenous and exogenous sGCα1 can inhibit p53 activity. Significantly, this negative effect is not unique to LNCaP cells, as it was also observed in VCaP cells (FIG. 1E) and, importantly, the androgen-independent lines C81, CWR22-Rv1, and Mda-P109 (data not shown).

FIG. 1C is a graph showing the results where LNCaP cells were transfected with 50 nM control or sGCα1 siRNA and Western blotting was used to detect expression of sGCα1 and p53. β-actin expression was used to standardize Western blot.

Figure 1D:
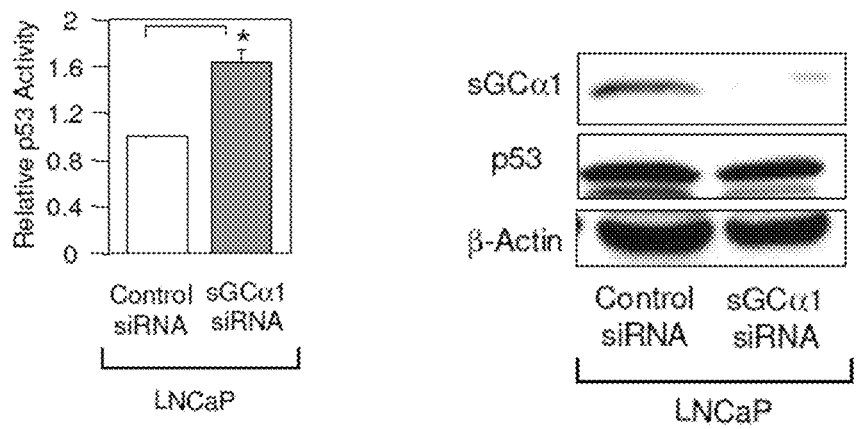
Figure 1D:
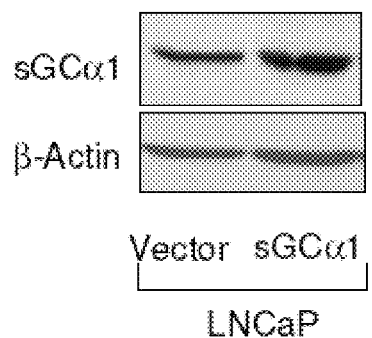
Figure 1E:
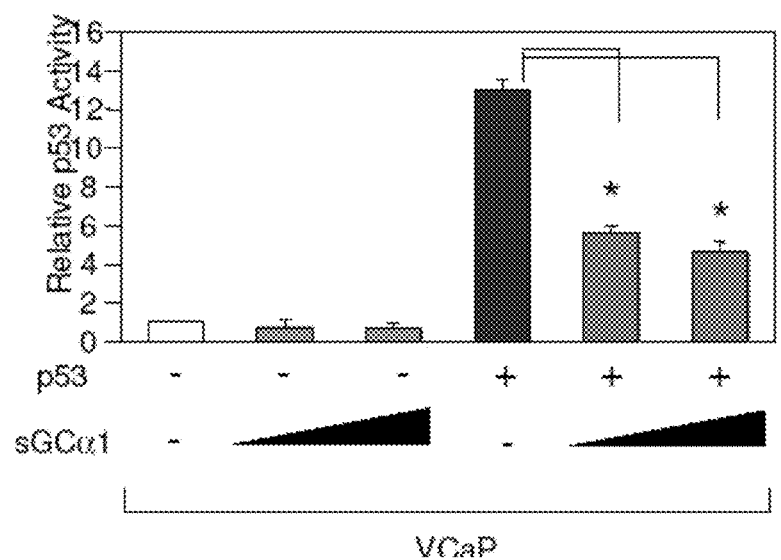

FIG. 1D is a graph showing the results where LNCaP cells were transfected with 0.5 μg empty vector or sGCα1 and Western blotting was used to detect sGCα1 and p53 expression. β-actin expression was used to standardize Western blot.

Figure 1F:
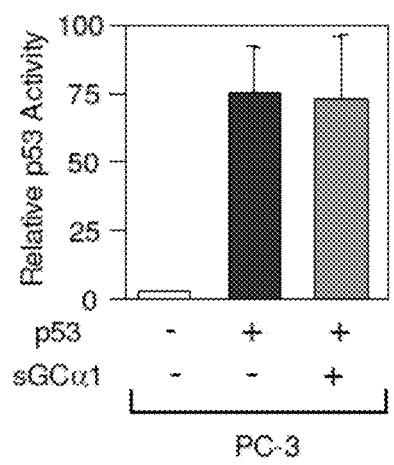

FIG. 1F is a graph showing the results where PC-3 Cells were transfected with 0.1 μg p53-Luc, 0.5 μg pCH110, 0.5 μg p53, and 0.1 or 0.5 μg sGCα1.

Figure 2A:
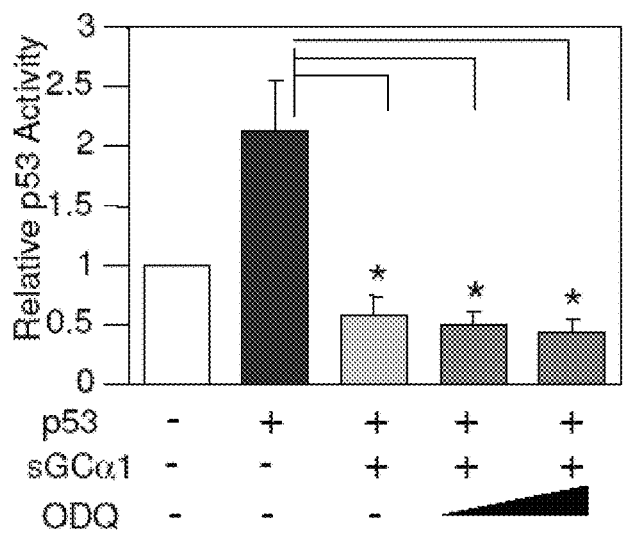
FIGS. 2A-2F: The sGCα1-mediated repression of p53 transcriptional activity is independent of mediators of NO signaling and guanylyl cyclase activity. Androgen-dependent LNCaP cells were transfected with 0.5 μg pCH110, 0.1 μg p53-Luc reporter plasmid, and subjected to different treatments.
Figure 2B:
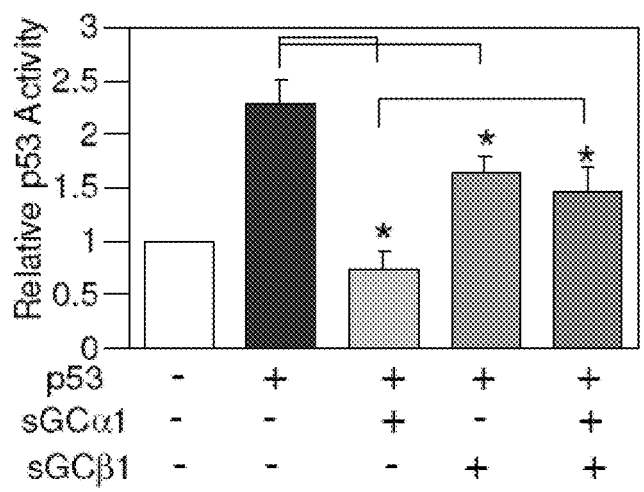

To determine whether nitric oxide (NO) signaling is involved in sGCα1-mediated repression of p53 transcriptional activity, NO interfering drugs were used. As shown in FIG. 2A, ODQ, which inhibits sGC enzyme activity, had no effect on sGCα1-mediated repression of p53, even though these two concentrations strongly inhibited sGC-catalyzed cGMP synthesis (data not shown), showing that sGCα1 inhibits p53 activity independent of sGC enzyme activity. These data show that transfected sGCβ1 disrupts, rather than mediates, the negative activity of transfected sGCα1 on p53 (FIG. 2B), thus showing that the sGCα1 inhibitory activity is independent of sGCβ1.

Figure 2C:
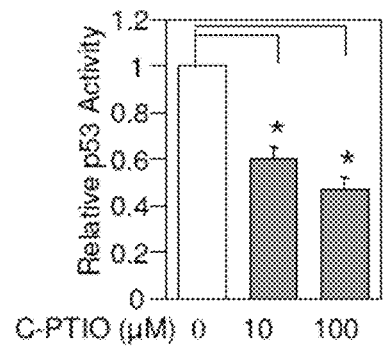

C-PTIO is an NO scavenger and thus would be expected to enhance p53 activity if sGCα1 requires NO for its inhibitory activity; contrary to this, c-PTIO inhibit p53 activity of 100 nM of drug (FIG. 2C), suggesting that NO is not involved in sGCα1 inhibition.

Figure 2D:
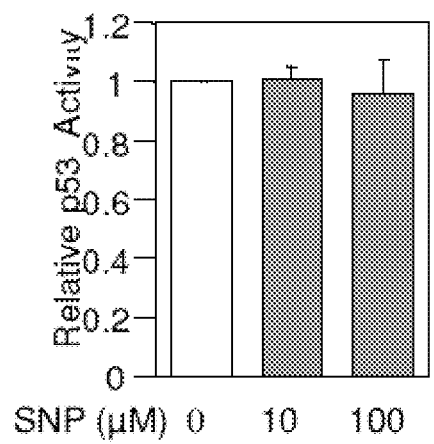
Figure 2E:
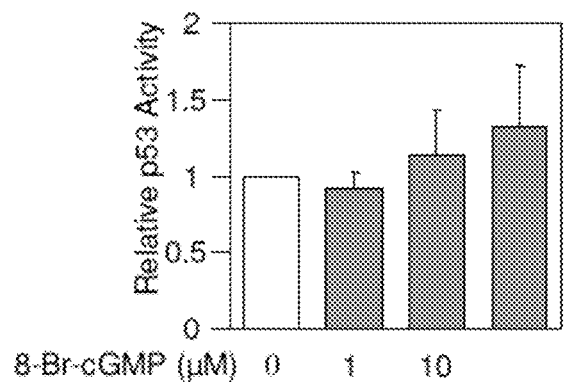

Supporting this finding, the NO donor SNP had no effect (FIG. 2D). 8-Br-cGMP did not repress but, in fact, weakly enhanced p53 transcriptional activity (FIG. 2E), implying that the second messenger of NO signaling in sGCα1 repression of p53. Collectively, these results now show that the sGCα1 effect on p53 occurs independent of NO signaling.

Figure 2F:
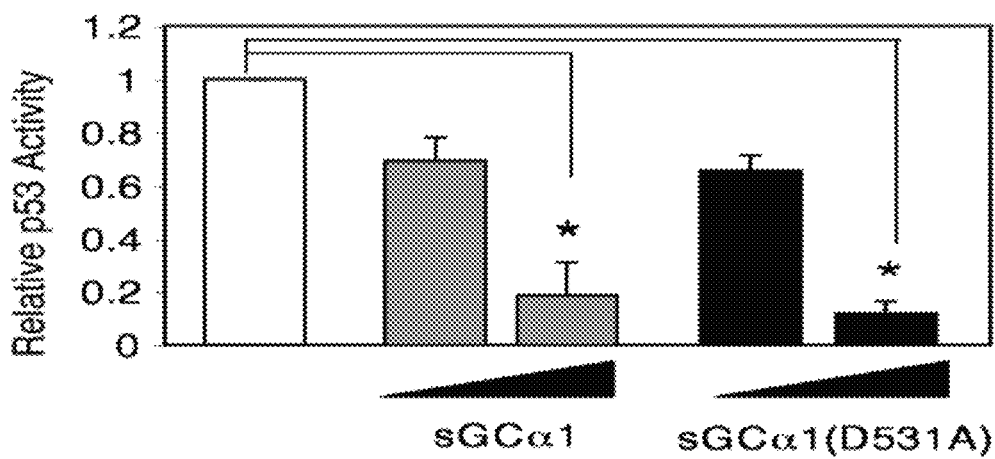

The mutant sGCα1(D531A), which has greatly reduced cyclase activity (data not shown), is fully able to inhibit p53 transcriptional activity (FIG. 2F), demonstrating that sGCα1 activity on p53, as on proliferation (data not shown), does not depend on its guanylyl cyclase activity.

Figure 3A:
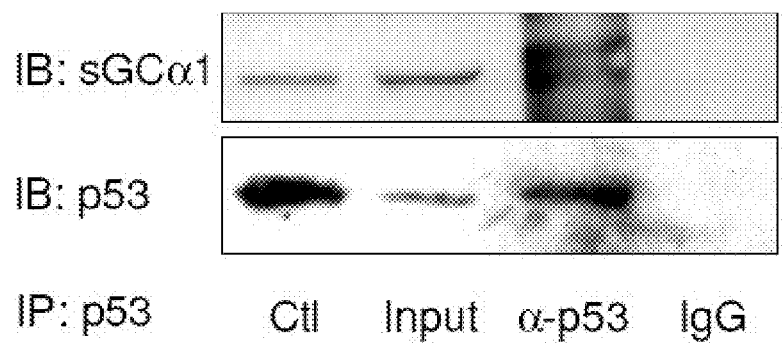
FIGS. 3A-3E: Endogenous sGCα1 associates with p53 in LNCaP cells.
Figure 3B:
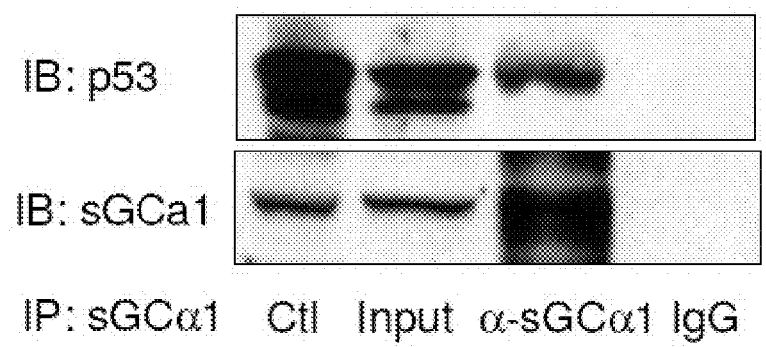
Figure 3C:
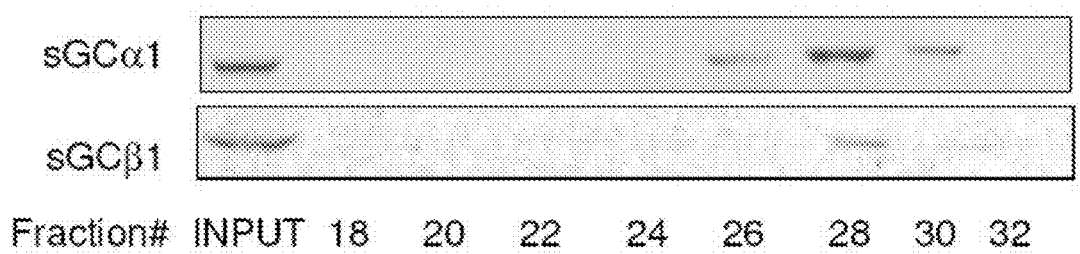
Figure 3D:
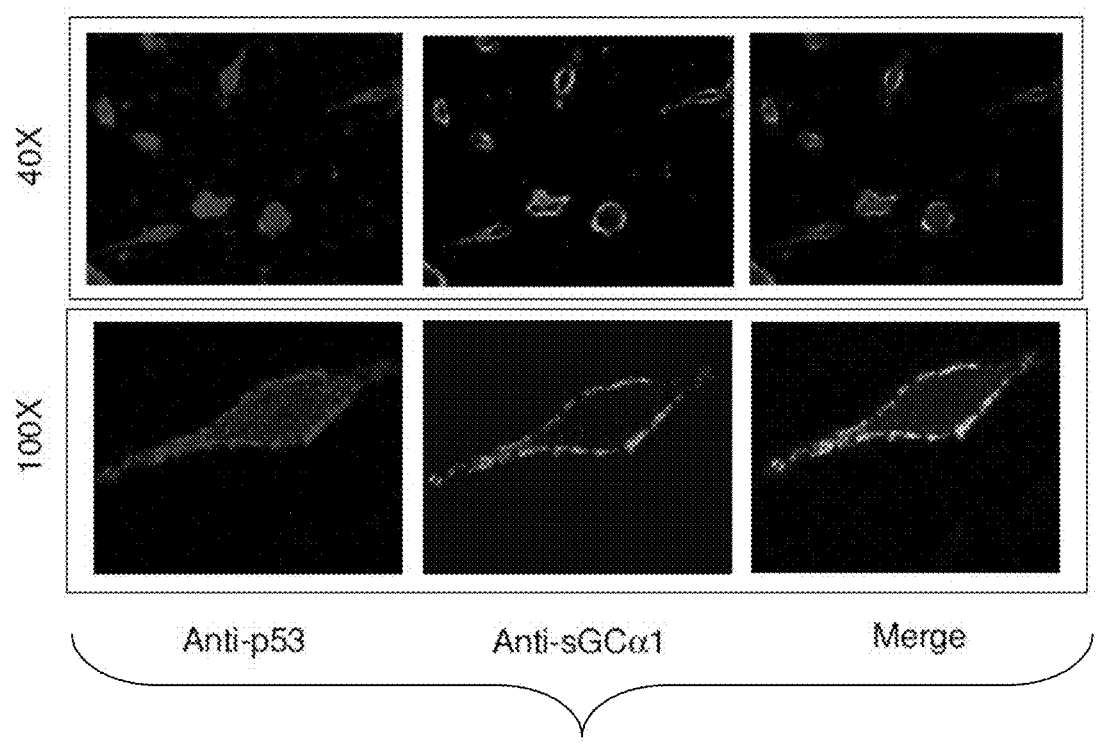

To determine if there is a physical association between sGCα1 and p53, IP experiments were performed with endogenous proteins found in LNCaP cells. When p53 was immunprecipitated, endogenous sGCα1 protein was co-purified (which was not seen with a negative control immunoprecipitation (IP) (nonspecific IgG) (FIG. 3A)). A complementary IP showed that endogenous p53 co-purified with endogenous sGCα1 (FIG. 3B). Interestingly, when an LNCaP cytoplasmic extract was run on a gel filtration FPLC column, sGCα1 and p53 are found in the same elution fractions (FIG. 3C). To determine if such a complex exists in cells, immunocytochemistry was used to visualize sGCα1 and p53. This showed that endogenous p53 is localized in both the nucleus and cytoplasm, while sGCα1 is exclusively cytoplasmic (FIG. 3D). Interestingly, cytoplasmic p53 is co-localized with sGCα1 (FIG. 3D). An amplified image of a single cell showed that most of the endogenous sGCα1 and cytoplasmic p53 are localized together (FIG. 3D).

Figure 3E:
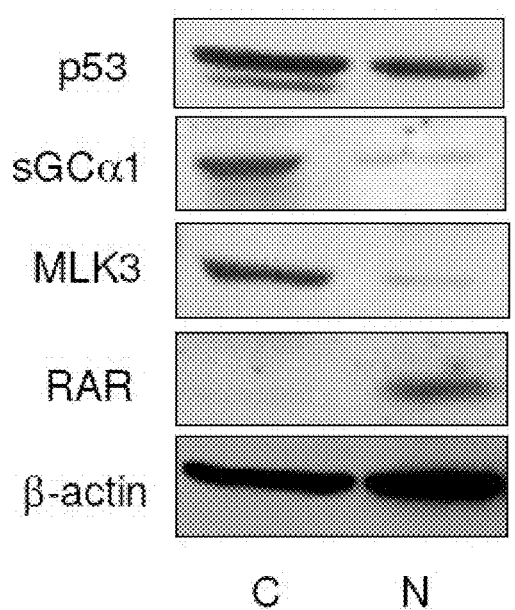

Western blotting has excluded the possibility that this cytoplasmic sequestration leads increased p53 protein degradation, since altering endogenous sGCα1 levels by siRNA transfection or adenovirus expression did not alter the p53 protein levels (data not shown). In addition, LNCaP cell fractionation experiments showed that more p53 is found in the cytoplasmic fraction than nuclear fraction (FIG. 3E), in support of the immunocytochemisty results. These data show that sGCα1 may inhibit p53 transcriptional activity by mediating cytoplasmic sequestration of this tumor suppressor.

Figure 4A:
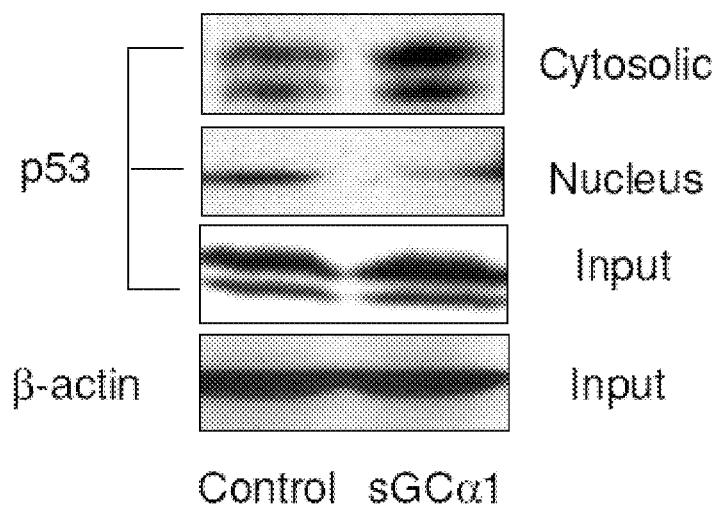
FIGS. 4A-4C: sGCα1 regulates the subcellular localization of p53.
Figure 4B:
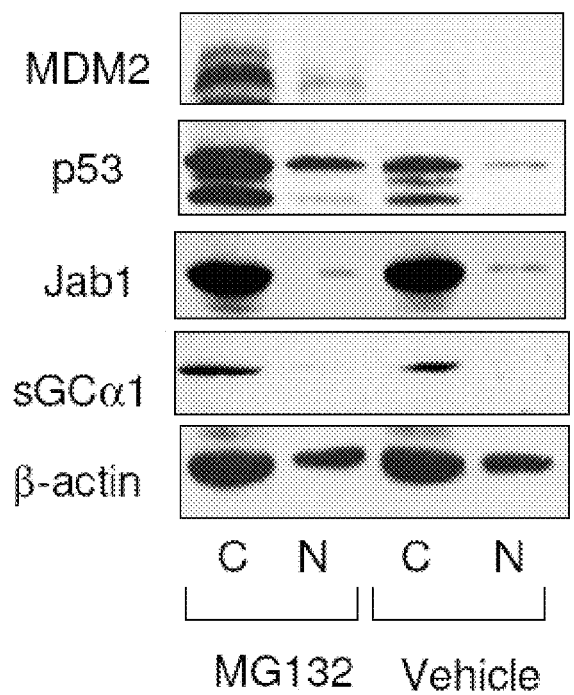

LNCaP cells were infected with an sGCα1-expressing adenovirus or control empty virus and p53 subcellular localization was measured by Western blotting following cell fractionation. As shown in FIG. 4A, adenovirus over-expression of sGCα1 led to higher cytosolic and lower nuclear levels of p53 protein, as compared to empty virus. Western blotting showed no detectable expresssion for MDM2 and significant cytoplasmic expression of Jab1, two proteins known to be involved in p53 nuclear export (FIG. 4B). Treatment of cells with the proteasome inhibitor MG132 significantly enhanced MDM2 cytoplasmic levels (FIG. 4B), suggesting that this protein is under active proteasome-dependent degradation.

Figure 4C:
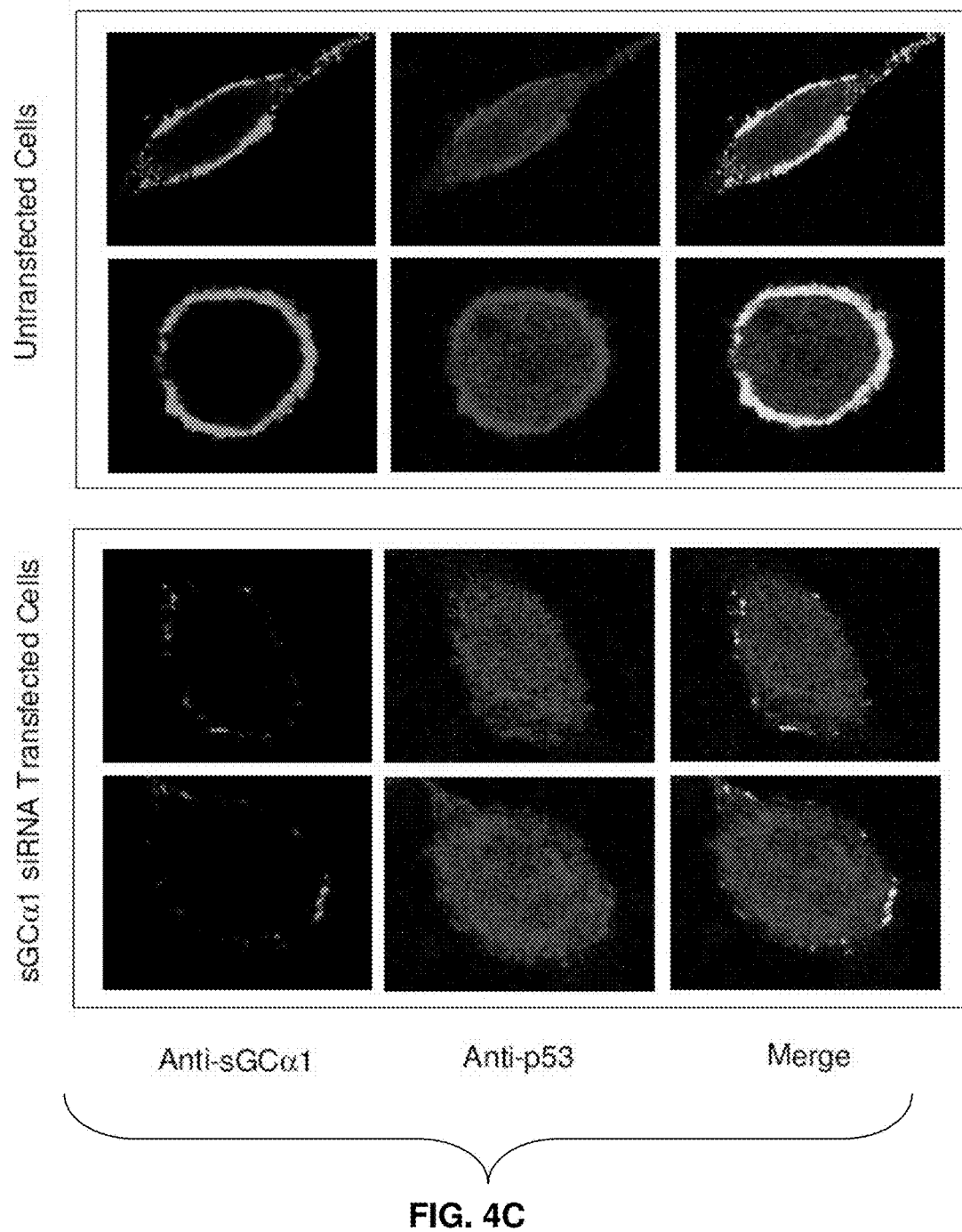

To confirm the cell fractionation data (see FIG. 4A), a complementary approach was used in which LNCaP cells were transfected with sGCα1 siRNA and protein expression and subcellular localization were monitored by immunocytochemistry. As observed previously (see FIG. 3D), endogenous sGCα1 is exclusively cytoplasmic in LNCaP cells and co-localizes with cytoplasmic p53 (FIG. 4C). These sGCα1 levels are greatly diminished following siRNA transfection, and importantly, this coincides with an almost complete elimination of cytoplasmic p53 (FIG. 4C). These results together show that sGCα1 is responsible for cytoplasmic sequestration of p53 in prostate cancer cells.

Figure 5A:
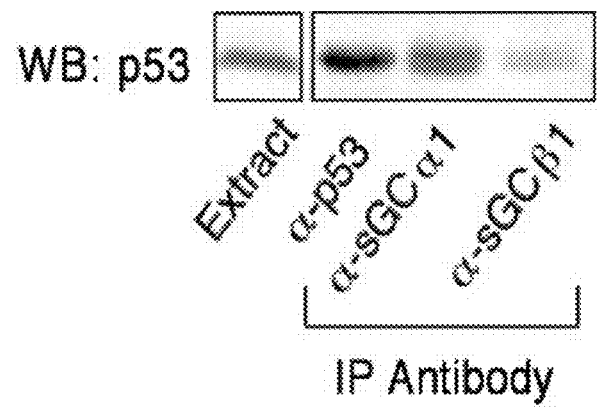
FIGS. 5A-5C: E. coli-expressed sGCα1 and p53 interact in vitro. Cell extracts were prepared from BL21 cells transformed with sGCα1, p53, or sGCβ1. 500 µl of each extract were mixed and subjected to immunoprecipitation using an anti-sGCα1 antibody (Cayman Chemical) or anti-p53 antibody (Santa Cruz Biotechnology), or anti-sGCβ1 antibody (Cayman Chemical). Western blotting was used to measure the levels of (FIG. 5A) p53, (FIG. 5B) sGCα1, and (FIG. 5C) sGCβ1. Note that PBS was used to wash the Protein A-sepharose beads in the IP reactions. Extract represents bacterial extract before subjected to immunoprecipitation.

The data in FIG. 3 and FIG. 4 show that endogenous sGCα1 and p53 can co-associate in LNCaP cells. To determine if the sGCα1-p53 interaction is direct, the inventors have expressed the proteins in E. coli and carry out IP experiments. As shown in FIG. 5A, an anti-p53 antibody can IP p53 from E. coli extract.

Figure 5B:
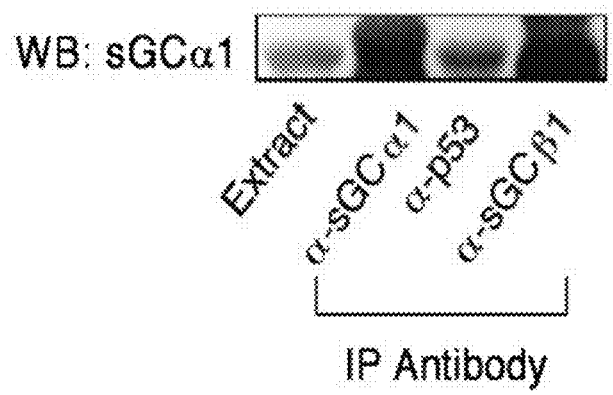

When p53 and sGCα1 are mixed and an IP is performed using an anti-sGCα1 antibody, p53 is co-purified (FIG. 5A) showing that p53 and sGCα1 expressed in E. coli can associate with one another. As a control, p53 and sGCβ1 extracts were mixed and subjected to an IP with an anti-sGCβ1 antibody, yielding substantially less co-purified p53 (FIG. 5A). When sGCα1 was measured, the results show that sGCα1 can come down, as expected with anti-sGCα1 IP, and with an anti-p53 IP (FIG. 5B), confirming the sGCα1-p53 interaction. An anti-sGCβ1 IP can pull-down substantial levels of sGCα1 (FIG. 5B).

Figure 5C:
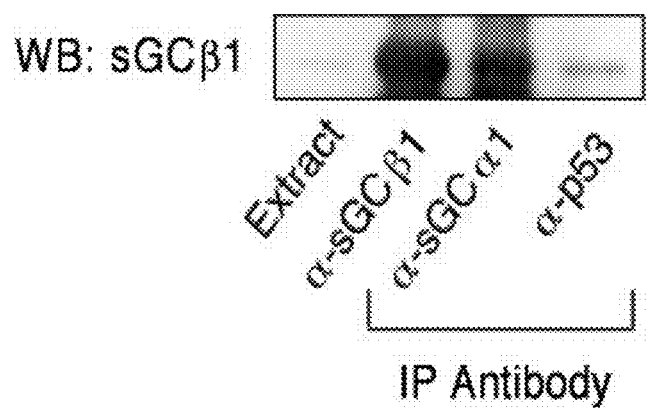

Monitoring sGCβ1 levels showed that this protein can co-IP with sGCα1 very strongly, and only weakly with p53 (FIG. 5C), demonstrating that sGCβ1 associates much more strongly with sGCα1 than with p53. Collectively, these data show that E. coli-expressed p53 and sGCα1 can interact with one another, confirming the experiments in LNCaP cells (see FIG. 5) and thus showing that this interaction is direct.

To determine if sGCα1-mediated inhibition of p53 affects p53-regulated gene expression, a PCR array analysis was performed using a p53 Signaling Array (from Superarray). LNCaP cells were transfected with sGCα1 siRNA (FIG. 6E), which results in enhanced p53 transactivation (see FIG. 1B), and subjected to PCR array analysis.

Figure 6A:
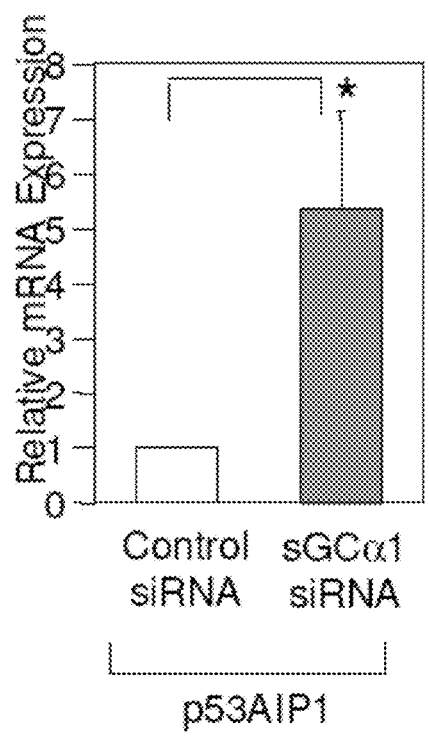
FIGS. 6A-6F: sGCα1 affects the expression of p53-regulated genes in prostate cancer cells. LNCaP cells were transfected with 50 nM control or sGCα1 siRNA and QRT-PCR was used to measure the expression of (FIG. 6A) p53AIP1, (FIG. 6B) PCBP4, (FIG. 6C) Survivin, (FIG. 6D) p21, and (FIG. 6E) sGCα1, relative to GAPDH. Bar graphs represent averages of three independent experiments plus standard deviations. All activities are relative to control siRNA transfection, and this activity was set to 1. Student T test showed significant differences (P<0.02), as indicated.
Figure 6B:
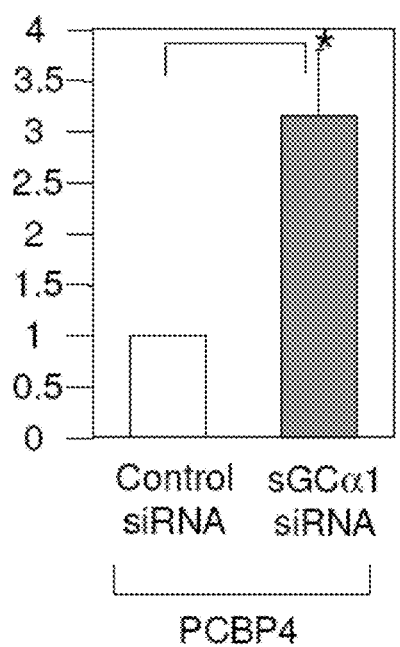
Figure 6C:
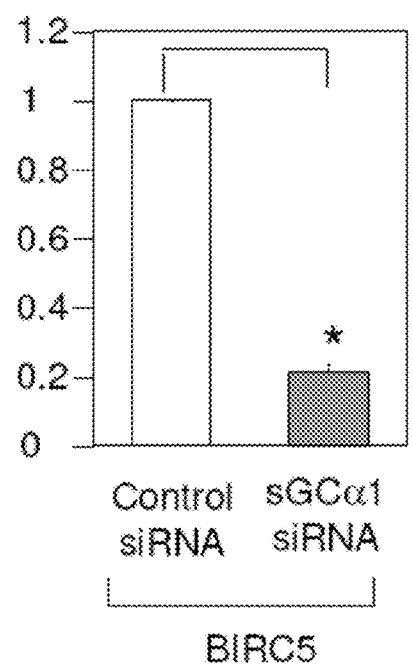
Figure 6D:
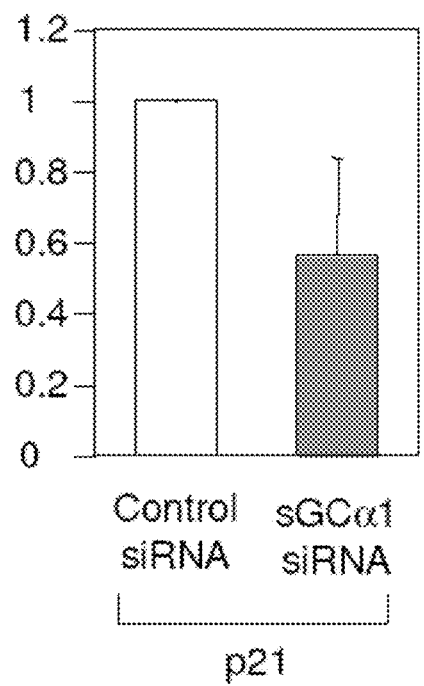

Among the 84 genes on the array, only three exhibited differential expression in response to siRNA-mediated diminution of sGCα1, showing that the sGCα1 role on p53-regulated gene expression is gene-specific, not global.

sGCα1 over-expression reduced, but did not eliminate, nuclear p53 protein (see FIG. 4A). These genes are p53AIP1 and PCBP4, two p53-induced genes mediating apoptosis, and Survivin (or BIRC5), a p53-repressed gene that protects cells from apoptosis. The PCR array data were verified by quantitative real-time-PCR (QRT-PCR) (FIGS. 6A-6C). Interestingly, p53-regulated genes involved in other p53-mediated pathways, including cell proliferation, were not affected by sGCα1 siRNA, and this is shown for p21 (FIG. 6D), showing that sGCα1 may be a specific inhibitor of p53 activity in apoptosis.

Figures 6E, 6F:
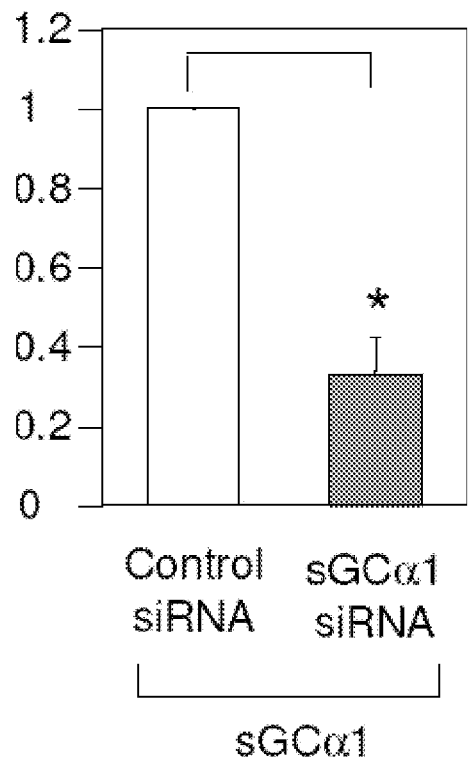

FIG. 6F shows that sGCα1 affects the expression of p53-regulated genes involved in apoptosis. LNCaP cells were infected with empty adenovirus or adenovirus expressing sGCα1 and subjected to a p53 Signaling PCR array from Superarray. Shown are fold-changes in expression in p53-regulated genes p53AIP1, PCBP4, and BIRC5 in sGCα1-over-expressing cells as compared to cells infected with empty virus.

Figure 7A:
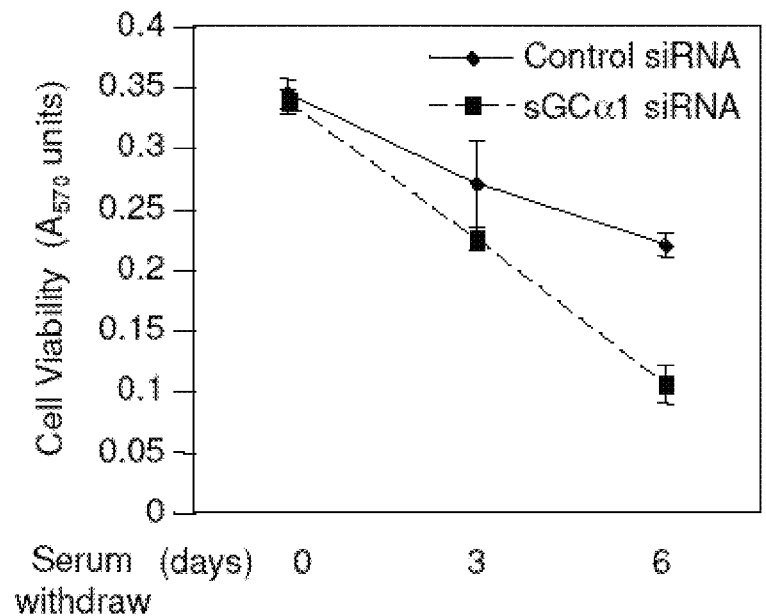
FIG. 7A: Viability of prostate cancer cells is affected by sGCα1 expression. LNCaP cells were transfected with control siRNA or sGCα1 siRNA and grown for 0, 3, or 6 days in the absence of serum. Cell number was measured using the MTT assay. Each data point represents averages of three independent experiments plus standard deviations.
Figure 7B:
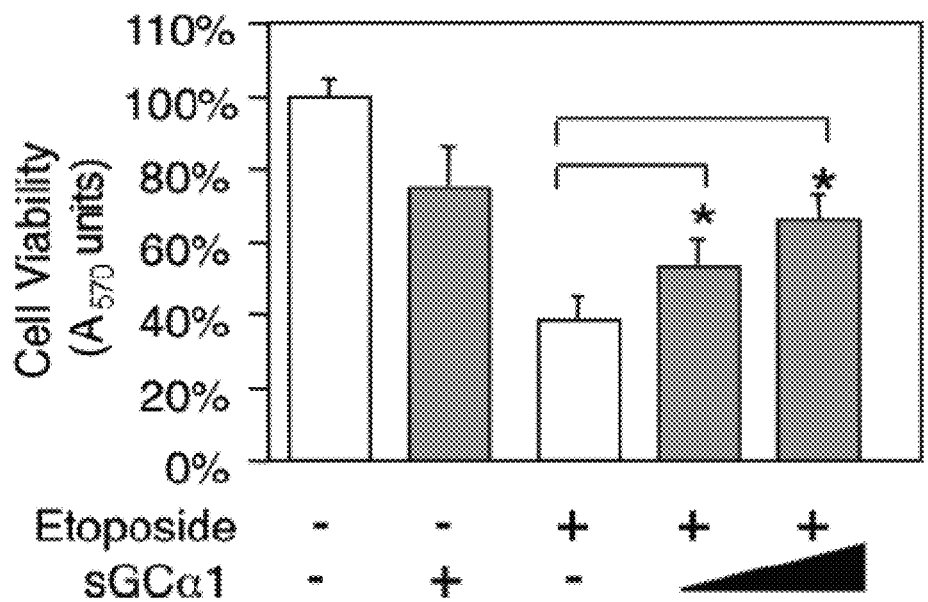
FIG. 7B: Over-expression of sGCα1 protects prostate cancer cells from the lethal effects of etoposide. LNCaP cells were infected with control empty adenovirus (–sGCα1; 20 MOI) or sGCα1-expressing adenovirus (+sGCα1; 2 or 20 MOI) and treated with 10 µM etoposide. After two days of incubation, cell number was quantified by MTT assay. Bar graphs represent averages of three independent experiments plus standard deviations. All activities are relative to the first condition, and this activity was set to 100%. Student T test showed significant differences (P<0.04), as indicated.

FIG. 7A shows that the viability of prostate cancer cells is affected by sGCα1 expression. LNCaP cells were transfected with control siRNA or sGCα1 siRNA and grown for 0, 3, or 6 days in the absence of serum. Cell number was measured using the MTT assay. Each data point represents averages of three independent experiments plus standard deviations.

LNCaP cells were infected with an sGCα1-expressing adenovirus and treated with etoposide, an inducer of apoptosis. Etoposide significantly reduced the viability of LNCaP cells (FIG. 7A), likely due to apoptosis. Remarkably, over-expression of sGCα1 markedly enhanced cell viability, showing that sGCα1 desensitizes cells to apoptosis-inducing drugs (FIG. 7A). This finding, together, with the PCR array data showing that sGCα1 can regulate Survivin expression, is consistent with results showing that Survivin desensitizes prostate cancer cells to etoposide.

These results also show that sGCα1 is useful as a therapeutic target for stopping the growth of androgen-independent prostate tumors. Furthermore, the specific results described herein now show that the sGCα1-p53 interaction is useful as a good target for disruption, which then can lead to the reactivation of p53 and its tumor suppressor functions.

sGCα1 Expression Increases with Increasing Grade of Prostate Cancer

Figure 8:
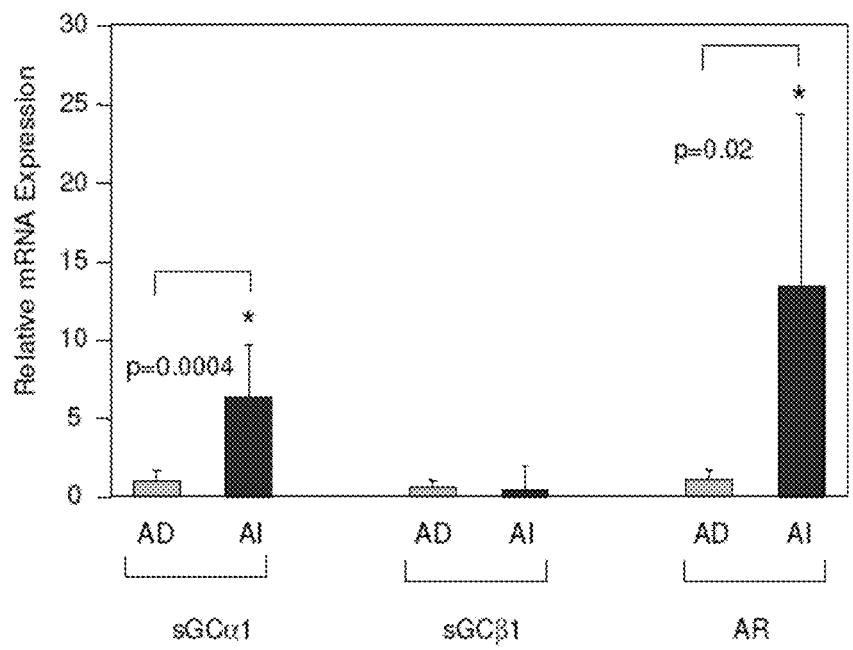
FIG. 8: sGCα1 is over-expressed in hormone refractory, metastatic prostate cancer. RNA was prepared from 52 androgen-dependent (AD) and 11 androgen-independent prostate tumors and subjected to Affymetrix microarray analysis and expression was measured for sGCα1, sGCβ1, and AR. Student T test was used to show significantly increased (P<0.05) expression in AI tumors for sGCα1 and AR.

Affymetrix microarray analysis was used to show that sGCα1 expression is significantly enhanced in hormone-refractory, metastatic prostate (AI) tumors as compared to hormone-dependent tumors (D) (FIG. 8). Interestingly, the sGCβ1 levels are low in both types of tumor tissues (FIG. 8). AR levels are dramatically higher in AI tumors than AD tumors (FIG. 8).

Figure 9A:
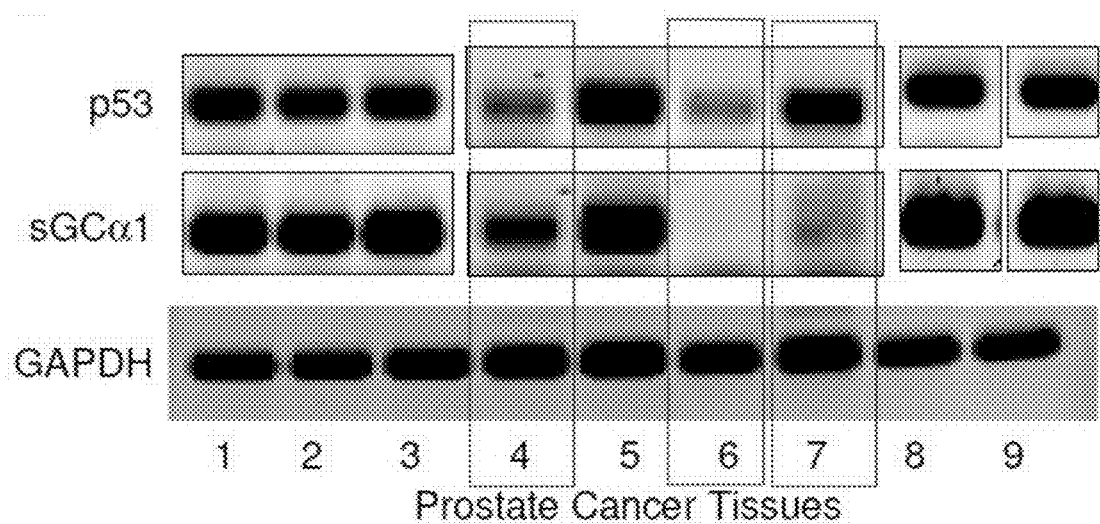
FIGS. 9A-C: sGCα1 expression directly correlates with p53 expression in prostate tumors. Total RNA was isolated from 9 metastatic prostate tumors and used to synthesize cDNA by reverse transcription. The cDNA was then used in a PCR reaction to measure gene expression"

Reverse transcription-polymerase chain reaction (RT-PCR) was used to measure the expression of sGCβ1 and p53 malignant prostate cancer. Among the nine tumors analyzed, eight showed a strong correlation between p53 and sGCα1 expression: high p53 and sGCα1 expression was detected in six tumors, while two tumors (Tumors 4 and 6) yielded significantly reduced levels of both genes (FIG. 9A). The only exception was Tumor 7, which exhibited high p53 but low sGCα1 expression. To confirm these data and have template for subsequent DNA sequencing, three overlapping PCR products were synthesized covering the entire coding region of p53.

Figure 9B:
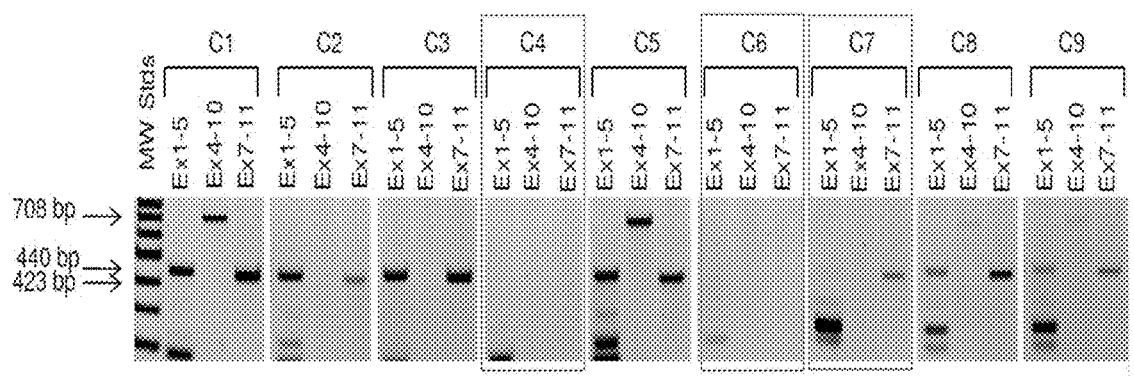
Figure 9C:
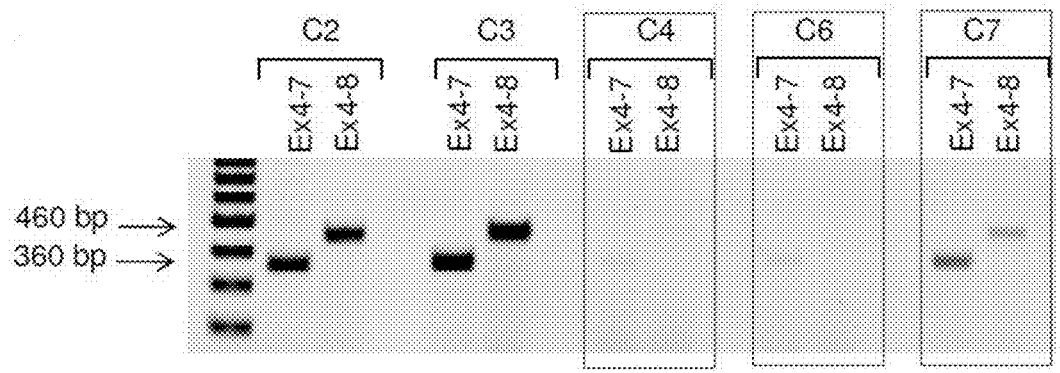

As shown in FIG. 9B, two or three PCR fragments were detected in significant levels in all the tumors that showed high p53 expression by RT-PCR, while little or no PCR products were obtained in the two low p53-expressing tumors and, surprisingly, Tumor 7. To further analyze p53 expression, two additional PCR products were synthesized, encompassing p53 exons 4-7 and exons 4-8. This analysis showed high levels of PCR products for Tumors 2 and 3, and significantly lower for Tumors 4, 6, and 7. Collectively, these results demonstrate a strong correlation in mRNA expression levels between sGCα1 and p53 in prostate tumors.

Figure 10A:
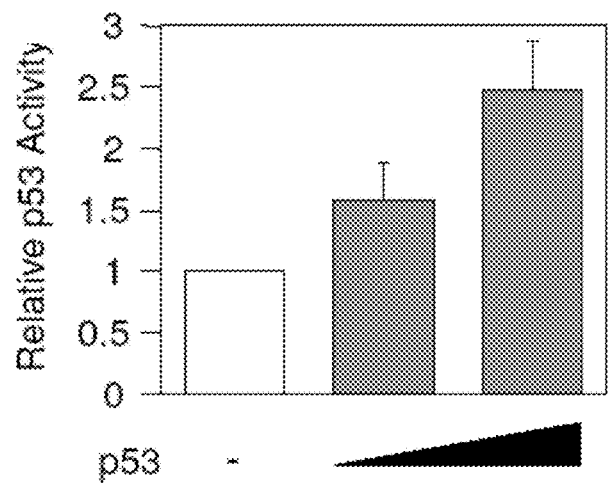
FIG. 10A: LNCaP cells were transfected with 0.1 µg p53-Luc reporter plasmid and 0.1 or 0.5 µg p53.
Figure 10B:
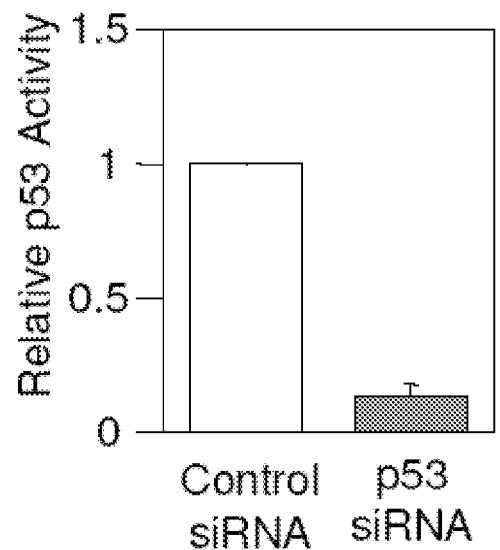
FIG. 10B: LNCaP cells were transfected with 0.1 µg p53-Luc reporter plasmid and control or p53 siRNA.
Figure 10C:
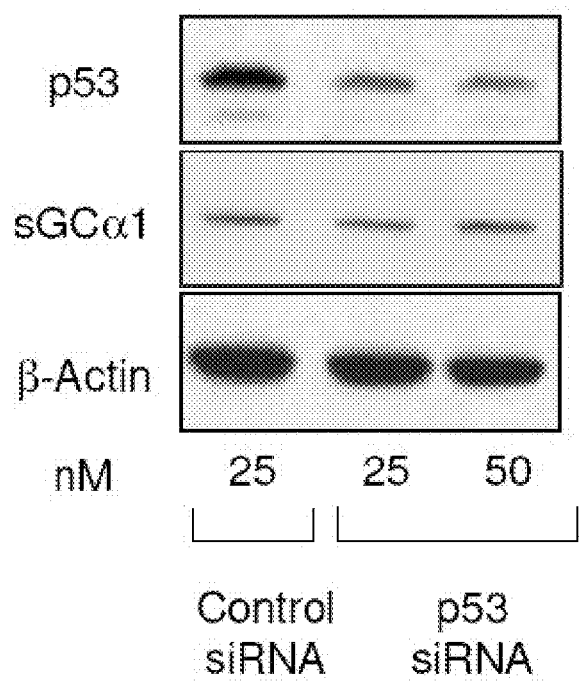
FIG. 10C: LNCaP cells were transfected with control or p53 siRNA and subjected to Western blotting to measure expression of p53 and sGCα1. β-actin was used as a loading control.

To confirm the utility of the p53-regulated reporter plasmid, transfection experiments in LNCaP cells showed that over-expression of p53 led to higher p53 transcriptional activity (FIG. 10A) and siRNA transfection led to lower p53 transcriptional activity (FIG. 10B). As shown in FIG. 10C, siRNA transfection led to significantly reduced p53 protein levels.

Figure 11A:
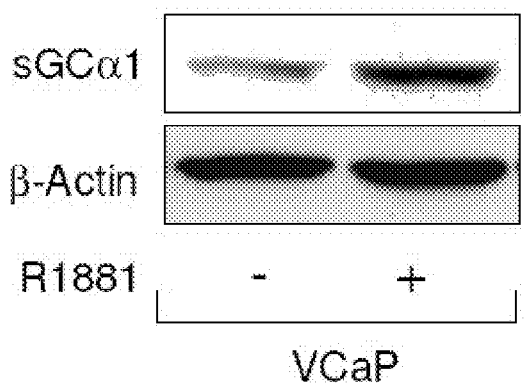
FIG. 11A: VCaP cells were treated with or without 1 nM R1881 and Western blotting was used to measure expression of sGCα1. β-actin was used as a loading control.

VCaP cells, which express a wild-type AR and exhibit androgen-dependent proliferation, were also examined for sGCα1 expression. As FIG. 11A shows, R1881 significantly induced sGCα1 protein expression in VCaP cells, demonstrating that androgen-induced expression of sGCα1 is not unique to LNCaP cells or dependent on the mutant AR expressed in LNCaP cells.

Figure 11B:
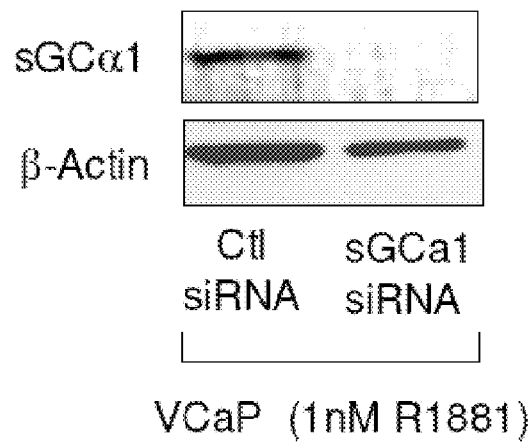
FIG. 11B: VCaP cells, treated with 1 nM R1881, were transfected with control or p53 siRNA and subjected to Western blotting to measure expression of sGCα1. β-actin was used as a loading control.
Figure 11C:
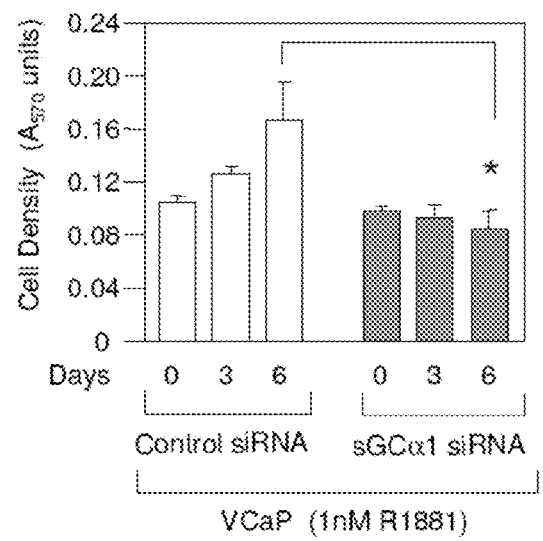
FIG. 11C: VCaP cells were grown in the presence of 1 nM R1881 and transfected with control or sGCα 1 siRNA. Cell density was measured at day 0, 3, and 6 using the MTT assay. Student T test showed significant differences (P<0.04), as indicated.

To determine if sGCα1 also plays a role in VCaP cell proliferation, these cells were transfected with siRNA to reduce endogenous expression of sGCα1 (FIG. 11B). Importantly, the siRNA-transfected cells were completely inhibited in their androgen-induced growth and, in fact, exhibited a decrease in cell number, as compared to cells transfected with control siRNA (FIG. 11C). These results mimic what was observed in LNCaP cells and suggest that sGCα1 involvement in cell proliferation may be a common property of androgen-induced growth of prostate cancer cells.

Expression of sGCβ1 relieves sGCα1-mediated repression of p53 transcriptional activity (see FIG. 2B), showing that sGCβ1 dimerization with sGCα1 can disrupt the sGCα1 negative activity on p53. A peptide-based approach for disrupting the sGCα1 inhibition of p53 was used to determine whether peptides mimicking the sGCα1 heterodimerization domains will bind to sGCα1 and disrupt its interaction with p53, thereby reactivating p53 and leading to cell death.

Figures 12A, 12B:
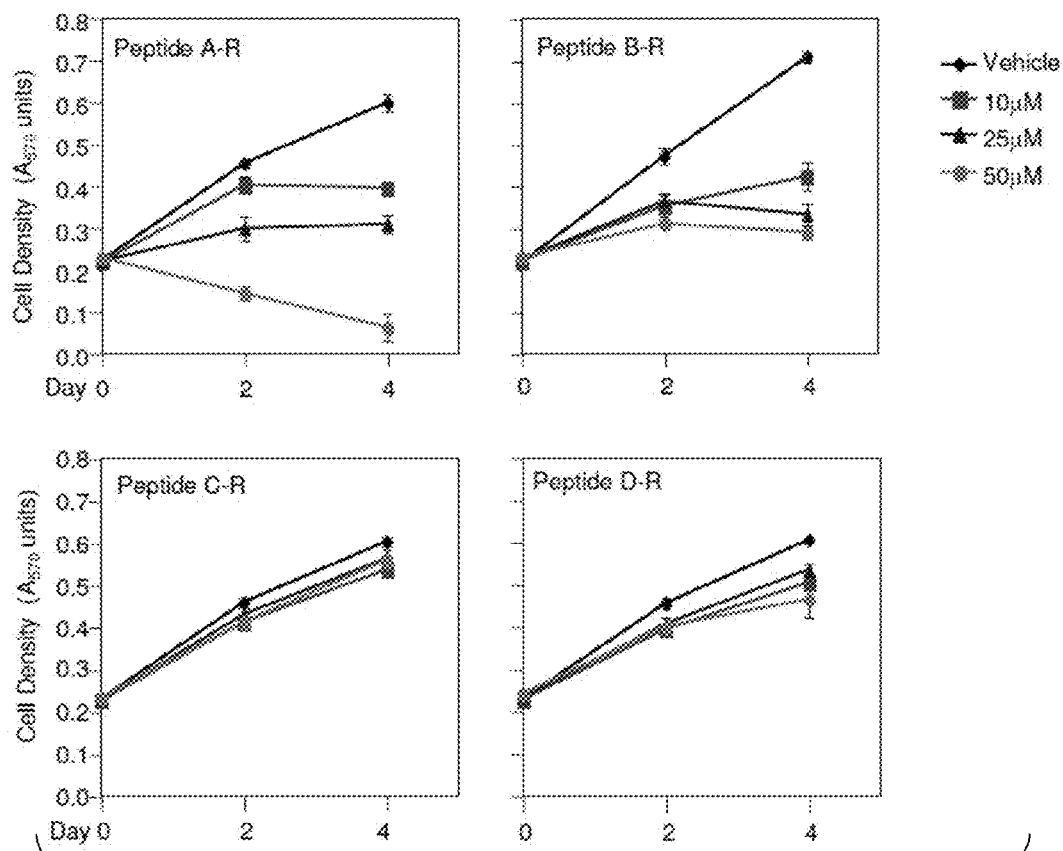
FIGS. 12A-B: Peptides mimicking sGCβ1 dimerization domains with sGCα1 are toxic to cultured prostate cancer cells.

Four such peptides [SEQ ID NOS:1,2,3,4] were synthesized, varying in length from 11 to 19 amino acids, based on the four known sGCβ1 heterodimerization domains (FIG. 12A).

```
Peptide A-8R--
                                          [SEQ ID NO: 1]
Ac-TFCKAFPFHIIRRRRRRRR-OH Peptide B-8R--
                                          [SEQ ID NO: 2]
Ac-LRLKGQMIYLRRRRRRRR-OH
```

```
Peptide C-8R--
                                            [SEQ ID NO: 3]
Ac-PLHDATRDLVRRRRRRRR-OH Peptide D-8R--
                                            [SEQ ID NO: 4]
Ac-RALEDEKKKTDTLLYSVLPPRRRRRRRR-OH.
```

Each peptide contained 8 arginines at the C-terminus, a sequence which is known to mediate plasma membrane translocation and cellular internalization. Treatment of LNCaP cells with different concentrations of peptides resulted in cell death induced by two of the four peptides.

Figure 13A:
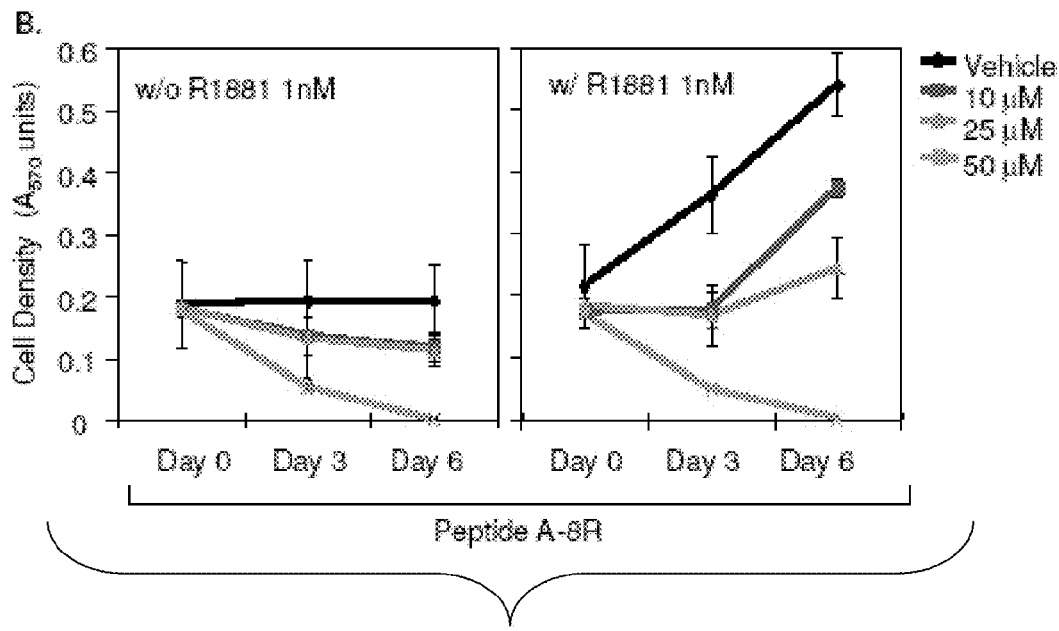
FIGS. 13A-B: A peptide mimicking a sGCα1 dimerization domain with sGCα1 is highly toxic to cultured prostate cancer cells.

As shown in FIG. 13A, Peptide B-8R [SEQ ID NO: 2] stopped the growth of LNCaP cells while Peptide A-8R [SEQ ID NO: 1] was highly cytotoxic, killing most of the cells. This cytotoxicity of Peptide A-8R [SEQ ID NO: 1] is clearly shown in FIG. 13A, in which 50 mM peptide treatment led to 100% cell death by day 6.

Figure 13B:
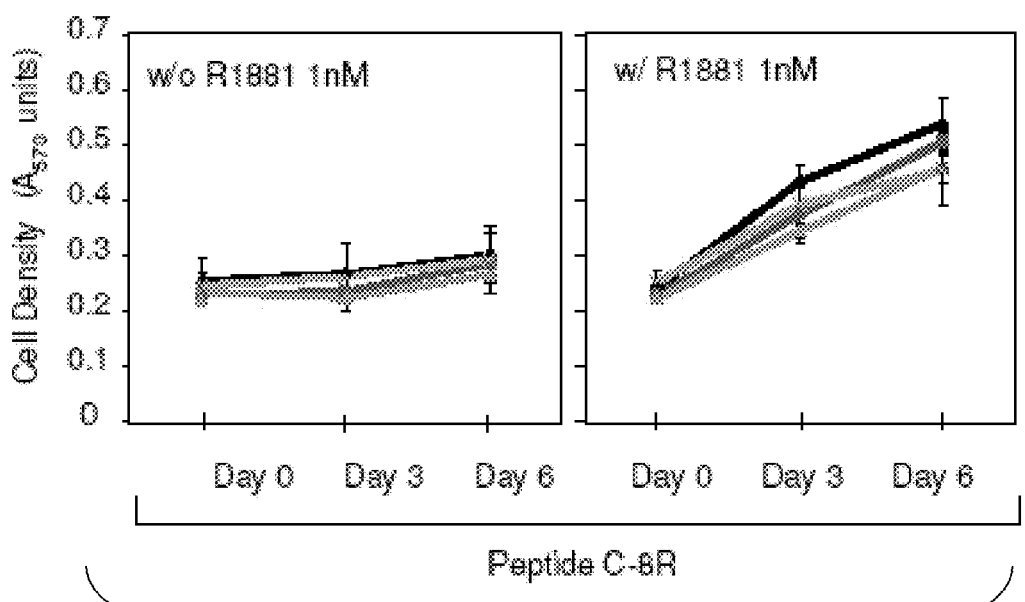
Figure 14A:
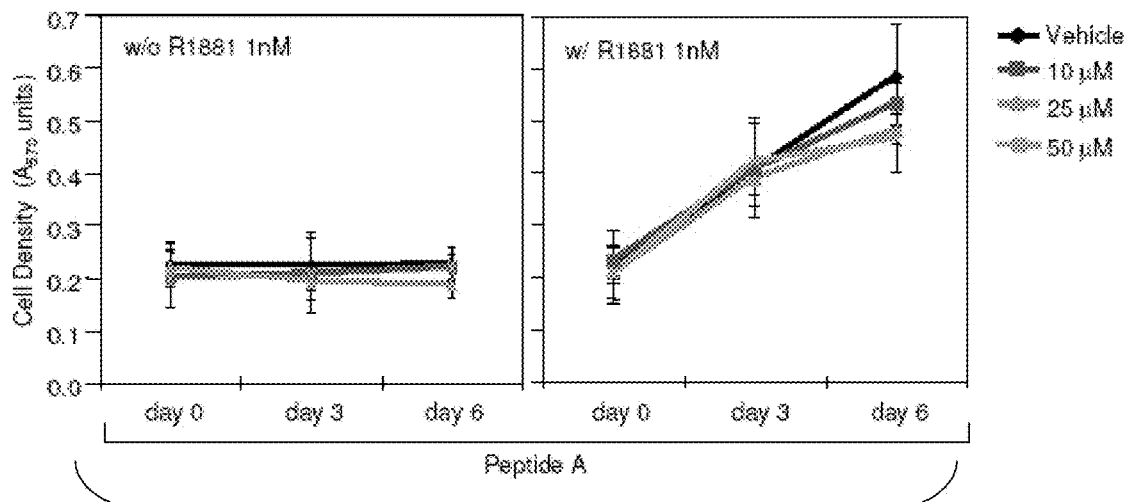
FIGS. 14A-B: The cytotoxic activity of Peptide A-8R [SEQ ID NO: 1] requires a membrane translocation signal.
Figure 14B:
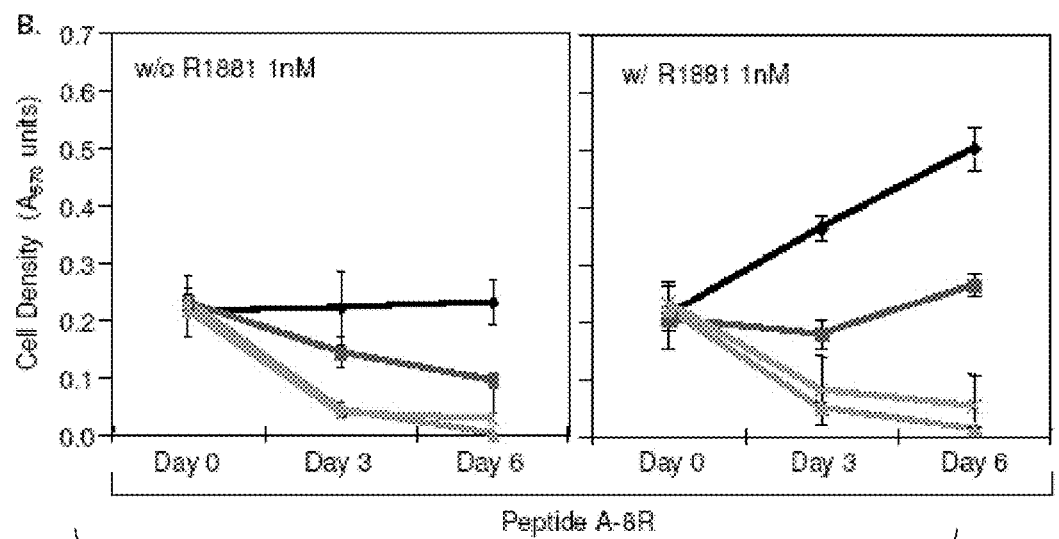

Importantly, Peptide A-8R [SEQ ID NO: 1] induced LNCaP cell death in both the absence and presence of androgens (FIG. 13A). In contrast, an inactive peptide, Peptide C-8R [SEQ ID NO: 3], had no effect (FIG. 13B), demonstrating that the amino-acid sequence of Peptide A was required for the cytotoxic effect and excluding potential cytotoxicity induced by the 8-arginine sequence. When LNCaP cells were treated with Peptide A lacking 8 arginines, no effect was observed on cell growth (FIG. 14A), in contrast to the strong cytotoxic effect of Peptide A-8R [SEQ ID NO: 1] (FIG. 14B), strongly showing that cellular internalization is required for the peptide cytotoxic effect.

Figure 15A:
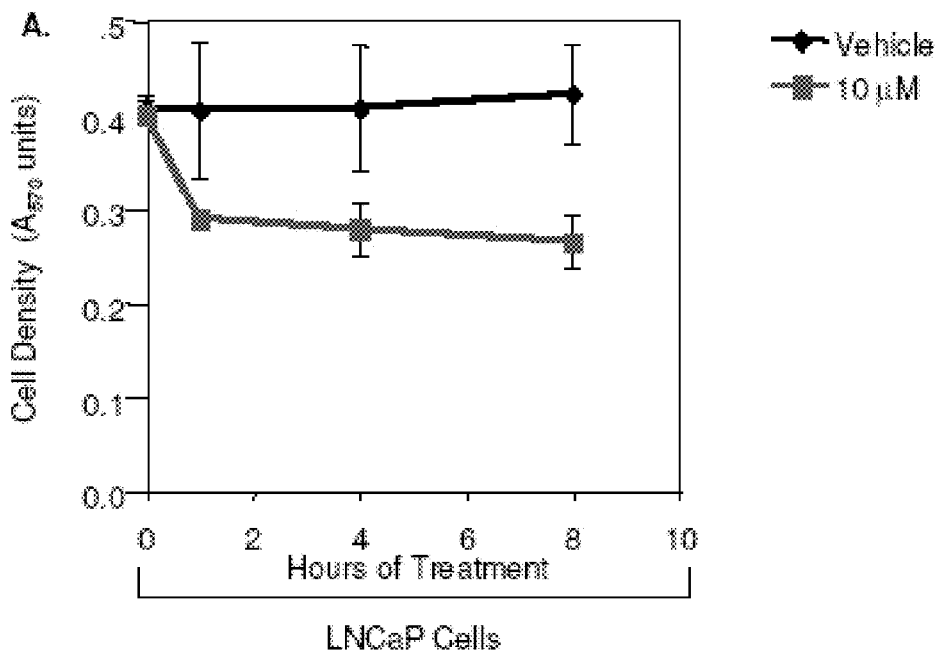
FIGS. 15A-C: Peptide A-8R [SEQ ID NO: 1] is toxic to hormone-refractory prostate cancer cells.
Figure 15B:
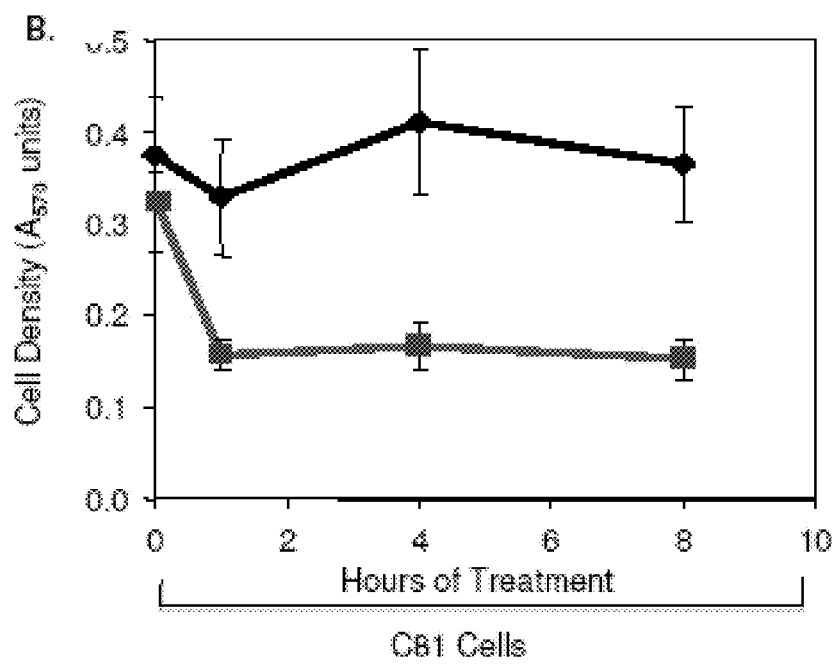
Figure 15C:
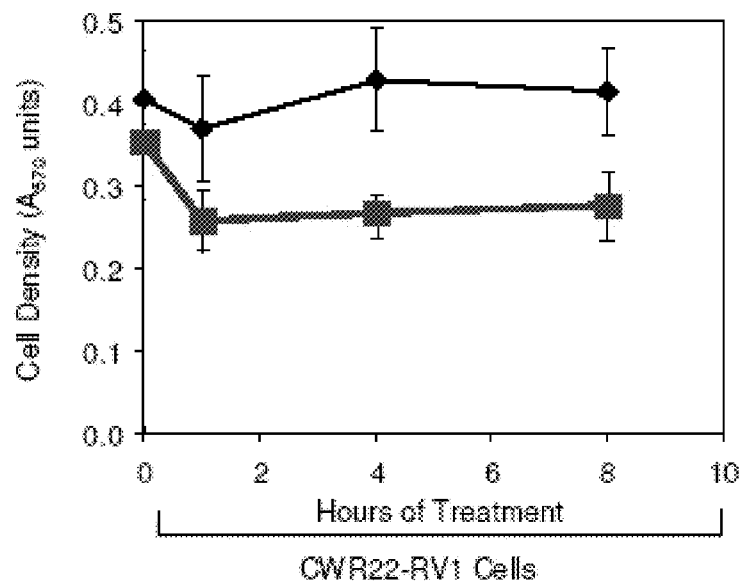

To measure how rapid the cytotoxic effect of Peptide A-8R [SEQ ID NO: 1] occurs, LNCaP cells were treated with 10 µM peptide and incubated for 1-8 hrs. As shown in FIG. 15A, there is a steep decline in cell number with one hour of peptide treatment and then a gradual decline over the next seven hours. Using the same conditions, C81 cells were used to study the peptide effect on hormone-refractory prostate cancer cells. As shown in FIG. 15B, Peptide A-8R [SEQ ID NO: 1] was very effective at killing C81 cells, matching the effect that was observed on hormone-dependent LNCaP cells. FIG. 15C shows that Peptide A-8R [SEQ ID NO: 1] was also able to kill another hormone-refractory prostate cancer cell line, CWR22-Rv1 cells, which is distinct from LNCaP cells. These data demonstrate that hormone-refractory prostate cancer cells are similarly sensitive to the cytotoxic effect of Peptide A-8R [SEQ ID NO: 1] as are hormone-dependent cells, suggesting that this peptide may be effective against hormone-refractory prostate cancer, the lethal form of the disease.

Figure 16A:
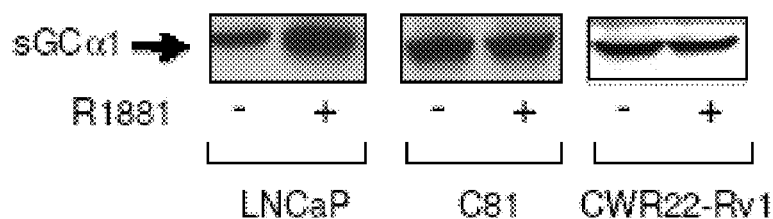
FIGS. 16A-B: sGCα1 is expressed in AR-positive prostate cancer cells, but not AR-negative prostate cancer or kidney cancer cells.
Figure 16B:

Endogenous sGCα1 is expressed in LNCaP, C81, and CWR22-Rv1 cells (FIG. 16A), all of which are sensitive to the cytotoxic effect of Peptide A-8R [SEQ ID NO: 1] (see FIG. 15). These data show that the peptide effect requires endogenous sGCβ1 expression, an expected finding since sGCα1 is the designed target of Peptide A-8R [SEQ ID NO: 1]. To confirm, several different cancer cell lines were studied that do not express endogenous sGCα1 (FIG. 16B).

Figure 17A:
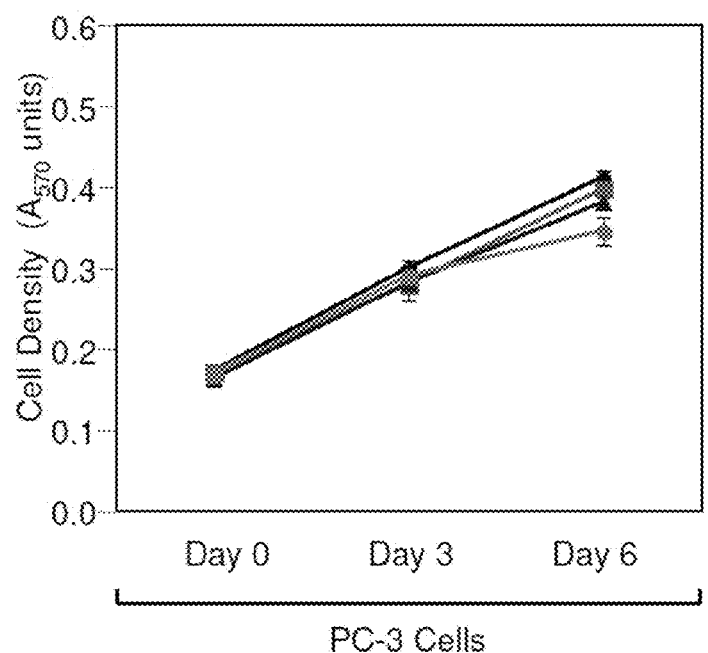
FIGS. 17A-C: Peptide A-8R [SEQ ID NO: 1] is not toxic to cancer cells deficient in sGCα1 expression.
Figure 17B:
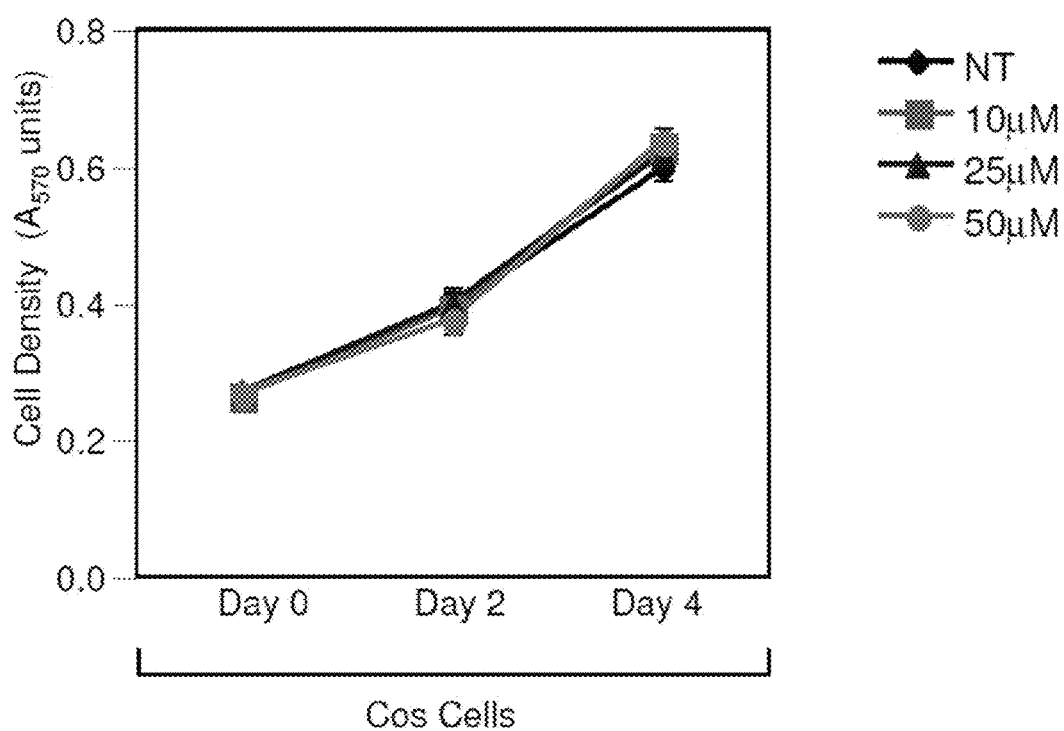
Figure 17C:
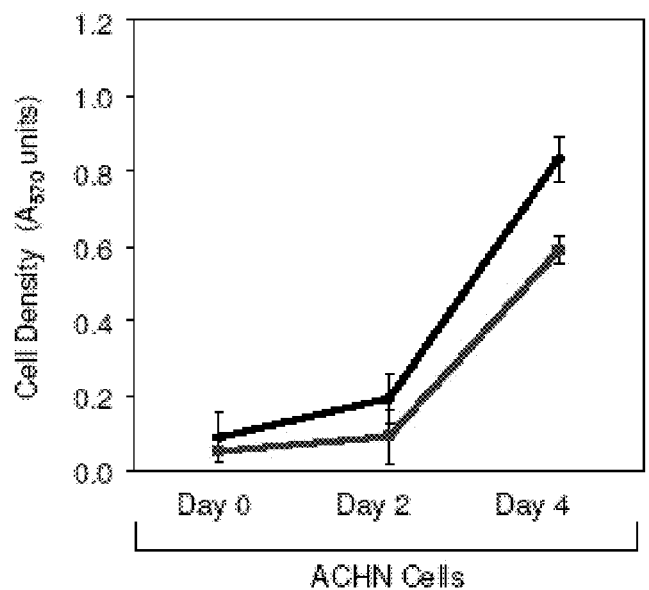

As shown in FIGS. 17A-C, Peptide A-8R [SEQ ID NO: 1] had little to no effect on PC-3 (prostate cancer), Cos (mouse kidney cancer), and ACHN cells (human kidney cancer), even at a high concentration of 100 µM. These data strongly support the contention that the cytotoxic activity of Peptide A-8R [SEQ ID NO: 1] depends on endogenous sGCα1 protein.

Figure 18A:
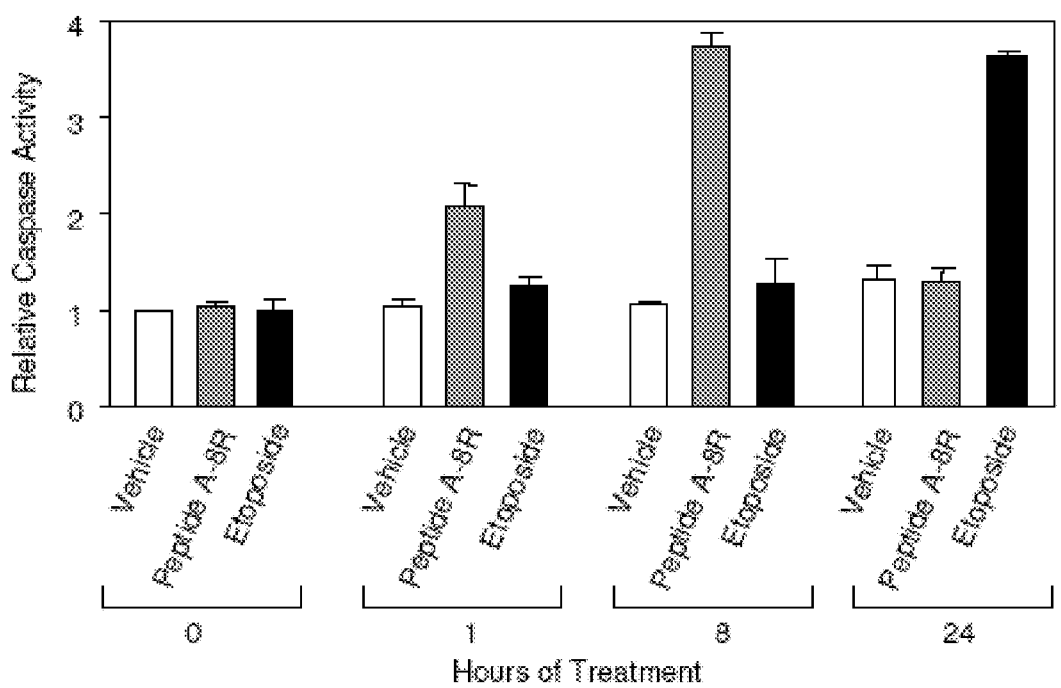
FIGS. 18A-B: Peptide A-8R [SEQ ID NO: 1] induces apoptosis of prostate cancer cells.
Figure 18B:
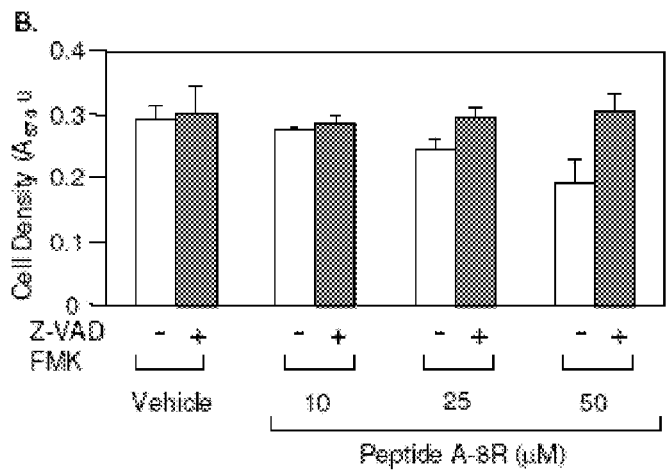

To determine if the cytotoxicity of Peptide A-8R [SEQ ID NO: 1] is through apoptosis, LNCaP cells were monitored for Caspase 3/7 activity. As shown in FIG. 18A, Peptide A-8R [SEQ ID NO: 1] induced a 2-fold increase in caspase activity by 1 hour, which increased to nearly 4-fold after 8 hrs. Caspase activity diminished to Vehicle levels at after 24 hrs, when most of the cells were dead. The positive control Etoposide induced similar levels of caspase activity, but only after 24 hrs of treatment. Thus, Peptide A-8R [SEQ ID NO: 1] was able to induce Caspase 3/7 activity much faster than the well-studied apoptosis-inducing drug Etoposide. To confirm that the Peptide was killing cells via apoptosis, the inventors used the pan-caspase inhibitor Z-VAD-FMK. Pre-treatment of LNCaP cells with Z-VAD-FMK resulted in complete relief of the Peptide A-8R [SEQ ID NO: 1] cytotoxic effect, even at a high peptide concentration of 50 µM (FIG. 18B). Importantly, Z-VAD-FMK had no significant effect on Vehicle-treated cells (FIG. 18B). Collectively, these data demonstrate that Peptide A-8R [SEQ ID NO: 1] is able to quickly and efficiently kill LNCaP cells through apoptosis.

Peptide A-8R [SEQ ID NO: 1] Interacts with sGCα1

Figure 19A:
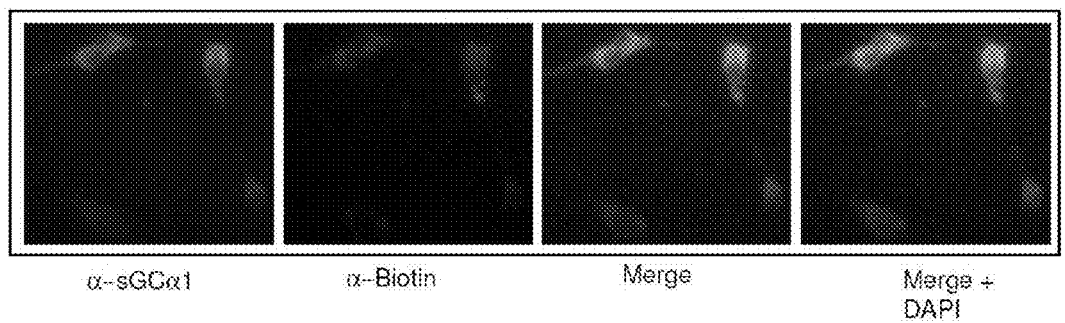
FIGS. 19A-C: Peptide A-8R [SEQ ID NO: 1] associates with sGCα1 in prostate cancer cells.
Figure 19B:
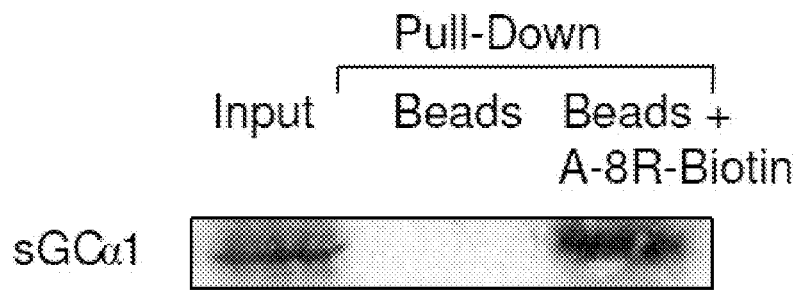
Figure 19C:
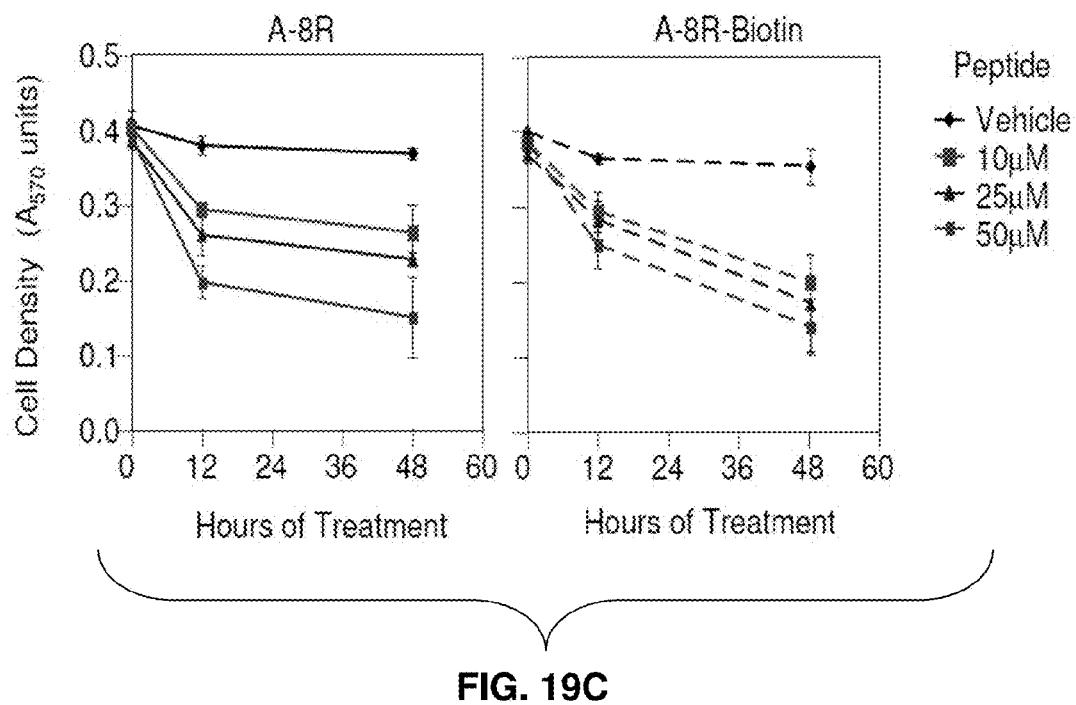

Peptide A-8R [SEQ ID NO: 1] was synthesized with a Biotin tag at the C-terminus, giving Peptide A-8R-Biotin [SEQ ID NO: 1]. In the first assay, LNCaP cells were treated with Peptide A-8R-Biotin [SEQ ID NO: 1] and subjected to immunocytochemistry (FIG. 19A). Endogenous sGCα1 is found primarily or exclusively in the cytoplasm of LNCaP cells. Also, Peptide A-8R-Biotin [SEQ ID NO: 1] is also found in the cytoplasm and colocalizes with sGCα1, as shown by the merged images. These results show that Peptide A-8R-Biotin [SEQ ID NO: 1] interacts with endogenous sGCα1, which was verified by a pull-down experiment. In this second assay (FIG. 19B), LNCaP whole cell extract was incubated with Peptide A-8R-Biotin [SEQ ID NO: 1] and subjected to streptavidin-agarose purification, leading to co-purification of sGCα1. In contrast, the strepatavin-agarose beads were unable to pull-down sGCα1 in the absence of Peptide A-8R-Biotin [SEQ ID NO: 1]. Collectively, these results show a physical association between Peptide A-8R-Biotin [SEQ ID NO: 1] and sGCα1 and thus make it possible that this association is involved in the cytotoxic activity of Peptide A-8R [SEQ ID NO: 1]. FIG. 19C shows that addition of a Biotin tag to Peptide A-8R [SEQ ID NO: 1] does not affect the cytotoxic efficacy of this peptide.

Figure 20:
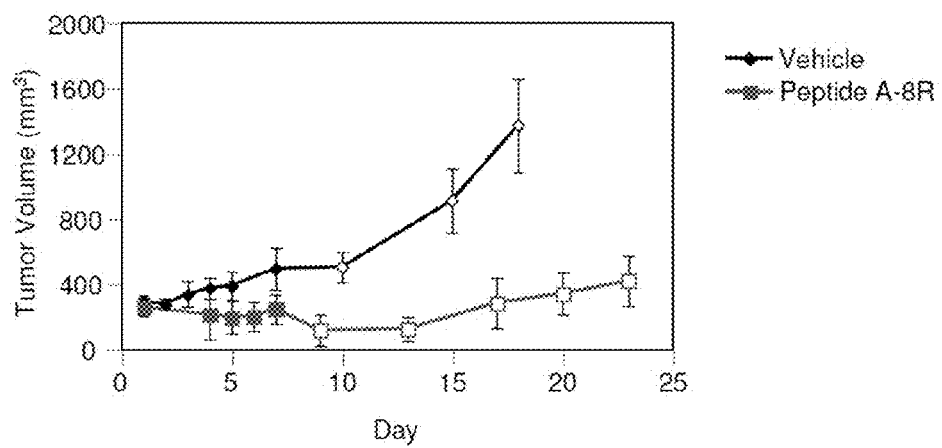
FIG. 20: Peptide A-8R [SEQ ID NO: 1] inhibits the growth of LNCaP prostate xenograft tumors. LNCaP xenograft tumors were grown in nude mice to a size of 200-400 cubic mm and then treated with daily intratumoral injections of either Peptide A-8R [SEQ ID NO: 1] (80 mg/kg of animal) or Vehicle (DMSO) for seven days, after which the tumors were left untreated and allowed to grow for an additional 2-3 weeks. Each point represents the average tumor size of three animals plus/minus the standard deviations. Note that open squares or circles represent no treatment of either Peptide A-8R [SEQ ID NO: 1] or vehicle.

The cytotoxic activity of Peptide A-8R [SEQ ID NO: 1] cultured prostate cancer cells show that it can have potential therapeutic activity on tumorigenesis. This was analyzed using LNCaP xenograft tumors established in nude mice and direct injection of Peptide A-8R [SEQ ID NO: 1] (FIG. 20). Interestingly, Peptide A-8R [SEQ ID NO: 1] strongly inhibited tumor growth and actually caused tumor regression after seven daily injections of peptide. Even after stopping peptide injection, the tumors that had received Peptide A-8R [SEQ ID NO: 1] grew significantly more slowly than those tumors that received Vehicle treatment.

This experiment was then repeated using hormone-refractory C81 cells. $2 \times 10^6$ C81 cells in 50 µL of growth medium was mixed with 50 µL Matrigel (BD Biosciences) and injected into both flanks of 4-6-week old SCID male mice. When tumor sizes reached 200 $mm^3$, 50 µL of Peptide A-8R (40 mg Peptide A-8R/kg of animal) ["A-8R" disclosed as SEQ ID NO: 1] or vehicle (DMSO) was directly injected into the tumors every other day. Injections were stopped after 5 times and tumors were measured every 3 days. Mice were euthanized after 3 weeks and tumors were excised. All procedures were approved by the University of Toledo, Division of Lab Animal Recourses (DLAR). Protein extracts were prepared by boiling the tumor tissue in 3×SDS buffer, and evaluated by SDS-PAGE gel. The procedure was carried out in strict accordance with the recommendations in the Guide for the Care and Use of Laboratory Animals of the National Institutes of Health. The protocol was approved by the Institutional Animal Care and Use Committee of the University of Toledo. During the experiments, all animals were monitored daily for morbidity and all efforts were made to minimize suffering. At the end of the study, all animals were euthanized using inhalation of carbon dioxide, after which surgery was performed to excise tumors from all animals.

Peptide A-8R [SEQ ID NO: 1] stopped tumor growth and actually caused some tumor regression after five injections of peptide. (FIG. 28A and FIG. 28B.) Remarkably, the tumors did not grow at all three weeks after peptide treatment was stopped, while the vehicle-treated tumors grew by more than three-fold. (FIG. 28A.) To control for potential differences between animals, Peptide A-8R [SEQ ID NO: 1] and vehicle were tested in the same mouse having two tumors. The Peptide-treated tumor was markedly smaller than the vehicle-treated tumor. (FIG. 28C.) In fact, the Peptide-treated tumor did not grow, as in the other animals, while the vehicle-treated tumor grew significantly. These data demonstrate a strong anti-tumor activity for Peptide A-8R [SEQ ID NO: 1] in nude mice, and indicate Peptide A-8R [SEQ ID NO: 1] can be effective against castration-resistant prostate cancer (CRPC).

Figure 21A:
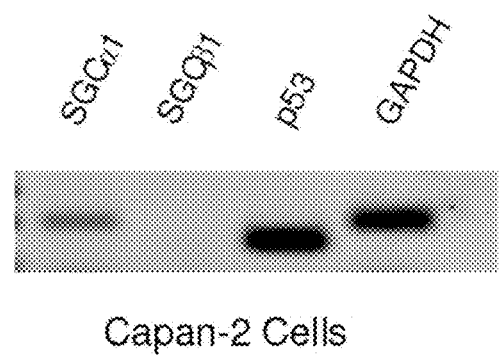
FIGS. 21A-B: Peptide A-8R [SEQ ID NO: 1] is cytotoxic to pancreatic cancer cells.
Figure 21B:
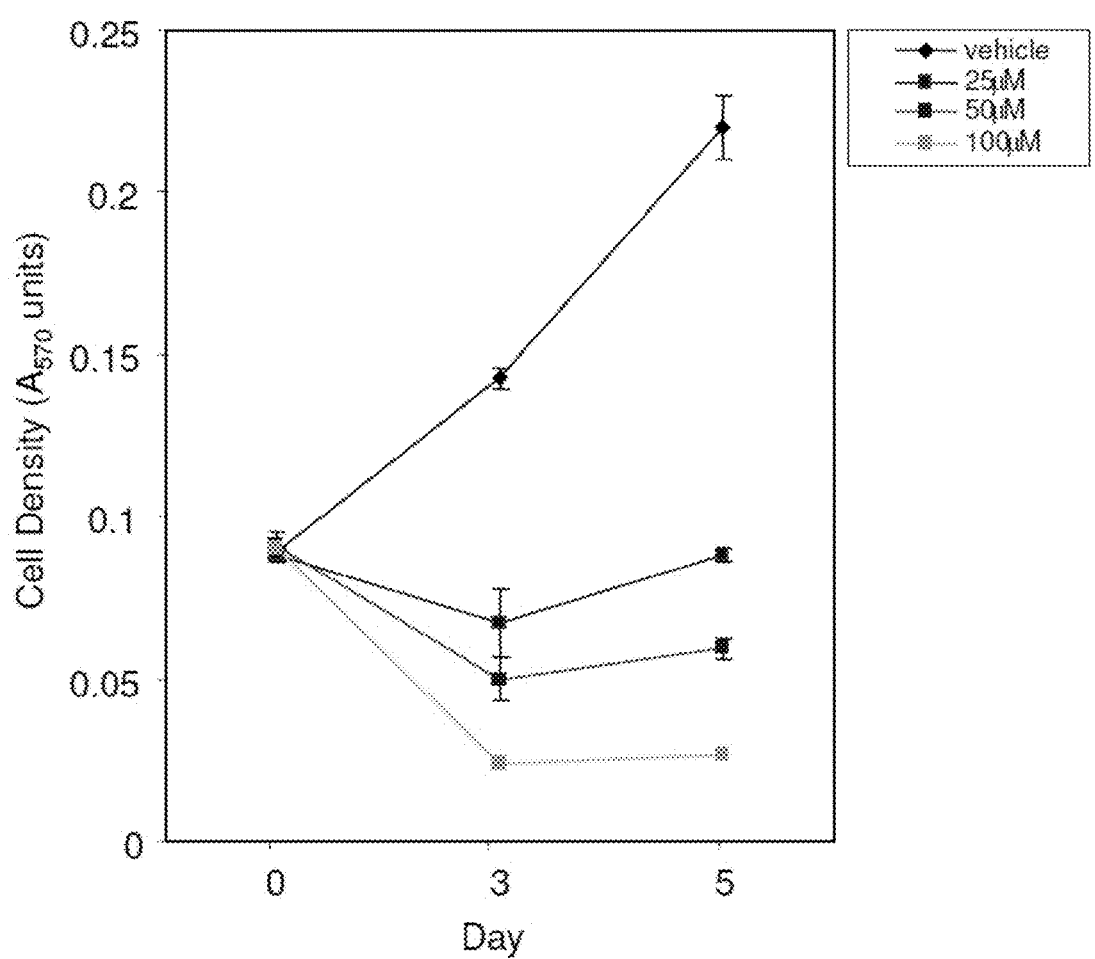
Figure 22:
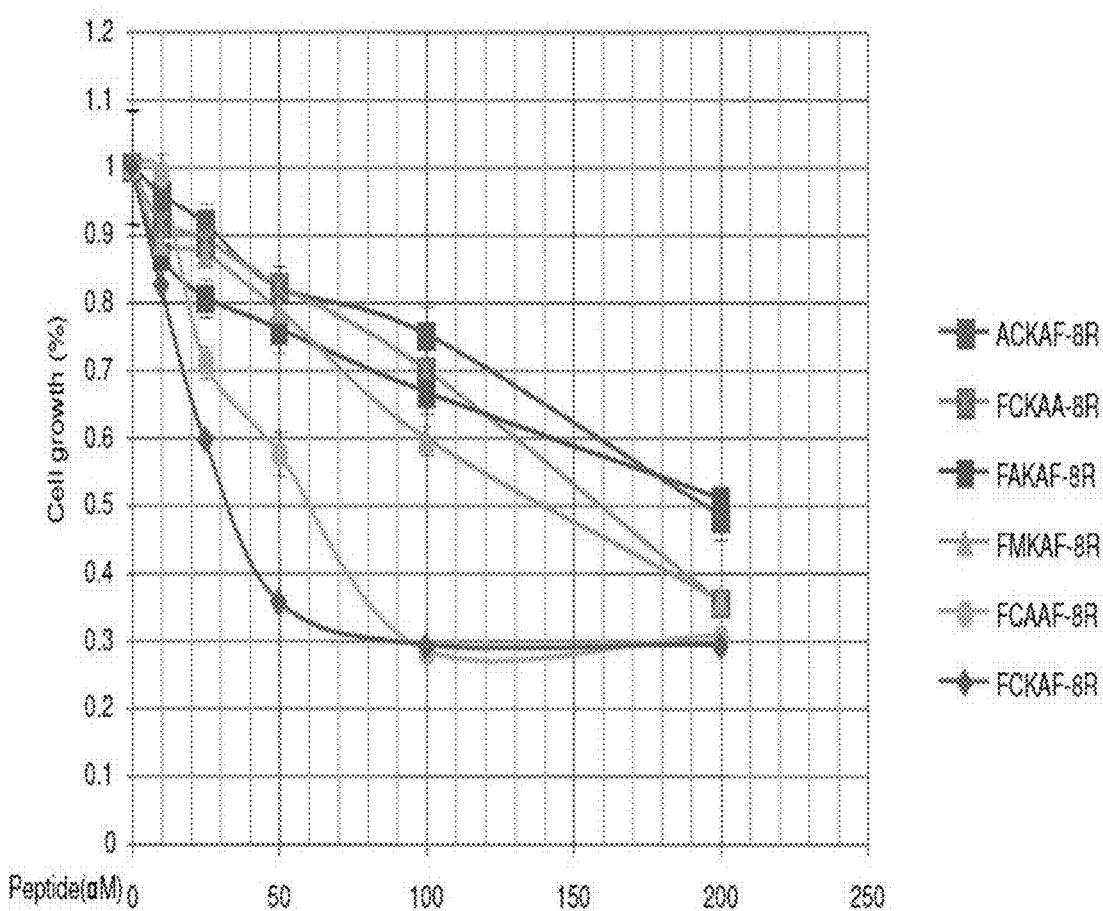
FIG. 22: C81 cells were grown for 3 days in the presence of increasing concentration of the listed truncated peptides [SEQ ID NOS: 22, 24, 20, 18, 26, and 10, respectively, in order of appearance]. Cell growth was then measured.
Figure 23:
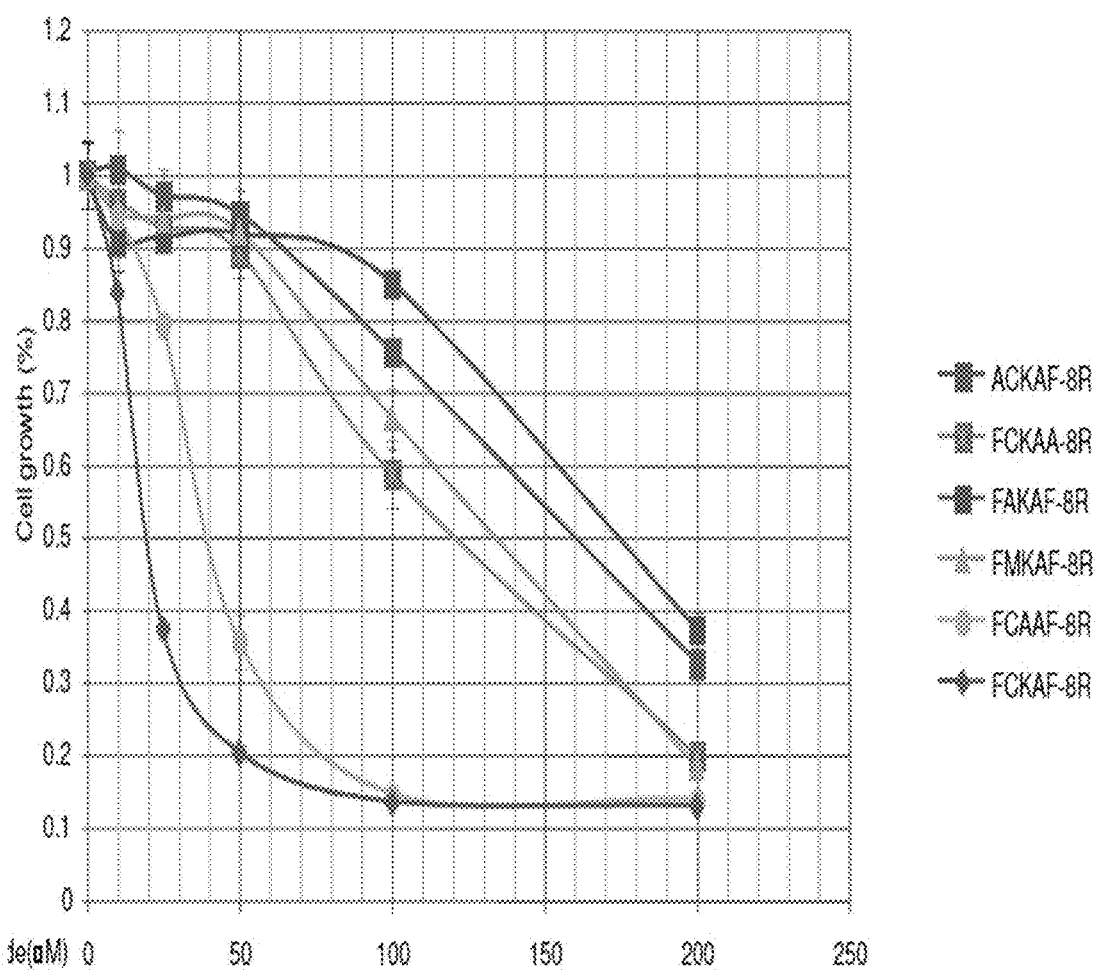
FIG. 23: C81 cells were grown for 6 days in the presence of increasing concentration of the listed truncated peptides [SEQ ID NOS: 22, 24, 20, 18, 26, and 10, respectively, in order of appearance]. Cell growth was then measured.
Figure 24:
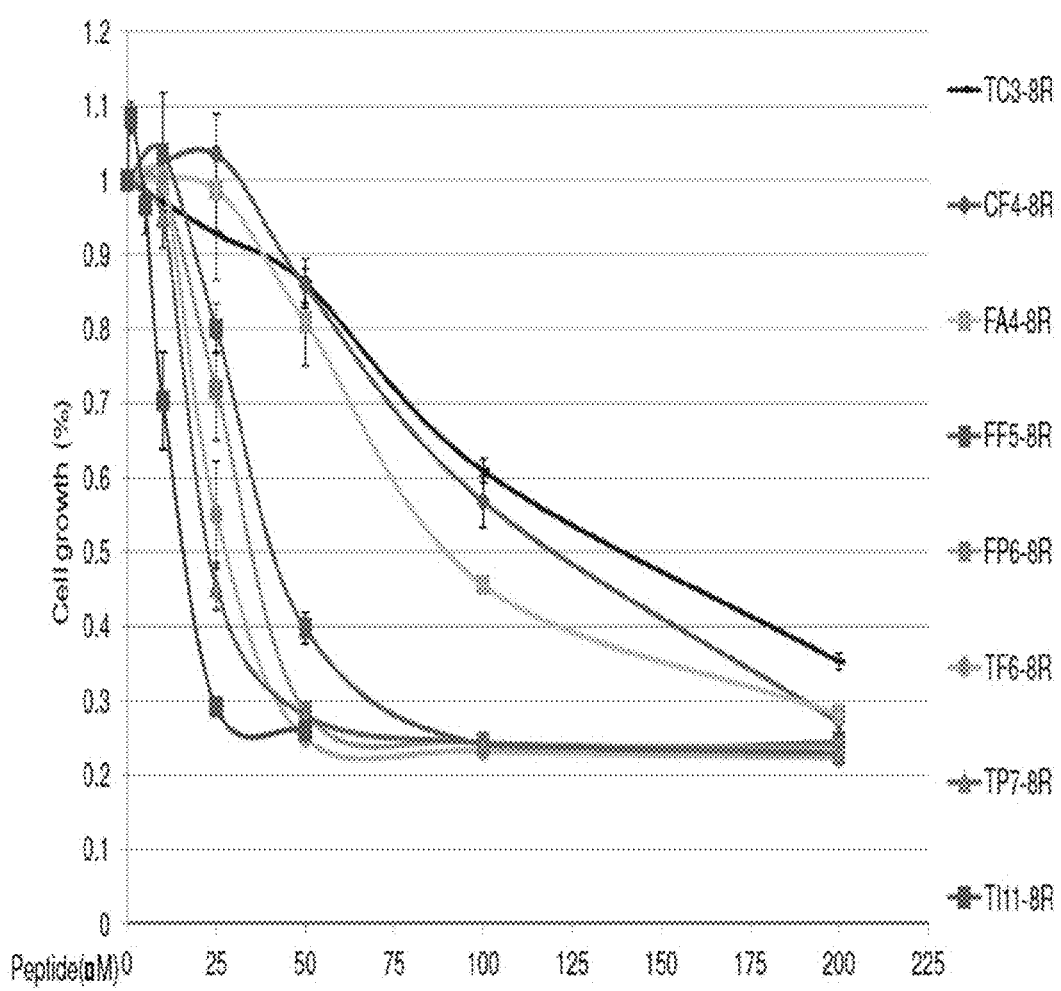
FIG. 24: C81 cells were grown for 3 days in the presence of increasing concentration of the listed Peptide A derivatives [SEQ ID NOS: 32, 30, 28, 10, 16, 14, 12, and 1, respectively, in order of appearance]. Cell growth was then measured.
Figure 25:
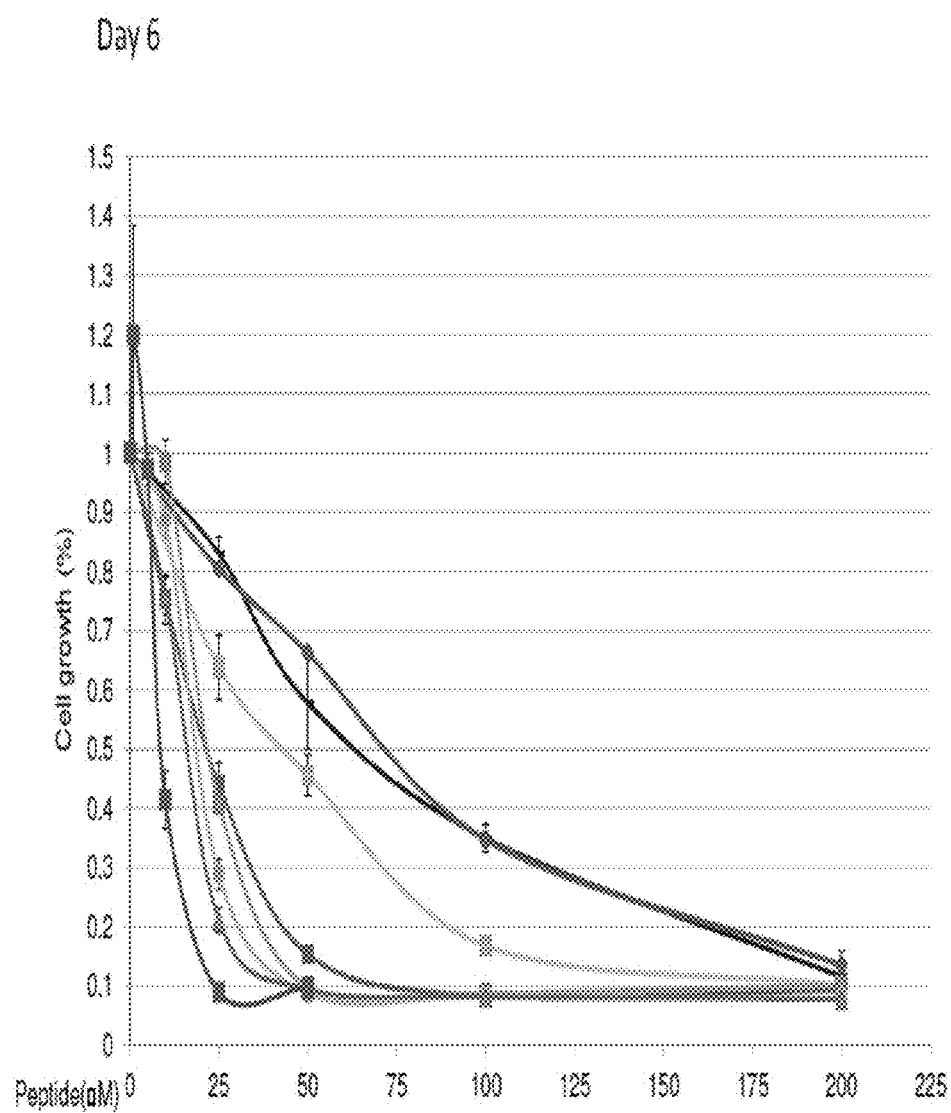
FIG. 25: C81 cells were grown for 6 days in the presence of increasing concentration of the listed Peptide A derivatives [SEQ ID NOS: 32, 30, 28, 10, 16, 14, 12, and 1, respectively, in order of appearance]. Cell growth was then measured.
Figure 26:
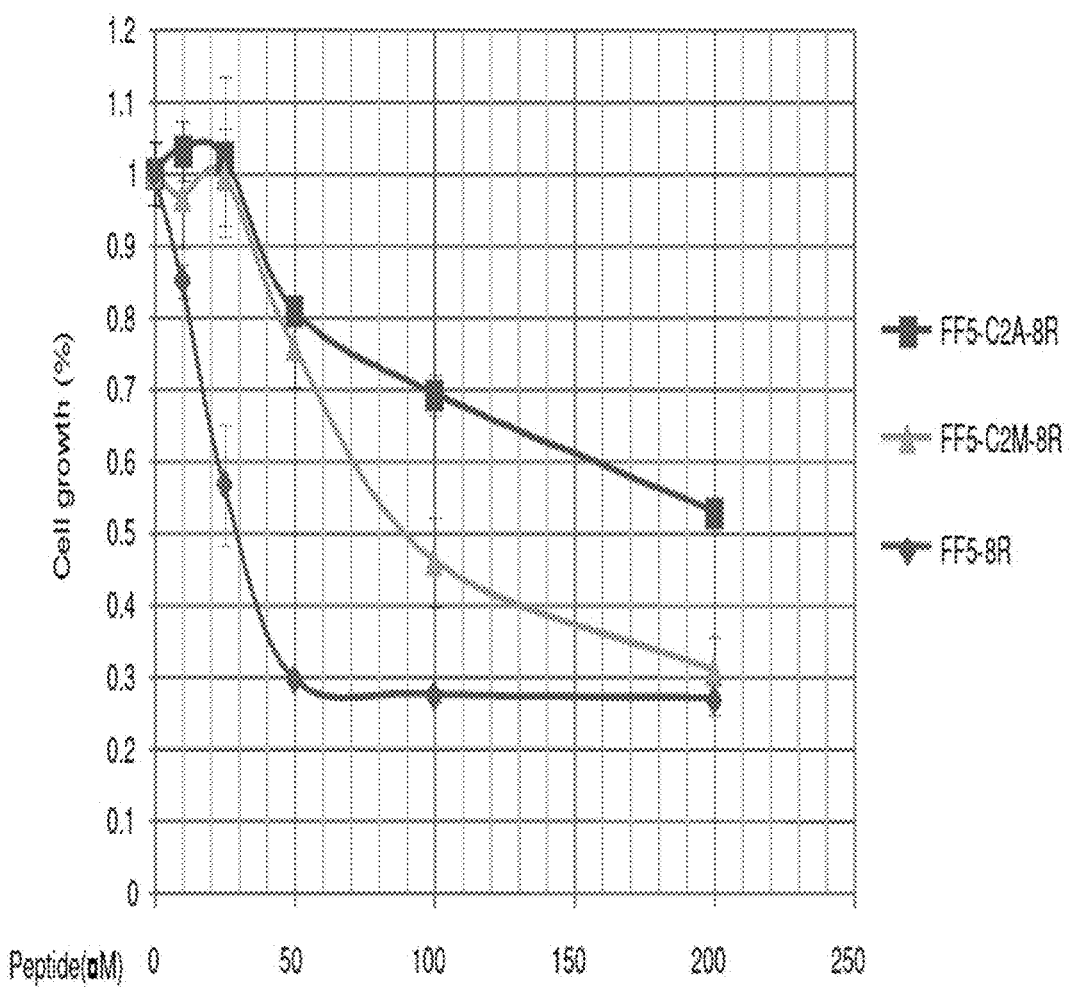
FIG. 26: C81 cells were grown for 3 days in the presence of increasing concentration of the listed Peptide A derivatives [SEQ ID NOS: 20, 18, and 10, respectively, in order of appearance]. Cell growth was then measured.
Figure 27:
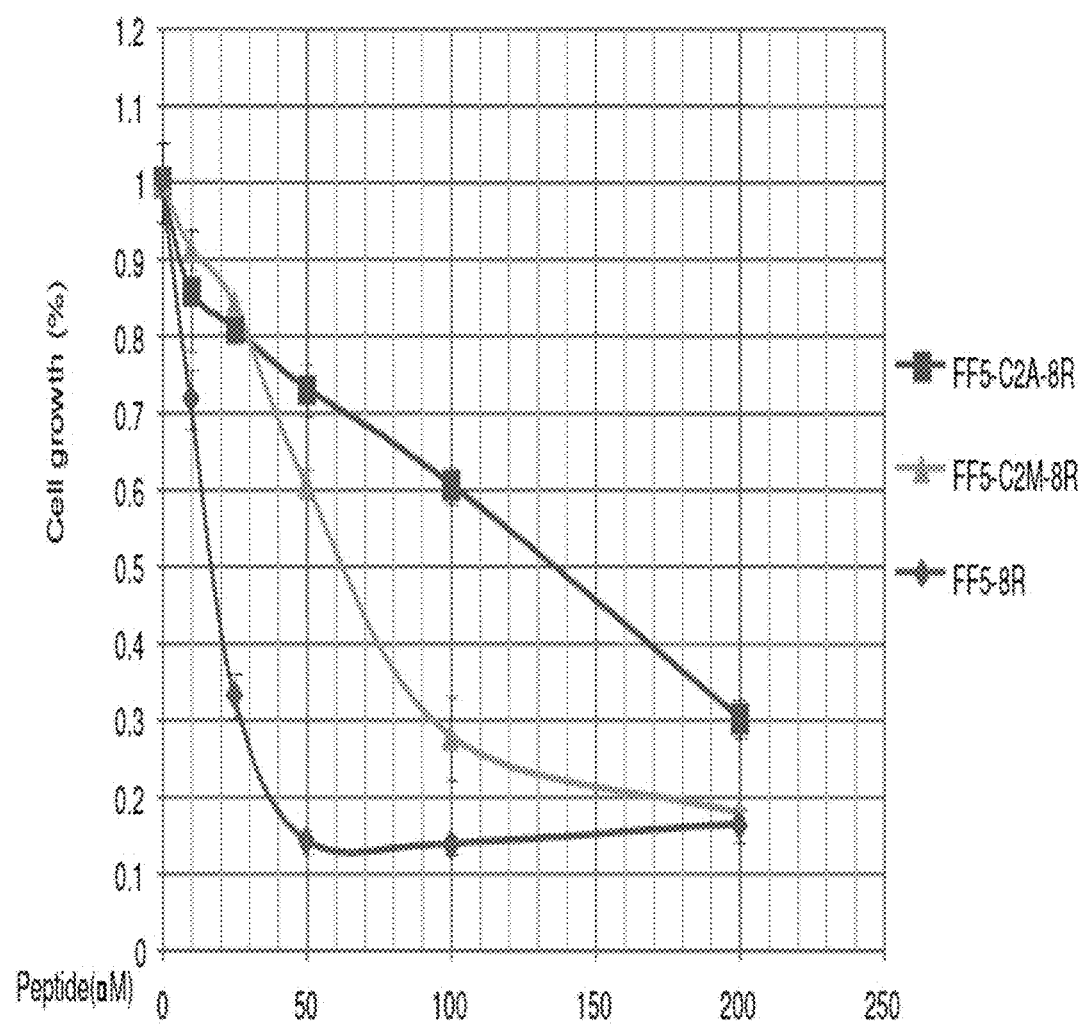
FIG. 27: C81 cells were grown for 6 days in the presence of increasing concentration of the listed Peptide A derivatives [SEQ ID NOS 20, 18, and 10, respectively, in order of appearance]. Cell growth was then measured.

To determine if Peptide A-8R [SEQ ID NO: 1] can be cytotoxic to other cancer cells, a pancreatic cancer cell line, Capan-2, was also tested. As shown in FIG. 21A, Capan-2 cells express sGCα1 and p53, but not sGCβ1, mimicking what is found in LNCaP prostate cancer cells. Interestingly, Peptide A-8R [SEQ ID NO: 1] was strongly cytotoxic to Capan-2 cells, not only stopping their proliferation but also causing cell death (FIG. 21B). These data show that the anti-tumor activity of Peptide A-8R [SEQ ID NO: 1] is not restricted to prostate cancer.

Example II

Truncated Sequences and Derivatives

While Peptide A-8R [SEQ ID NO: 1] has potent anticancer activity, it can be further optimized for selective action on prostate cancer cells and in its overall 'drug-like' properties so that it is also suitable for clinical deployment. To accomplish this, Peptide A-8R [SEQ ID NO: 1] was used as a structural template to design additional peptides, peptidomimetics, and small molecule analogs. Initial analogs were screened by in vitro sGCα1 binding assays to generate structure-activity relationships (SAR) in order to better understand the target protein's interaction with A-8R [SEQ ID NO: 1] and the latter's inhibitory properties. Such screening is useful to define the minimal size peptide required for activity while also establishing parameters that can be useful to transition compounds toward incorporated enhanced peptidomimetic character and drug-like properties. In addition, probes displaying a range of activity can be used to validate the biochemical assay's link to computational chemistry strategies also seeking to further define the mechanism at the level of distinct molecular interactions and binding energies. Active analog compounds can be additionally tested in a cell culture panel of normal mammalian tissues so as to establish structure-toxicity relationships (STR). Further design of compounds can then be able to move toward enhanced efficacy-related SAR and drug-like properties while moving away from STR. While prioritizing the most active compounds, candidates can be selected for the design of probes that can form a covalent bond when interacting with the target protein. By using protein digestion protocols coupled with mass spectrometry, these types of compounds represent useful tools to confirm the nature of the interactions between a ligand (peptide) and its receptor (sGCα1).

Provided herein are truncated variants and derivatives of Peptide A. By way of non-limiting example, the following sequences are truncated variants and derivatives of Peptide A:

```
PI5--
              [SEQ ID NO: 8]
PFHII

TP7--
              [SEQ ID NO: 7]
TFCKAFP

TF6--
              [SEQ ID NO: 13]
TFCKAF

FP6--
              [SEQ ID NO: 15]
FCKAFP

FF5--
              [SEQ ID NO: 9]
FCKAF

FF5-C2M--
              [SEQ ID NO: 17]
FMKAF

FF5-C2A--
              [SEQ ID NO: 19]
FAKAF

FF5-F1A--
              [SEQ ID NO: 21]
ACKAF

FF5-F5A--
              [SEQ ID NO: 23]
FCKAA

FF5-K3A--
              [SEQ ID NO: 25]
FCAAF

FA4--
              [SEQ ID NO: 27]
FCKA

CF4--
              [SEQ ID NO: 29]
CKAF

TC3--
              [SEQ ID NO: 31]
TFC

KP4--
              [SEQ ID NO: 33]
KAFP

KH6--
              [SEQ ID NO: 35]
KAFPFH
```

It is to be understood that, in other embodiments, many other truncated variants and derivatives of Peptide A are useful, and devising such peptides is also within the contemplated scope of the present disclosure.

In one non-limiting example, Peptide A-8R [SEQ ID NO: 1] can be truncated to a smaller peptide that retains the same type of biological activity profile. In certain embodiments, truncating Peptide A-8R [SEQ ID NO: 1] results in greater potency upon conversion of some of the pharmacophore functionalities to peptidomimetic groups that can, in turn, enhance key interactions by lowering the net binding energy. In one experiment, Peptide A-8R [SEQ ID NO: 1] was divided into two parts, using the central proline residue as the division point. Subsequent analysis in cells showed that the N-terminal 7 amino acids (TP7 -TFCKAFP, [SEQ ID NO: 7]) retained cytotoxicity, while the C-terminal 5 amino acids (PFHII, [SEQ ID NO: 8]) had no activity. A minimum number of amino acids desired for cytotoxicity was then identified. The smallest peptide that retains nearly the cytotoxic activity of the 11-amino-acid Peptide A is FF5-8R (FCKAF-8R) [SEQ ID NO: 10]; where the 8R [SEQ ID NO: 6] serves as a membrane translocation signal and is important for cytotoxicity in cells. Replacing the amino acids with alanine clearly demonstrated that the two phenylalanines at the ends and the cysteine were desired for optimal cytotoxicity. Smaller peptides having 4 amino acids (FCKA, [SEQ ID NO: 27]) or 3 amino acids (TFC) exhibited diminished but yet still significant cytotoxicity. The following Peptide A truncated and derivative probes were synthesized and evaluated for their effect on cytotoxicity after 3- and 6-day exposures:

```
Peptide PI5-8R--
                                       [SEQ ID NO: 11]
PFHIIRRRRRRRR Peptide TP7-8R--
                                       [SEQ ID NO: 12]
TFCKAFPRRRRRRRR Peptide TF6-8R--
                                       [SEQ ID NO: 14]
TFCKAFRRRRRRRR Peptide FP6-8R--
                                       [SEQ ID NO: 16]
FCKAFPRRRRRRRR Peptide FF5-8R--
                                       [SEQ ID NO: 10]
FCKAFRRRRRRRR Peptide FF5--
                                       [SEQ ID NO: 9]
FCKAF Peptide FF5-C2M-8R--
                                       [SEQ ID NO: 18]
FMKAFRRRRRRRR Peptide FF5-C2A-8R--
                                       [SEQ ID NO: 20]
FAKAFRRRRRRRR Peptide FF5-F1A-8R--
                                       [SEQ ID NO: 22]
ACKAFRRRRRRRR Peptide FF5-F5A-8R--
                                       [SEQ ID NO: 24]
FCKAARRRRRRRR Peptide FF5-K3A-8R--
                                       [SEQ ID NO: 26]
FCAAFRRRRRRRR
```

```
-continued
Peptide FA4-8R--
                                       [SEQ ID NO: 28]
FCKARRRRRRRR Peptide CF4-8R--
                                       [SEQ ID NO: 30]
CKAFRRRRRRRR Peptide TC3-8R--
                                       [SEQ ID NO: 32]
TFCRRRRRRRR Peptide KP4-8R--
                                       [SEQ ID NO: 34]
KAFPRRRRRRRR Peptide KH6-8R--
                                       [SEQ ID NO: 36]
KAFPFHRRRRRRRR
```

Additional peptide sequences can be assembled to serve as further probes of structure-activity relationships (SAR). Computational studies indicate that the conformational arrangements available to Peptide A-8R [SEQ ID NO: 1] are not separated by large energy barriers. This, in turn, shows that numerous Peptide A-8R [SEQ ID NO: 1] conformations are viable candidates for binding. Thus, flexible systems can be utilized for the first set of probe molecules because their movement can survey a broad range of possible conformational space. In this regard, it is also important to assess the impact of inverting stereochemistry at selected amino acids, as well as to cap the N-terminus with simple acyl-functionalities and the carboxy-terminus with simple amide-moieties. Thus, some of the Peptide A derivatives listed above were synthesized having the carboxy terminus capped with amide-moieties. Specifically, as shown in Table 2 below, the following peptide derivatives were synthesized having a carboxy-terminus capped with an amide moiety:

PI5-8R [SEQ ID NO: 11];
TP7-8R [SEQ ID NO: 12];
TF6-8R [SEQ ID NO: 14];
FP6-8R [SEQ ID NO: 16];
FF5-8R [SEQ ID NO: 10];
FF5 [SEQ ID NO: 9] (amide-capped peptide referred to in Table 2 as FF5-NH2);
FF5-C2M-8R [SEQ ID NO: 18];
FF5-C2A-8R [SEQ ID NO: 20];
FF5-F1A-8R [SEQ ID NO: 22] (amide-capped peptide referred to in Table 2 as AF5-8R);
FF5-F5A-8R [SEQ ID NO: 24] (amide-capped peptide referred to in Table 2 as FA5-8R);
FF5-K3A-8R [SEQ ID NO: 26] (amide-capped peptide referred to in Table 2 as FF5-K3M-8R); and
CF4-8R [SEQ ID NO: 30].

Such caps begin the transition toward peptidomimetic probes that can be continued by replacing some of the amino acid side chains within A-8R [SEQ ID NO: 1] by chemical surrogates that provide modified physicochemical properties. Taking the FF5 sequence as an example, either or both of the "F's" phenyl-groups can be replaced by naphthalene so as to be twice as hydrophobic, or by a t-butyl moiety so as to assess the importance of an aromatic or planar system; the "C's" sulfhydryl-group can be replaced by a hydroxyl- or thioether moiety to enhance selectivity by being less compatible with various other biological surfaces seeking to engage in hydrogen bonding as either donors or acceptors; and "K's" primary amine can be replaced by a series having a range of basicity and steric features that can probe the sGCα1 pocket so as to potentially enhance selectivity upon optimization of these parameters for this very distinct locale. Alternatively, the alanine, as well as any of the other amide linkages within FF5, can itself be replaced by a peptide bond mimic that displays specified conformations in a semi-rigid manner.

The following table lists cell culture data for truncated Peptide A peptides. The amino acid sequences and $IC_{50}$ values in μM concentrations depict cytotoxicity after 3- and 6-day exposures ("NotA" means not active). "8R" [SEQ ID NO: 6] signifies that 8 arginines are present on the carboxy terminus to mediate membrane translocation. The data has shown that the 8R terminus [SEQ ID NO: 6] can be either as the free carboxy (—OH) or amide (—NH$_2$) with no alteration of permeation or observed activity.

TABLE 1

Truncated Peptide A Peptides
[SEQ ID NOS 1, 11, 12, 6, 16, and 10, respectively, in order of appearance]
Cytotoxicity Compared to Peptide A-8R
[SEQ ID NO: 1]

| Peptide Name | Sequence | $IC_{50}$ 3 Days | 6 Days |
|---|---|---|---|
| A-8R* | TFCKAFPFHII-8R | 8 | 16 |
| PI5-8R | ------PFHII-8R | NotA | NotA |
| TP7-8R* | TFCKAFP----8R | 16 | 23 |
| TF6-8R* | TFCKAF-----8R | 18 | 28 |
| FP6-8R* | -FCKAFP----8R | 22 | 35 |
| FF5-8R* | -FCKAF-----8R | 22 | 40 |

While potency is diminished, potency is nonetheless comparable to Peptide A-8R [SEQ ID NO: 1] when less than half of the peptide sequence is retained (e.g., Peptides TF6-8R [SEQ ID NO: 14] and FF5-8R [SEQ ID NO: 10]). All active peptides induced ROS. Cells treated with these peptides are rescued by NAC, a ROS-sequestering agent, mimicking what was observed with Peptide A-8R [SEQ ID NO: 1].

The table below lists LNCaP cell culture data for various Peptide A derivatives, displaying the observed $IC_{50}$ values in μM concentrations after 3- and 6-day exposures.

TABLE 2

Peptide A Derivatives [SEQ ID NOS: 5, 8, 7, 13, 15, 9, 9, 9, 17, 19, 21, 23, 25, 27, 29, 31, 33, and 35, respectively, in order of appearance] Cytotoxicity Compared to Peptide A-8R [SEQ ID NO: 1] (Table discloses sequence "Name(s)" as SEQ ID NOS: 1, 1, 11, 12, 14, 16, 10, 18, 20, 22, 24, 26, 28, 30, 32, 34, and 36, respectively, in order of appearance.)

| Peptide Name | Sequence | Cyto-toxicity | $IC_{50}$ (μM) Day 3 | Day 6 |
|---|---|---|---|---|
| TI11-8R (A-8R) | TFCKAFPFHII-OH | Yes | 8 | 16 |
| PI5-8R | ------PFHII-NH2 | No | | |
| TP7-8R | TFCKAFP----NH2 | Yes | 16 | 23 |
| TF6-8R | TFCKAF-----NH2 | Yes | 18 | 28 |
| FP6-8R | -FCKAFP----NH2 | Yes | 22 | 35 |
| FF5-8R | -FCKAF-----NH2 | Yes | 22 | 40 |
| FF5-OH | -FCKAF-----OH | No | | |
| FF5-NH2 | -FCKAF-----NH2 | No | | |
| FF5-C2M-8R | -FMKAF-----NH2 | Yes | 90 | 65 |
| FF5-C2A-8R | -FAKAF-----NH2 | Yes | ~210 | 145 |
| AF5-8R | -ACKAF-----NH2 | Yes | 200 | 160 |
| FA5-8R | -FCKAA-----NH2 | Yes | 160 | 120 |
| FF5-K3M-8R | -FCMAF-----NH2 | Yes | 60 | 38 |
| FA4-8R | -FCKA------OH | Yes | 43 | 90 |
| CF4-8R | --CKAF-----NH2 | Yes | 62 | 120 |
| TC3-8R | TFC--------OH | Yes | 72 | 140 |
| KP4-8R | ---KAFP----OH | No | | |
| KH6-8R | ---KAFPFH--OH | No | | |

Although FF5 was found to be inactive, the cell-based results indicate that potency is still quite comparable to Peptide A-8R [SEQ ID NO: 1] when only the first half of the peptide sequence is retained, as see with probes TF6-8R [SEQ ID NO: 14] and FF5-8R [SEQ ID NO: 10]. Based on a competitive binding assay, the active truncated peptide TF6-8R [SEQ ID NO: 14] bound to sGCα1 but the inactive KP4-8R [SEQ ID NO: 34] did not, clearly showing a direct correlation between cytotoxicity and binding to sGCα1.

Replacing cysteine with small molecule chelating moieties is feasible based on the results for FF5-C2M-8R [SEQ ID NO: 18] wherein a methionine was used to probe such possibilities and significant activity was retained, versus FF5-C2A-8R [SEQ ID NO: 20] wherein replacement by alanine dramatically reduced activity. Further SAR characterization of FF5-8R [SEQ ID NO: 10] using single alanine replacements indicates that both termini benefit from either a hydrophobic or aryl-stacking capability (FF5-F1A-8R [SEQ ID NO: 22] and FF5-F5A-8R [SEQ ID NO: 24]), while the centrally-located lysine should be amenable to a wider range of replacement possibilities (FF5-K3A-8R) [SEQ ID NO: 26]. The lower-level activities retained by the two tetra-peptides and the tri-peptide probes, FA4-8R [SEQ ID NO: 28], CF4-8R [SEQ ID NO: 30], and TC3-8R [SEQ ID NO: 32], respectively, indicate that even smaller analogues can be made when carefully constructed so as to display mimetic substituents in appropriate three-dimensional space.

It should be understood that many other truncated sequences and derivatives of Peptide A are within the scope of the present disclosure. By way of non-limiting example, it is known in the art that amino acids within the same conservative group can typically substitute for one another without substantially affecting the function of a protein. For the purpose of the present disclosure, such conservative groups are set forth in Tables A1 and A2, and are based on shared properties. See also, Alberts et al., "Small molecules, energy, and biosynthesis" 56-57 In: Molecular Biology of the Cell (Garland Publishing Inc. 3$^{rd}$ ed. 1994), the disclosure of which is incorporated herein by reference in its entirety.

TABLE A1

Amino Acid Conservative Substitutions

| Residue | Side Chain Polarity | Side Chain pH | Hydropathy Index | Preferred Conservative Substitution |
|---|---|---|---|---|
| Ala (A) | Non-polar | Neutral | 1.8 | Ser |
| Arg (R) | Polar | Basic (strongly) | −4.5 | Lys, Gln |
| Asn (N) | Polar | Neutral | −3.5 | Gln, His |
| Asp (D) | Polar | Acidic | −3.5 | Glu |
| Cys (C) | Non-polar | Neutral | 2.5 | Ser |
| Gln (Q) | Polar | Neutral | −3.5 | Asn, Lys |
| Glu (E) | Polar | Acidic | −3.5 | Asp |
| Gly (G) | Non-polar | Neutral | −0.4 | Pro |
| His (H) | Polar | Basic (weakly) | −3.2 | Asn, Gln |
| Ile (I) | Non-polar | Neutral | 4.5 | Leu, Val |
| Leu (L) | Non-polar | Neutral | 3.8 | Ile, Val |
| Lys (K) | Polar | Basic | −3.9 | Arg, Gln |
| Met (M) | Non-polar | Neutral | 1.9 | Leu, Ile |
| Phe (F) | Non-polar | Neutral | 2.8 | Met, Leu, Tyr |
| Pro (P) | Non-polar | Neutral | −1.6 | Gly |
| Ser (S) | Polar | Neutral | −0.8 | Thr |
| Thr (T) | Polar | Neutral | −0.7 | Ser |
| Trp (W) | Non-polar | Neutral | −0.9 | Tyr |
| Tyr (Y) | Polar | Neutral | −1.3 | Trp, Phe |
| Val (V) | Non-polar | Neutral | 4.2 | Ile, Leu |

TABLE A2

Amino Acid Conservative Replacements

| For Amino Acid | Replace With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

The following six groups each contain amino acids that are typical, but not necessarily exclusive, conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

Substantial changes in function or immunogenicity can be made by selecting substitutions that are less conservative than those listed in the table above, i.e., by selecting residues that differ more significantly in their effect on maintaining (a) the structure of the polypeptide backbone in the area of substitution, (b) the charge or hydrophobicity of the polypeptide at the target site, or (c) the bulk of a side chain. The substitutions that can generally be expected to produce the greatest changes in the polypeptide's properties are those in which (a) a hydrophilic residue, such as seryl or threonyl, is substituted by a hydrophobic residue, such as leucyl, isoleucyl, phenylalanyl, valyl, or alanyl; (b) a cysteine or proline is substituted by any other residue; (c) a residue having an electropositive side chain, such as lysyl, arginyl, or histidyl, is substituted by an electronegative side chain, such as glutamyl or aspartyl; (d) a residue having a bulky side chain, such as phyenylalanyl, is substituted by a residue not having a side chain, such as glycyl; or (e) by increasing the number of sulfation or glycosylation.

Compound Library

Further provided herein is an in vitro biochemical assay that can be deployed in high-throughput fashion to survey an initial compound library, the assay being based on the previously shown successful binding experiments. In brief, LNCap protein extract containing partially purified sGCα1 can be incubated with a saturating concentration of FITC-labeled Peptide A-8R [SEQ ID NO: 1] together with increasing concentrations of competing unlabeled A-8R [SEQ ID NO: 1] (as a standard run) or the various probe compounds. The amount of labeled material can be quantified for all runs and compared to the standard run so as to determine relative binding affinities. For example, over the course of testing, about 50 members can be added to the directed compound library from commercial sources and syntheses. All of these probes can be surveyed in the high-throughput screening campaign. Active compounds can be additionally studied within a panel of normal human cell lines that represent points of potential toxicity across several different tissue types. This type of assay is successfully utilized in a parallel approach to delineate STR among a series of compounds being sought as potential antibiotic chemotherapeutic agents. By pursuing structural relationships that can widen the gap between the desired efficacious effect on sGCα1 and the unwanted off-target potential side-effects/toxicity, compound candidates having enhanced selectivity for cancer cells are then identified.

One or more lead compounds can arise from screening this number of probe molecules according to the parallel testing approach. The desired profile for classification as an initial lead compound is nM potency (biochemical assay) within the molecular context of a peptidomimetic structure having 'drug-like' properties, accompanied by a dose requirement of at least 100 μM to produce significant effects on normal tissues (cell-based assay panel). However, because the compound library can be used to probe fundamental biology and establish SAR, the 'drug-like' specifications need not be overly stringent. Rather, they may serve as a guide according to the 'rule-of-five', avoidance of potential metabophore liabilities, and avoidance of blatant toxicophores. In addition, fundamental SAR and STR data be used to assist in extrapolation to other non-peptide, drug-like molecules via scaffold-hopping and pursuit of semi-rigid conformational analogs. The latter two strategies can be undertaken along with chemical scale-up to produce larger quantities of lead agents for more advanced biological characterizations.

The composite of SAR accumulating can also be used to guide the design of a probe molecule that can form a covalent bond within the A-8R [SEQ ID NO: 1] binding pocket on sGCα1. One approach is to incorporate a photoaffinity label that can be activated once the desired binding has occurred, rather than to use a chemically reactive functionality that could behave promiscuously in other bonding relationships. Both a benzophenone and an azide derivative can be utilized. Once a photoaffinity probe that retains a high level of binding activity is generated, the covalent interaction can be activated, and the so-bound probe-sGCα1 complex can be isolated and subjected to protein digestion protocols, followed by characterization of the resulting fragments by mass spectrometry analyses.

Computational Chemistry Strategies

Provided herein is a method of deriving new compounds with activity similar to that of Peptide A-8R [SEQ ID NO: 1], through computational chemistry strategies. Computational studies indicate that the conformational displays available to Peptide A-8R [SEQ ID NO: 1] are not separated by large energy barriers. Thus, analogous to the experimental assessments wherein synthesizing and testing semi-rigid analogs is best undertaken after deploying flexible systems to first identify the most active sequence arrangements, a variety of energy accessible shapes can be likewise considered during initial receptor docking studies.

Bacterial proteins related to sGCα1 or sGCβ1, with reasonable structural similarity, have various regions responsible for association of these biomolecules. Without wishing to be bound by theory, the dimer is thought to have 4 contact domains: 1 for guanylate cyclase, 2 important for protein-protein association, and 1 having a seemingly less important role. Peptide A-8R [SEQ ID NO: 1] is likely acting with sGCα1 at one of these important association sites that have been designated as the "H-NOXA" and "CC" domains. Without wishing to be bound by theory, it is believed Peptide A-8R [SEQ ID NO: 1] interacts with the H-NOXA domain. An x-ray of the H-NOXA domain is available from the species Nostoc punctiforme that has 35% sequence identity to the human form. An x-ray of the CC domain is available from the rat sGCβ1 monomer. These sequences can be converted to the human sGCα1 versions in increments of 5 to 10 amino acid residue changes while performing molecular dynamic simulations after each set of modifications. This approach can insure that the system retains a viable energy profile while also affording an opportunity to track the conformational impact on the proteins in an incremental and tractable manner. When the entire sequences have become 'humanized,' preliminary docking studies can be performed using a small series of 4 compounds selected from the directed library, including Peptide A-8R [SEQ ID NO: 1], which have a range of low, medium, and high potency in the experimental binding assay. The docking studies can be done with and without added water molecules. Optimization of parameters can then be attempted to as to rank the binding energies across the compound series to their corresponding experimental potencies. Data from the photoaffinity label studies can either confirm one of these domains and a specific site thereon as the binding pocket for Peptide A-8R [SEQ ID NO: 1], or identify some other new site for which a ligand's interaction can similarly disrupt protein-protein association. Once this level of binding site confirmation and compound series validation is established, the x-ray/computationally-derived docking model can be used to assist in further design of new compounds.

Prostate Cancer Animal Model Systems

Further provided is a method of evaluating the truncated variants and derivatives in animal models. It is to be understood that many other methods of evaluation are possible and are within the contemplated scope of the present disclosure.

Several androgen-dependent Pca xenograft models that respond initially to castration and subsequently relapse as castration-resistant tumors have been identified. These include LNCap, LCAPC4, CWR22, and VCaP xenografts. All of these models show high levels of AR expression and re-activation of androgen-regulated genes in the relapsed tumors. Importantly, sGCα1 expression is hormone-inducible in LNCaP and VCaP cells and constitutive at higher levels in CWR22 and C81 cells. However, LNCaP and CWR22 have different point mutations on the AR ligand-binding domain that are not commonly seen in CRPC patients. These mutations may allow AR more preferentially to bind to other steroids such as progesterone, an upstream of CYP17A1. On the other hand, VCaP expresses wild type AR, PSA, and TMPRSS2-ERG fusion gene (found in ~50% of Pca patients) and VCaP CRPC xenograft model has been successfully established. Unlike other models, most of androgen synthetic enzymes are expressed in VCaP cells and xenografts, and more significantly, the expression of AKR1C3 and HSD17B6 are upregulated in the relapsed tumor, suggesting that the intratumoral androgen synthesis is elevated in relapsed VCaP xenograft. Interestingly, this CRPC form of tumor responds to abiraterone (CYP17A1 inhibitor) treatment initially and developed resistance after a period of treatment (4-5 weeks). This phenomenon was similarly observed in abiraterone treated CRPC patients (~6 months for recurrence). It is now believed that there is possible involvement of AR splicing variants. Moreover, activity of AR as a transcriptional repressor in the full androgen circumstance. The targets of this suppression functions include AR itself, androgen synthetic genes (AKR1C3 and HSD16B6), and a group of cell cycle genes (MCM7, FANC1, cycline E1, etc.). Androgen deprivation treatments relieve the suppression on these genes and therefore increase the expressions in CRPC.

A regulation of SOX9, a gene critical for epithelial cells invading into urogenital sinus mesenchyme in developing prostate, by AR and TMPRSS2-ERG in VCaP cells and xenografts but not in fusion negative cells, leads to PCa tumor development. This is consistent with the findings in PCa patients. Also, it is now believed the sGCα1 gene may be a target of TMPRSS2-ERG in VCaP cells. Collectively, all this evidence indicates that VCap cells and xenografts are ideal models to study the PCa and development of CRPC after androgen deprivation. Thus, VCaP xenografts can be used to assess peptide effects on androgen-dependent tumors, and relapsed VCaP xenografts can be used to assess effects on CRPC tumors. In addition, alternative models such as LNCaP, CWR22, and LAPC4 can be used to validate and extend key findings in the VCaP xenografts.

The VCaP xenografts can be established through injecting 2 million cells (mixed with Matrigel) in the flank of male SCID mice (4-8 weeks). Tumor biopsies can be taken before the treatment.

In one example, three doses of Peptide A and truncated variants or derivatives thereof can be injected directly into tumors daily to each each group (6 per group) for up to 2 weeks, and then the mice can be sacrificed. The peptide doses will begin with 40 mg peptide/kg of animal, which was been shown previously (in Example I, above) to be highly effective against xenograft tumors from C81 cells. BrdU can be injected 2 hours before sacrifice to assess S-phase fraction. Paraffin sections of tumor tissue can be analyzed by immunohistochemistry for Ki67 and BrdU to assess effects on growth, and for cleaved caspase 3 and TUNEL staining for apoptosis. Protein extracted from frozen sections can be analyzed by Western blotting for sGCα1, sGCβ1, p53, Survivin, and other apotosis pathway proteins, and for activation status of pathways including PI3K/AKT and NFkB. Without wishing to be bound by theory, it is believed that AKT protein levels will drop and the other proteins will remain unchanged. The expression of any proteins identified as involved in peptide-induced ROS generation can also be measured. ROS generation in the tumors can be measured to assess Peptide A activity, which has been shown to kill PCa cells by enhancing ROS levels. cGMP levels can also be monitored to confirm that peptide treatment does not affect cGMP levels or NO signaling in general. Without wishing to be bound by theory, elevated ROS levels are anticipated in tumors treated with peptide. For an unbiased analysis, RNA extracted from frozen sections can be assessed by RNA-seq (or alternatively, expression microarray) in the pre-treatment biopsy samples versus the post-treatment tumors. The expression of genes downstream of AKT signaling is anticipated to change in response to peptide treatment. In addition, the effects on proliferation and apoptosis can also be studied, but it is to be understood that these effect are likely to be dependent on the spectrum of genes that are activated or repressed, and the magnitude of these effects.

In another example, PK/PD testing of these drugs can be performed in the plasma/tissues from the mice. These blood samples can be collected pre- and post-treatments and sent for pharmacokinetic studies. PK tests can be performed in male mice with established xenograft tumors. Agents can be evaluated after intratumor and intravenous delivery at a single efficacious dose. Oral and/or intraperitoneal delivery can be included for certain agents with improved properties for absorption. One or more final lead agents and back-up agents can be tested at three different doses per route. Blood samples can be collected via terminal cardiac puncture under anesthesia, with tumor tissues collected immediately after euthanasia. Blood samples can be centrifuged and serum stored at −80° C., while tumor tissue can be flash-frozen in liquid nitrogen and stored at −80° C. until analysis. Tumor tissues can be homogenized with a pestle in lysis buffer. Serum and tumor homogenate samples can be analyzed by LC-MS/MS assay on a system consisting of a Waters 2795 Alliance HT separations module, a Quattro Micromass triple quadruple mass spectrometer, and MassLynx software for instrument control, data acquisition, and analysis. Samples can be collected from five animals at each time point for each delivery route. A total of 5-8 time points after dosing can be evaluated to estimate elimination half-life, tumor half-life, serum and tumor AUC, and PO/IP bioavailability.

The expression of sGCα1 is increased in CRPC cell lines and human tissue samples versus primary PCa, while expression of sGCβ1 remains low. Therefore, the pro-proliferative, pro-survival functions of sGCα1 may be a mechanism for castration resistance and targeting sGCα1 with Peptide A, or a truncated variant or derivative thereof, may be a treatment of human CRPC. Peptide A is able to stop xenograft tumor growth from C81 cells, which is a model for CRPC, as shown in Example I above. To analyze the anti-cancer activities of the truncated variants and derivatives, the well-established CRPC xenograft models including VCaP and LAPC4 can be used. Subcutaneous xenografts can be established in the flanks of male SCID mice, and the mice can then be castrated. When the tumors relapse (usually in 6-8 weeks), biopsies can be taken to assess baseline gene expression. Groups of mice bearing these castration-resistant tumors (6 per group) can be treated with selected Peptide A analogs for about 2 weeks, and can then be sacrificed. While the previous xenograft evaluation with Peptide A have utilized direct intratumoral injections, other delivery methods are possible, including intraperitoneal, intravenous, or oral delivery. This model can develop drug-like compounds with increased stability and selectivity for prostate tumors. The IV delivery method is best for PK/PD studies.

Similar analysis as in Example I can be conducted for the truncated variants and derivatives. Biological triplicates for each model at an effective treatment can be further analyzed on RNA-seq or Affymetrix microarrays (in comparison with the matched pre-treatment biopsy) to globally assess effects on gene expression. Since VCaP xenograft can develop resistance to long-term exposure of arbiraterone, which is a FDA-approved CYP17A1 inhibitor to treat human CRPC, the effect of Peptide A truncated variants and derivatives can be assessed in a combination with abiraterone treatment (for example, three weeks of abiraterone and two weeks of co-treatment) on abiraterone-resistant VCaP CRPC xenograft (abiraterone pre-treated for 4 weeks).

Example III

Methods of the Invention

Also described herein are methods for treating, ameliorating one or more of the symptoms of, and reducing the severity of cancers or neoplastic diseases and related disorders (such as, but not limited to prostate cancer) as well as other disorders or conditions.

The methods and compositions can be used in the treatment of human cancers. Additionally, such compositions can be employed as part of a treatment of prostate cancer by administering a therapeutically effective amount of at least one of the compounds of the present invention as a single agent or in combination with another anti-cancer agent.

In particular, embodiments include methods of regulating androgen receptors levels in human prostate cancer cells by administering an effective amount of at least one effector agent to a subject in need of treatment.

In another broad aspect, there is provided herein a method for regulating expression of the tumor suppressor gene p53 in a subject in need thereof, comprising administering an effective amount of a composition comprising a soluble guanylyl cyclase alpha 1 (sGCα1)-type compound. In certain embodiments, the subject is suffering from prostate cancer.

In another broad aspect, there is provided herein a composition for regulating wild-type p53 protein in a subject in need thereof, comprising a soluble guanylyl cyclase alpha 1 (sGCα1)-type compound.

In another broad aspect, there is provided herein a method for mediating the proliferation of androgen-dependent and androgen-independent prostate cancer cells, comprising administering an effective amount of a composition comprising soluble guanylyl cyclase alpha 1 (sGCα1)-type compound.

In another broad aspect, there is provided herein a method for disrupting soluble guanylyl cyclase alpha 1 (sGCα1) interaction with p53, comprising administering an effective amount of a composition comprising a soluble guanylyl cyclase alpha 1 (sGCα1)-type compound.

In another broad aspect, there is provided herein a method for regulating p53 transcriptional activity in prostate cancer cells, comprising administering an effective amount of a composition comprising a soluble guanylyl cyclase alpha 1 (sGCα1)-type compound.

In another broad aspect, there is provided herein a method of reactivating p53 in cancer cells comprising administering an effective amount of a composition comprising a soluble guanylyl cyclase alpha 1 (sGCα1)-type compound.

In another broad aspect, there is provided herein a method of treating cancer, comprising administering to a subject in need of treatment an effective amount of at least one soluble guanylyl cyclase alpha 1 (sGCα1)-type compound.

In certain embodiments, the cancer is chosen from breast cancer and genital cancer. In a particular embodiment, the cancer is prostate cancer. Also, in certain embodiments, the prostate cancer is advanced prostate cancer characterized by androgen-independence. Further, in certain embodiments, the prostate cancer cells express wild-type p53.

In another broad aspect, there is provided herein a method where the soluble guanylyl cyclase alpha 1 (sGCα1)-type compound induces apoptosis in the prostate cancer cell by p53 accumulation.

In another broad aspect, there is provided herein a method for inducing p53 accumulation in a subject having prostate cancer comprising the step of administering a soluble guanylyl cyclase alpha 1 regulator to a subject in need thereof, whereby the induction of p53 accumulation aids the treatment of prostate cancer characterized by androgen-insensitivity.

In certain embodiments, the method can further include treating the subject with at least one conventional anticancer treatment chosen from radiation and chemotherapy. In certain embodiments, the method can further include treating the subject with at least one conventional anticancer agent. Suitable anticancer agents include, but are not limited to, chemotherapeutic agents; cytotoxins; antimetabolites; alkylating agents; protein kinase inhibitors; anthracyclines; antibiotics; antimitotic agents (e.g. antitubulin agents); corticosteroids; radiopharmaceuticals; proteins such as cytokines, enzymes, or interferons; biological response modifiers such as krestin, lentinan, sizofiran, picibanil, ubenimex; antiangiogenic compounds such as acitretin, fenretinide, thalidomide, zoledronic acid, angiostatin, aplidine, cilengtide, combretastatin A-4, endostatin, halofuginone, rebimastat, removal), Revlimid, squalamine, ukrain, or Vitaxin; platinum-coordinated compounds such as cisplatin, carboplatin, nedaplatin, or oxaliplatin; camptothecin derivatives such as camptothecin, 10-hydroxycamptothecin, 9-aminocamptothecin, irinotecan, SN-38, edotecarin, or topotecan; compounds or chelates that include radionuclides; or combinations thereof. Examples of suitable interferons include, but are not limited to interferon alpha, interferon alpha-2a, interferon, alpha-2b, interferon beta, interferon gamma-1a, interferon gamma-1b (Actimmune), interferon gamma-n1, or combinations thereof.

In certain embodiments, the anticancer agent is one or more of filgrastim, sizofilan, TheraCys, ubenimex, WF-10, aldesleukin, alemtuzumab, BAM-002, dacarbazine, daclizurnab, denileukin, gemtuzumab ozogamicin, ibriturnomab, imiquimod, lenograstim, lentinan, Corixa, molgramostim, OncoVAX-CL, sargramostim, tasonermin, tecleukin, thyrnalasin, tositumomab, Virulizin, Z-100, epratuzurnab, mitumomab, oregovomab, pemtumomab (Y-muHMFGI), Provenge (Dendreon), alitretinoin, arnpligen, atrasentan bexarotene, bortezomib. Bosentan, calcitriol, exisulind, finasteride.fotemustine, ibandronic acid, miltefosine, mitoxantrone, 1-asparaginase, procarbazine, dacarbazine, hydroxycarbamide, pegaspargase, pentostatin, tazarotne, Telcyta (TLK-286, Telik Inc.), Velcade (bortemazib, Millenium), tretinoinor, or combinations thereof.

In another broad aspect, there is provided herein a chemopreventative method of prophylactically treating cancer comprising administering to a subject in need of treatment an effective amount of at least one soluble guanylyl cyclase alpha 1 (sGCα1)-type compound.

In another broad aspect, there is provided herein a pharmaceutical composition comprising at least one soluble guanylyl cyclase alpha 1 (sGCα1)-type compound in combination with a pharmaceutically acceptable carrier, wherein the at least one soluble guanylyl cyclase alpha 1 (sGCα1)-type compound is present in a dosage level effective to treat cancer.

A method of decreasing androgen-associated cancer by regulating androgen receptors present in host cells, comprising exposing the host cells to an effective amount of at least one composition comprising a soluble guanylyl cyclase alpha 1 (sGCα1)-type compound.

In another broad aspect, there is provided herein a method of regulating androgen receptors in a subject in need thereof, comprising administering an effective amount of at least one composition to the subject, wherein the composition includes at least one soluble guanylyl cyclase alpha 1 (sGCα1)-type compound.

In another broad aspect, there is provided herein a method of down regulating p53 levels in human prostate cancer cells, comprising administering an effective amount of at least composition to a subject in need of treatment, wherein the composition includes at least one soluble guanylyl cyclase alpha 1 (sGCα1)-type compound.

In another broad aspect, there is provided herein a pharmaceutical composition comprising at least one composition in combination with a pharmaceutically acceptable carrier, wherein at least one composition is present in a dosage level effective to down regulate androgen receptors present in host cells, wherein the composition includes at least one soluble guanylyl cyclase alpha 1 (sGCα1)-type compound.

In another broad aspect, there is provided herein a novel p53 regulator, comprising a composition that disrupts sGCα1-p53 interaction in host cells.

In another broad aspect, there is provided herein a method for reactivating p53 in a subject in need thereof, comprising disrupting sGCα1-p53 interaction.

In another broad aspect, there is provided herein a method for treating a disease condition in a subject, comprising: providing a p53 regulator that disrupts sGCα1-p53 interaction; and administering the p53 regulator to the subject in an amount sufficient to treat the disease condition.

Kits

In another broad aspect, there is provided herein a kit comprising: a volume a p53 regulator that disrupts sGCα1-p53 interaction 1; and instructions for the use of the volume of p53 regulator in the treatment of a disease condition in a subject. In certain embodiments, the volume of p53 regulator is included in a composition that further comprises an additional component selected from the group consisting of a vehicle, an additive, a pharmaceutical adjunct, a therapeutic compound, a carrier, agents useful in the treatment of disease conditions, and combinations thereof.

In another broad aspect, there is provided herein a method of identifying an anti-prostate cancer agent, comprising providing a test agent to a cell and measuring the level of a p53 regulator that disrupts sGCα1-p53 interaction associated with altered expression levels in prostate cancer cells, wherein an increase or a decrease in the level of the p53 regulator in the cell, relative to a control cell, is indicative of the test agent being an anti-prostate cancer agent.

In another broad aspect, there is provided herein a method of determining the prognosis of a subject with prostate cancer, comprising measuring the level of at least one p53 regulator in a test sample from the subject, wherein: the p53 regulator is associated with an adverse prognosis in prostate cancer; and an alteration in the level of the at least one p53 regulator in the prostate test sample, relative to the level of a corresponding p53 regulator in a control sample, is indicative of an adverse prognosis.

In another broad aspect, there is provided herein a method of treating prostate cancer in a subject who has a prostate cancer in which at least one p53 regulator is down-regulated or up-regulated in the cancer cells of the subject relative to control cells, comprising: (1) when the at least p53 regulator is down-regulated in the cancer cells, administering to the subject an effective amount of at least one p53 regulator, or an isolated variant or biologically-active fragment thereof, such that proliferation of cancer cells in the subject is inhibited; or, (2) when the at least p53 regulator is up-regulated in the cancer cells, administering to the subject an effective amount of at least one compound for inhibiting expression of the at least p53 regulator, such that proliferation of cancer cells in the subject is inhibited.

In another broad aspect, there is provided herein a method of identifying an anti-prostate cancer agent, comprising providing a test agent to a cell and measuring the level of at least p53 regulator associated with an altered expression levels in prostate cancer cells, wherein an altered level of the p53 regulator in the cell, relative to a control cell, is indicative of the test agent being an anti-prostate cancer agent.

Pharmaceutical Compositions

In another embodiment, the present invention provides pharmaceutically acceptable compositions which comprise a therapeutically-effective amount of one or more of the effector agents described herein, formulated together with one or more pharmaceutically acceptable carriers (additives) and/or diluents. The pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) pulmonarily, or (9) nasally. As set out above, certain embodiments of the present compounds may contain a basic functional group, such as amino or alkylamino, and are, thus, capable of forming pharmaceutically-acceptable salts with pharmaceutically-acceptable acids.

The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The pharmaceutically acceptable salts of the compounds of the present invention include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Pharmaceutical compositions suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the compounds of the present invention may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the compounds of the present invention in biodegradable polymers such as polylactide-polyglycolide. Depending on the ratio of drug to polymer, and the nature of the particular polymer employed, the rate of drug release can be controlled. Non-limiting examples of other biodegradable polymers include poly(orthoesters) and poly(anhydrides). Depot injectable formulations are also prepared by entrapping the drug in liposomes or microemulsions which are compatible with body tissue.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound may also be administered as a bolus, electuary or paste.

When the compounds are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier. Regardless of the route of administration selected, the compounds, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose will be that amount of the compound which is the lowest dose effective to produce a therapeutic effect. Such an effective dose will generally depend upon the factors described above. Generally, oral, intravenous, intracerebroventricular and subcutaneous doses of the compounds for a patient, when used for the indicated analgesic effects, will range from about 0.0001 to about 100 mg per kilogram of body weight per day. If desired, the effective daily dose of the active compound may be administered as two, three, four, five, six or more sub-doses administered separately at appropriate intervals throughout the day, optionally, in unit dosage forms. Preferred dosing is one administration per day. While it is possible for a compound to be administered alone, it is preferable to administer the compound as a pharmaceutical formulation (composition).

The pharmaceutical compositions can, where appropriate, be conveniently presented in discrete unit dosage forms and/or kits and can be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system.

The compound can be administered as such or in admixtures with pharmaceutically acceptable carriers and can also be administered in conjunction with antimicrobial agents such as penicillins, cephalosporins, aminoglycosides and glycopeptides. Conjunctive therapy thus includes sequential, simultaneous and separate administration of the active compound in a way that the therapeutical effects of the first administered one is not entirely disappeared when the subsequent is administered.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Effector agents may be suitable for oral, rectal, nasal, topical (including buccal and sublingual), vaginal, or parenteral (including subcutaneous, intramuscular, subcutaneous, intravenous, intradermal, intraocular, intratracheal, intracisternal, intraperitoneal, and epidural) administration.

Effector agents may conveniently be presented in unit dosage form and may be prepared by conventional pharmaceutical techniques. Such techniques include the step of bringing into association one or more effector agents of the present invention and one or more pharmaceutical carriers or excipients.

It will be understood, however, that the total daily usage of the effector agents of the present invention will be decided by the attending physician within the scope of sound medical judgment. The specific therapeutically effective dose level for any particular subject will depend upon a variety of factors, including for example, the disorder being treated and the severity of the disorder; activity of the specific effector agents employed; the specific effector agents employed, the age, body weight, general health, sex and diet of the patient; the time of administration; route of administration; rate of excretion of the specific effector agents employed; the duration of the treatment; drugs used in combination or coincidental with the specific composition employed; and like factors well known in the medical arts. For example, it is well within the skill of the art to start doses of the effector agents at levels lower than those required to achieve the desired therapeutic effect and to gradually increase the dosage until the desired effect is achieved.

Effector agents of the present inventions are preferably formulated in dosage unit form for ease of administration and uniformity of dosage. "Dosage unit form" as used herein refers to a physically discrete unit of the effector agents appropriate for the subject to be treated. Each dosage should contain the quantity of effector agents calculated to produce the desired therapeutic affect either as such, or in association with the selected pharmaceutical carrier medium.

Preferred unit dosage formulations are those containing a daily dose or unit, daily sub-dose, or an appropriate fraction thereof, of the administered effector agent. In this regard, studies were performed to assess the dosage regimen.

Combinations

It is known in the art that many drugs are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining drugs are that it may promote additive or possible synergistic effects through biochemical interactions and also may decrease the emergence of drug resistance which would have been otherwise responsive to initial treatment with a single agent.

Beneficial combinations may be suggested by studying the activity of the test compounds with agents known or suspected of being valuable in the treatment of a particular disorder. This procedure can also be used to determine the order of administration of the agents, i.e. before, simultaneously, or after delivery.

Treatment of Cancer in Combination with Chemotherapy or Radiotherapy

In certain embodiments, the present invention relates to a method of treating or preventing prostate cancer in a subject, comprising administering to a subject in need thereof a therapeutically effective amount of any one or more of the aforementioned compounds.

In certain embodiments, one or more compounds of the present invention are used to treat or prevent cancer or neoplastic disease in combination with one or more anti-cancer, chemotherapeutic agents. Also, in certain embodiments, one or more compounds of the present invention can be used to treat or prevent cancer or neoplastic disease in combination with one or more chemotherapeutic or other anti-cancer agents including, but not limited to radiation.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents, and observed adverse affects.

Also, in general, compounds of the present invention and the chemotherapeutic agent do not have to be administered in the same pharmaceutical composition, and may, because of different physical and chemical characteristics, have to be administered by different routes. For example, compounds of the present invention may be administered intravenously to generate and maintain good blood levels, while the chemotherapeutic agent may be administered orally. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of chemotherapeutic agent or radiation will depend upon the diagnosis of the physicians and their judgment of the condition of the patient and the appropriate treatment protocol.

A compound of the present invention, and chemotherapeutic agent and/or radiation may be administered concurrently (e.g., simultaneously, essentially simultaneously or within the same treatment protocol) or sequentially, depending upon the nature of the proliferative disease, the condition of the patient, and the actual choice of chemotherapeutic agent and/or radiation to be administered in conjunction (i.e., within a single treatment protocol) with a compound of the present invention.

If a compound of the present invention and the chemotherapeutic agent and/or radiation is not administered simultaneously or essentially simultaneously, then the optimum order of administration of the compound of the present invention, and the chemotherapeutic agent and/or radiation, may be different for different tumors. Thus, in certain situations the compound of the present invention may be administered first followed by the administration of the chemotherapeutic agent and/or radiation; and in other situations the chemotherapeutic agent and/or radiation may be administered first followed by the administration of a compound of the present invention. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of a compound of the present invention followed, where determined advantageous, by the administration of the chemotherapeutic agent and/or radiation, and so on until the treatment protocol is complete.

Thus, in accordance with experience and knowledge, the practicing physician can modify each protocol for the administration of a component (therapeutic agent, i.e., compound of the present invention, chemotherapeutic agent or radiation) of the treatment according to the individual patient's needs, as the treatment proceeds.

Additional Definitions

The term "admixing" generally refers to the mixing the two components, and any additional optional components, together. Depending upon the properties of the components to be admixed, there may or may not be a significant chemical or physical interaction between two or more components when they are mixed. For example, if one component is an acid, and the other component is a base, upon Admixing, the two components may, depending on the strength of the acids and bases, react to form a salt comprising the anion corresponding to the acid and the protonated cation corresponding to the base, or an equilibrium mixture of the original acids and bases, and their salts. In such cases, it will be understood by those of ordinary skill in the art that the resulting composition may be claimed in terms of the components known to be present after the admixing process, or alternatively may be claimed in terms of the components admixed in a product-by-process claim format, especially if the exact nature of the product resulting from the process of admixing the components is unknown or only poorly known or understood.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

The term "androgen receptor" generally refers to a protein whose function is to specifically bind to androgen and, as a consequence of the specific binding, recognizes and binds to an androgen response element. Encompassed in the term "androgen receptor" are wild and mutant forms of an androgen receptor. Mutant forms of the androgen receptor are considered within the scope of embodiments of this invention as long as the function of mutant androgen receptor is sufficiently preserved. In addition, mutant androgen receptors include androgen receptors with amino acid additions, insertions, truncations and deletions, as long as the function is sufficiently preserved.

The terms "cancer" and "cancerous" generally refers to or describes the physiological condition in mammals that is typically characterized by unregulated cell growth. Included in this definition are benign and malignant cancers. By "early stage cancer" or "early stage tumor" is meant a cancer that is not invasive or metastatic or is classified as a Stage 0, I, or II cancer. The term "pre-cancerous" refers to a condition or a growth that typically precedes or develops into a cancer. A "pre-cancerous" growth will have cells that are characterized by abnormal cell cycle regulation, proliferation, or differentiation, which can be determined by markers of cell cycle regulation, cellular proliferation, or differentiation. By "dysplasia" is meant any abnormal growth or development of tissue, organ, or cells. Preferably, the dysplasia is high grade or precancerous. By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer. By "primary tumor" or "primary cancer" is meant the original cancer and not a metastatic lesion located in another tissue, organ, or location in the subject's body. By "benign tumor" or "benign cancer" is meant a tumor that remains localized at the site of origin and does not have the capacity to infiltrate, invade, or metastasize to a distant site. By "tumor burden" is meant the number of cancer cells, the size of a tumor, or the amount of cancer in the body. Tumor burden is also referred to as tumor load. By "tumor number" is meant the number of tumors.

The term "chemotherapeutic agent" generally refers to a chemical compound useful in the treatment of cancer. Non-limiting examples of chemotherapeutic agents include one or more chemical compounds useful in the treatment of cancer.

The terms "compound," and/or "compositions" as used herein also includes corresponding prodrugs of the compounds of the invention, including actetal prodrugs, and/or one or more pharmaceutically-acceptable salts or esters of the compound and/or prodrugs. As used herein, the term "composition" is intended to encompass a product comprising the specified ingredients in the specified amounts, as well as any product which results, directly or indirectly, from combination of the specified ingredients in the specified amounts.

The various compounds, compositions and/or effector agents disclosed herein can comprise a "carrier" molecule and/or the corresponding "carrier" functional group or residues that are either directly or indirectly bonded to another functional group or residue comprising one or more protease inhibitors. Such compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a number of different carrier molecules are disclosed and discussed, each and every combination and permutation of the carrier molecule and the protease inhibitor are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

In the many inter-related aspects of the inventions disclosed herein, the genera, subgenera, and species of compounds described herein, including their prodrugs and/or pharmaceutically acceptable salts, and their various pharmaceutical compositions and kits prepared thereof, can be used to treat or prevent prostate cancer.

The term "carrier molecule" as defined herein is any compound or functional group or residue thereof that can facilitate the delivery of the protease inhibitor into a muscle tissue. In one aspect, the carrier molecule can be any endogenous molecule. In an alternative embodiment, the carrier molecule can be a derivative of an endogenous compound.

Any of the carrier molecules or residues, linkers, and/or protease inhibitors described herein, and the compounds derived therefrom, can be employed in the form of a pharmaceutical composition, or used to prepare or manufacture pharmaceutical compositions or medicaments.

The term "cytotoxic agent" generally refers to a substance that inhibits or prevents the function of cells and/or causes destruction of cells. The term is intended to include radioactive isotopes e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

The term "effective amount" of a subject compound, with respect to the present methods of treatment, generally refers to an amount of the antagonist in a preparation which, when applied as part of a desired dosage regimen brings about, e.g., a change in the rate of cell proliferation and/or rate of survival of a cell according to clinically acceptable standards for the disorder to be treated.

The term "effector agent" generally refers to as any small molecule that interacts with a receptor, either directly or indirectly, in a manner that alters its ability to bind a ligand. A positive effector enhances binding activity while a negative effector reduces it.

Effector agents and compositions containing the same can be used to treat conditions such as, but not limited to, cancer and cancer-related diseases. In addition, effector agents can be used prophylactically as chemopreventative compositions that can be used to inhibit the development and/or slow the development of the cancer and cancer-related conditions and/or advanced stages of cancer and cancer-related conditions. In certain embodiments, the "effector agents" can be used to treat these cancers and other cancers at any stage from the discovery of the cancer to advanced stages. In addition, effector agents can be used in the treatment of the primary cancer and metastases thereof.

Effector agents may be used as the active ingredient in combination with one or more pharmaceutically acceptable carrier mediums and/or excipients. Except insofar as any conventional carrier medium is incompatible with the effector agents used in practicing embodiments of the invention, such as by producing any undesirable biological effect or otherwise interacting in a deleterious manner with one or more of the effector agents of the pharmaceutical composition, its use is contemplated to be within the scope of the embodiments of this invention.

The term "host cells" include non-cancerous and cancerous cells. "Cancerous cells" include, but are not limited to, cancer cells, neoplastic cells, neoplasia, tumors, and tumor cells, which exhibit relatively autonomous growth, so that they exhibit an aberrant growth phenotype, characterized by a significant loss of control of cell proliferation.

The term "pharmaceutically acceptable salt form" generally refers to those salt forms that retain the biological effectiveness and properties of the effector agent. Non-limiting examples of such salts include: (1) acid addition salt which is obtained by reaction of the free base of the parent compound with inorganic acids such as hydrochloric acid, hydrobromic acid, nitric acid, 5 phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid such as the L-malate salt of sunitinib; or (2) salts formed when an acidic proton present in the parent compound either is replaced by a metal ion, e.g., an alkali metal ion, an alkaline earth ion; or coordinates with an organic base. Exemplary ions include aluminum, calcium, lithium, magnesium, potassium, sodium and zinc in their usual valences. Preferred organic base include protonated tertiary 15 amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine.

By "pharmaceutically acceptable salt" it is meant those salts which are, within the scope of sound medical judgment, suitable for use in contact with the tissues of subjects without undue toxicity, irritation, allergic response and the like, and are commensurate with a reasonable benefit/risk ratio and effective for their intended use. The salts can be prepared in situ during the final isolation and purification of one or more effector agents, or separately by reacting the free base function with a suitable organic acid.

The term "pharmaceutically acceptable esters" as used herein refers to those esters of one or more effector agents which are suitable, within the scope of sound medical judgment, for use in contact with the tissues of subjects without undue toxicity, irritation, allergic response, and the like, are commensurate with a reasonable benefit/risk ratio, and are effective for their intended use.

The term "pharmaceutically acceptable prodrugs" as-used herein refers to those prodrugs of one or more effector agents which are, within the scope of sound medical judgment, suitable for use in contact with the tissues of subjects without undue toxicity, irritation, allergic response, and the like, are commensurate with a reasonable benefit/risk ratio, and are effective for their intended use. Pharmaceutically acceptable prodrugs also include zwitterionic forms, where possible, of one or more compounds of the composition. The term "prodrug" refers to compounds that are rapidly transformed in vivo to yield the parent compound, for example by hydrolysis in blood.

The term "prodrug" refers to a precursor or derivative form of a pharmaceutically active substance that is less cytotoxic to tumor cells compared to the parent drug and is capable of being enzymatically activated or converted into the more active parent form.

By "radiation therapy" can include the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

By "reduce or inhibit" is meant the ability to cause an overall decrease of 20%, 30%, 40%, 50%, 60%, 70%, 75%, 80%, 85%, 90%, 95%, or greater. Reduce or inhibit can also refer to the symptoms of the disorder being treated, the presence or size of metastases, the size of the primary tumor, or the size or number of the metastatic tumor.

A "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention.

The term "subject" or "patient" generally refers to an animal, typically a mammal or a human that has been the object of treatment, observation, and/or experiment. Also, by "subject" is meant a mammal, including, but not limited to, a human or non-human mammal, such as a bovine, equine, canine, ovine, or feline. In one embodiment, the subject is a human. When the term is used in conjunction with administration of a compound or drug, then the subject has been the object of treatment, observation, and/or administration of the compound or drug. Subjects that are "predisposed" to cancer and cancer-related conditions can be defined as subjects that do not exhibit overt symptoms of one or more of these conditions but that are genetically, physiologically, or otherwise at risk of developing one or more of these conditions. Thus, compositions and effector agents of the present invention can be used prophylactically as chemopreventative agents for these conditions The term "therapeutically effective amount" as used herein means that amount of active compound or pharmaceutical agent that elicits the biological or medicinal response in a tissue, system, animal or human that is being sought by a researcher, veterinarian, medical doctor or other clinician. For cancer therapy, efficacy in vivo can, for example, be measured by assessing the duration of survival, time to disease progression (TTP), the response rates (RR), duration of response, and/or quality of life.

In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

As used herein, "treat", "treating", and "treatment" are an approach for obtaining beneficial or desired clinical results. For purposes of embodiments of this invention, beneficial or desired clinical results include, but are not limited to, alleviation of symptoms, diminishment of extent of disease, stabilization (i.e., not worsening) of disease, preventing spread (i.e., metastasis) of disease, delaying or slowing of disease progression, amelioration or palliation of the disease state, and remission (partial or total) whether detectable or undetectable. In addition, "treat", "treating", and "treatment" can also mean prolonging survival as compared to expected survival if not receiving treatment.

The term "treatment" can also refer to both therapeutic treatment and prophylactic or preventative measures. Those in need of treatment include those already having a benign, pre-cancerous, or non-metastatic tumor as well as those in which the occurrence or recurrence of cancer is to be prevented.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

"Up and/or down regulation" or "up or down regulating" can be defined as an increase or decrease in the number of ligand receptors or other cellular proteins within or on the surface of a host cell. Such up- or down-regulation occurs after host cells have been exposed to an effector agent, either as a result of a direct interaction of the effector agent with the receptor or other protein, or through indirect interactions.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

The publication and other material used herein to illuminate the invention or provide additional details respecting the practice of the invention, are incorporated be reference herein, and for convenience are provided in the following bibliography.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

What is claimed is:

1. An isolated peptide, FA4-8R, consisting of the amino acid sequence set forth in [SEQ ID NO: 28], having an OH on the carboxy terminus.

2. A pharmaceutical composition comprising: the peptide of claim 1; and a pharmaceutically-acceptable carrier.

3. The composition of claim 2, further comprising a chemotherapeutic agent.

* * * * *